US008901177B2

(12) United States Patent
Bencherif et al.

(10) Patent No.: US 8,901,177 B2
(45) Date of Patent: Dec. 2, 2014

(54) METHOD OF TREATING BLADDER DISORDERS

(71) Applicant: Targacept, Inc., Winston-Salem, NC (US)

(72) Inventors: Merouane Bencherif, Winston-Salem, NC (US); Steven M. Toler, Winston-Salem, NC (US)

(73) Assignee: Targacept, Inc., Winston-Salem, NC (US)

( * ) Notice: Subject to any disclaimer, the term of this patent is extended or adjusted under 35 U.S.C. 154(b) by 0 days.

(21) Appl. No.: 13/798,248

(22) Filed: Mar. 13, 2013

(65) Prior Publication Data

US 2013/0253067 A1  Sep. 26, 2013

Related U.S. Application Data

(60) Provisional application No. 61/614,892, filed on Mar. 23, 2012, provisional application No. 61/696,097, filed on Aug. 31, 2012.

(51) Int. Cl.
*A61K 31/13* (2006.01)

(52) U.S. Cl.
CPC ........................................ *A61K 31/13* (2013.01)
USPC ............................................................ 514/661

(58) Field of Classification Search
CPC .............................. A61K 31/13; A61K 31/137
See application file for complete search history.

(56) References Cited

U.S. PATENT DOCUMENTS

| 6,034,079 A | 3/2000 | Sanberg et al. |
| 6,734,215 B2 | 5/2004 | Shytle et al. |
| 6,979,698 B1 | 12/2005 | Sandberg et al. |
| 7,101,916 B2 | 9/2006 | Shytle et al. |
| 8,026,283 B2 | 9/2011 | Shytle et al. |

FOREIGN PATENT DOCUMENTS

| EP | 1 634 498 B1 * | 3/2008 |
| WO | WO-2011/008686 | 1/2011 |
| WO | WO 2011/149859 A1 * | 12/2011 |
| WO | WO 2011/149862 A1 * | 12/2011 |

OTHER PUBLICATIONS

Papke et al ("Analysis of Mecamylamine Stereoisomers on Human Nicotinic Receptor Subtypes". Journal for Pharmacological and Experimental Therapeutics, 2001; 297:646-656).*
De Biasi et al ("Nicotinic acetylcholine receptors in the autonomic control of bladder function". European Journal of Pharmacology, 2000; 393:137-140).*
Nickell et al., "Potential Therapeutic Uses of Mecamylamine and its Steroisomers," Pharmacology, Biochemistry and Behavior 108 (2013) 28-43.
Matsumoto et al., "Differential roles of M2 and M3 muscarinic receptor subtypes in modulation of bladder afferent activity in rats," Urology. Apr. 2010; 75(4): 862-867.

(Continued)

*Primary Examiner* — Wu-Cheng Winston Shen
*Assistant Examiner* — Rayna B Rodriguez
(74) *Attorney, Agent, or Firm* — Amy H. Fix; Womble Carlyle Sandridge & Rice, LLP

(57) ABSTRACT

The present invention relates to dexmecamylamine and the use of dexmecamylamine, substantially free of exo-R-mecamylamine, in the treatment of bladder disorders, including overactive bladder.

7 Claims, 35 Drawing Sheets

(56) References Cited

OTHER PUBLICATIONS

McCallum et al., "Mecamylamine prevents tolerance but enhances whole brain [$^3$H]epibatidine binding in response to repeated nicotine administration in rats," Psychopharmacology (Berl). May 2000;150(1):1-8.

Algelico et al., "Urodynamic effects of oxybutynin and tolterodine in conscious and anesthetized rats under different cystometrographic conditions," *BMC Pharmacology* 2005, 5:14 doi:10.1186/1471-2210-5-14.

Stone et al., "Ganglionic Blocking Properties of 3-Methylaminoisocamphane Hydrochloride (Mecamylamine): A Secondary Amine," JPET Jun. 1956 vol. 117 No. 2 169-183.

Wang et al., "Chronic Nicotine Treatment Up-Regulates Human α3β2 but Not α3β4 Acetylcholine Receptors Stably Transfected in Human Embryonic Kidney Cells," The Journal of Biological Chemistry, vol. 273, No. 44, 1998, pp. 28721-28732.

Vidrio et al., "Some Consequences of Long Term Mecamylamine Administration to Experimental Animals," The Journal of Pharmacology and Experimental Therapeutics, vol. 149, No. 1, 1965, pp. 98-105.

Oki et al., "Advantages for Transdermal over Oral Oxybutynin to Treat Overactive Bladder: Muscarinic Receptor Binding, Plasma Drug Concentration, and Salivary Secretion," JPET Mar. 2006 vol. 316 No. 3 1137-1145.

Chapple et al., "Clinical efficacy, safety, and tolerability of once-daily fesoterodine in subjects with overactive bladder," *Eur Urol*, Oct. 2007;52(4):1204-12. Epub Jul. 17, 2007.

Poonia et al., "New insights into molecular targets for urinary incontinence," Indian J Pharmacol 2010;42;261-6.

Kaplan et al., "Reduction of bladder contractility after alpha-adrenergic blockade and after ganglionic blockade," Acta Neurologica Scandinavica, vol. 59, Issue 4, pp. 172-177, Apr. 1979.

Hodges et al., Voiding Pattern Analysis as a Surrogate for Cystometric Evaluation in Uroplakin II Knockout Mice, the Journal of Urology, vol. 179, pp. 2046-2051, May 2008.

Zhao et al., "impaired Bladder Function in Aging Male Rats," The Journal of Urology, vol. 184 issue 1 (Nov. 30, 2009), pp. 378-385.

Chappele et al., "A Pooled Analysis of Three Phrase III Studies to Investigate the Efficacy, Tolerability and Safety of Darifenacin, a Muscarinic $M_3$ Selective Receptor Antagonist, in the Treatment of Overactive Bladder," BJU International, vol. 95, pp. 993-1001, 2005.

Freis et al., "Mecamylamine, a New, Orally Effective, Hypotensive Agent", Archives of Internal Medicine, 1956, vol. 97, pp. 551-561.

Sakata et al., "Biodistribution and radiation dosimetry of the $α_7$ nicotinic acetylcholine receptor ligand [$^{11}$C]CHIBA-1001 in humans," Nuclear Medicine and Biology, vol. 38, Issue 3 , pp. 443-448, Apr. 2011.

De Biasi, "Nicotinic mechanisms in the autonomic control of organ systems, Journal of Neurobiology," Special Issue: Nicotinic Signaling vol. 53, Issue 4, pp. 568-579, Dec. 2002.

Soloway, ICUD-EAU International Consultation on Bladder Consulation on Bladder Cancer 2012: Recommendations on Bladder Cancer—Progress in a Cancer that Lacks the Limelight, European Urology 63 (2013) 1-3.

Bschleipfer et al., "Bladder Outlet Obstruction Influences mRNA expression of cholinergic receptors on sensory neurons in mice," Life Sci (2012)doi: /j.lfs.2012.05.007.

Nachman et al., "Urologist Bullish on Botox OAB, Cautious on Mesh," Specialty Pharma, SIG Susquehanna Financial Group, Dec. 13, 2012.

Martinez-Ferrer et al., "Role of Nicotinic and Estrogen Signlaing during Experimental Acute and Chronic Bladder Inflammation," Am J Pathol. Jan. 2008; 172(1): 59-67.

Fowler et al., "The Neural Control of Micturition," Neuroscience Nature Reviews, vol. 9, Jun. 2008, pp. 453-466.

Digesu et al., "Bladder sensations during filling cystometry are different according to urodynamic diagnosis," Neurourol Urodyn 2009; 28(3):191-6.

Nandigama, R., et al., "Muscarinic acetylcholine receptor subtypes expressed by mouse bladder afferent neurons," Neuroscience 168: 842-850, 2010.

Mallory et al., "Pharmacological modulation of the pontine micturition center," Brain Research vol. 546, Issue 2, Apr. 19, 1991, pp. 310-320.

Young et al., Mecamylamine: new therapeutic uses and toxicity/risk profile, Clinical Therapeutics, vol. 23, Issue 4, Apr. 2001, pp. 532-565.

Novara et al., "Mirabegron as a New Class of Oral Drug for Overactive Bladder Syndrome: Many Positive Perspectives, Some Concerns," European Urology, vol. 63, issue 2, pp. 306-308, Feb. 2013.

Chapple et al., "Randomized double-blind, active-controlled phase 3 study to assess 12-month safety and efficacy of mirabegron, a β(3)-adrenosceptor agonist, in overactive bladder,"*Eur Urol*. Feb. 2013;63(2):296-305, doi: 10.1016/j.eururo.2012.10.048. Epub Nov. 6, 2012.

Masuda et al., "Effects of cholinesterase inhibition in supraspinal and spinal neural pathways on the micturition reflex in rats," BJU Int. Oct. 2009; 104(8): 1163-1169.

Clemens, "Basic Bladder Neurophysiology," Urol Clin N Am 37 (2010) 487-494.

Nandigama et al., "Expression of nicotinic acetylcholine receptor subunit mRNA in mouse bladder afferent neurons," Neuroscience 229 (2013), pp. 27-35.

Bschleipfer et al., "Expression and distribution of cholinergic receptors in the human urothelium," Life Sciences 80 (2007) 2303-2307.

Ochodnicky et al., "Eurotrophins as regulators of urinary bladder function," Nature Reviews Urology 9, 628-637 (Nov. 2012).

Bhide et al., "Biomarkers in Overactive Bladder," Int Urogynecol 2, 2013.

Murphy et al., "Treatment of Overactive Bladder: What is on the Horizon," Int Urogynecol J (2013) 24:5-13.

Sky et al., Objective Evaluation of Overactive Bladder: Which Surveys Should I Use?, Curr Bladder Dysfunct Rep. (2013) 8:45-50.

Gromley et al., "Diagnosis and Treatment of Overactive Bladder (Non-Neurogenic) in Adults: AUA/SUFU Guidelines," J Urol. Dec. 2012; 188(6 Suppl):2455-63.

Cornu et al., "Overactive Bladder Medical Management in the Elderly: It is Time to Go Beyond the Tip of the Iceberg," Euro Urol (2013) , pp. 1-2.

Yokoyama et al., "Urodynamic Effects of Intravesical Oxybutynin Chloride in Conscious Rats," The Journal of Urology, vol. 151, pp. 768-771, Feb. 1996.

Dale et al., Treatment-responsive Pandysautonomia in an Adolescent with Ganglionic α3-AChR Antibodies, European Journal of Paediatric Neurology 16 (2012) 396-398.

Masuda et al., "Roles of Peripheral and Central Nicotinic Receptors in the Micturition Reflec in Rats," The Journal of Urology, vol. 176, pp. 374-379, Jul. 2006.

Yamamoto et al., "Up-regulation of Nicotinic and Muscarinic Receptor mRNA in Rat Bladder by Repeated Administration of Nicotine in Relation to the Pharmacokinetics," Life Sciences 89 (2011) 343-348.

Hicks et al., "GW427353 (solabegron), a novel, selective beta3-adrenergic receptor agonist, evokes bladder relaxation and increases micturition reflex threshold in the dog," J Pharmacol Exp Ther. Oct. 2007; 323(1):202-9.

Ohlstein et al., "A Multicenter, Double-blind, Radomized, Placebo-controlled Trial of the β3-Adrenoceptor Agonist Solabegron for Overactive Bladder," Eur Urol. Jun. 5, 2012.

Chapple, "β3-agonist therapy: a new advance in the management of overactive bladder?," Eur Urol. Nov. 2012;62(5):841-2.

Ukimura et al., "The Neurometer as an Instrument for Appropriate Selection and Monitoring of Intravesical Resiniferatoxin Therapy for Patients with Detrusor Hyperreflexia," International Continence Society, 40, 2002.

Yokoyama et al., "Role of C afferent fibers and monitoring of intravesical resiniferatoxin therapy for patients with idiopathic detrusor overactivity," The Journal of Urology, vol. 172, Issue 2, Aug. 2004, pp. 596-600.

(56) References Cited

OTHER PUBLICATIONS

Nishijima et al., "Comparison of the Effect of Anti-Muscarinic Agents on Rats on Bladder Activity, Urinary ATP Level, and Autonomic Nervous System in Rats," Biomedical Research 30 (2) 107-112, 2009.

Beckel et al., "Expression of functional nicotinic acetylcholine receptors in rat urinary bladder epithelial cells," *Am J Physiol Renal Physiol* 290, F103-F110, 2006.

Zeilhofer, "Functional Anatomy of the Rodent Spinal Cord," Institute of Pharmacology and Toxicology, Sep. 24, 2012.

Masuda et al., "Roles of Peripheral and Central Nicotinic Receptros in the Micturition Reflex in Rats," Journal of Urology, vol. 176, No. 1, Jul. 1, 2006, pp. 374-379.

Lippiello et al., "TC-5214 (S-(+)-Mecamylamine with Antidepressant Activity," CNS Neuroscience and Therapeutics, vol. 14, No. 4, Jan. 1, 2008, pp. 266-277.

International Search Report and Written Opinion for International Application No. PCT/US2013/030640 mailed May 8, 2013.

Herrera, "Urodynamic Profiling of Targacept Compounds Using Awake Ambulatory Cystometry", Canamount Research and Development Company, May 22, 2013, pp. 1-16.

* cited by examiner

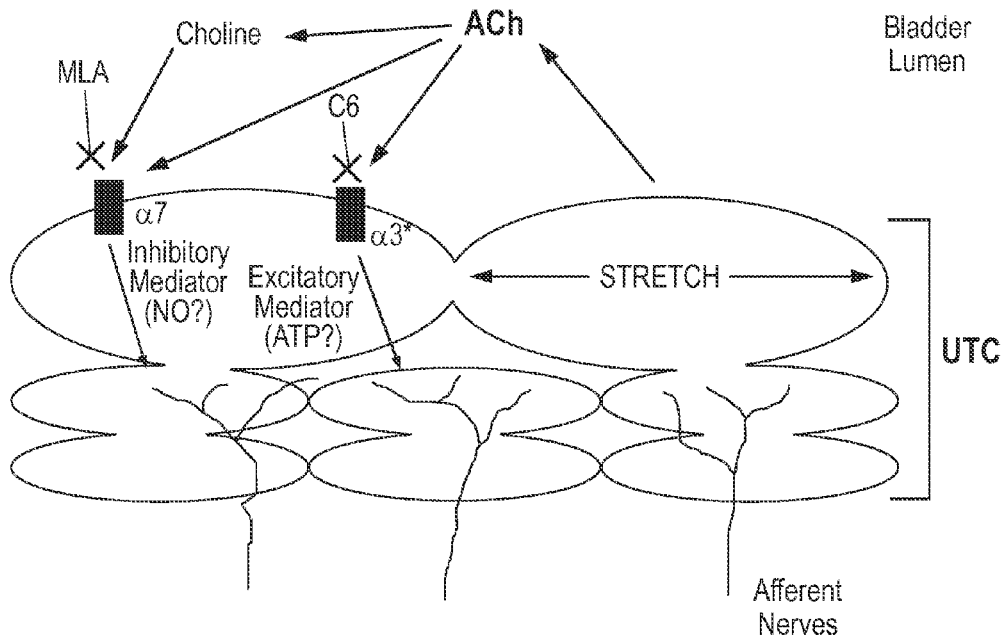

Fig. 1

- Animals
  - Female Sprague Dawley rats (200-270 g) from Charles River France.
  - Housing: 3 – 4 rats / cage.

- Surgery (D-2)
  - Rats were anesthetized with isoflurane (1.5-3 %).
  - Two days before cystometry, a polyethylene catheter was implanted in the bladder through the dome and exteriorized at the scapular level.
  - Each rat was housed individually after surgery.

- Cystometry (D0)
  - Rats were placed into a restraining device.

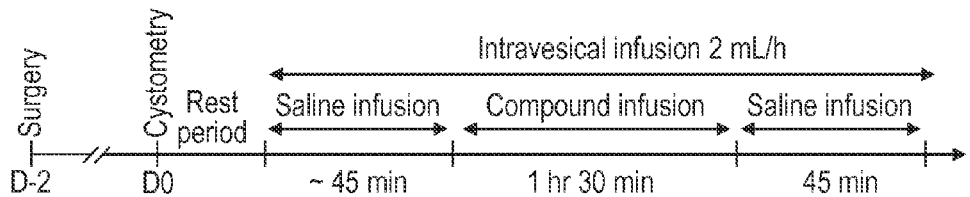

Fig. 2

| Experimental Parameters | Beckel | UROSphere |
|---|---|---|
| Species | Female Sprague-Dawley (250-275g) Vendor: Not identified | Female Sprague-Dawley (250-275g) Vendor: Charles River France |
| Anesthesia | Urethane (1.2 g/kg) | Isoflurane (1.5 - 3%) |
| Recovery from bladder catheter implantation | None: Study conducted in anesthetized rats immediately following surgery | 48 hrs: Study conducted in conscious but restrained rats |
| Vehicle | Saline (0.04 mL/min) | Warm physiological saline (0.03 mL/min) |
| Acclimation Period (to recover from surgery) | Saline (0.04 mL/min) for 1 hour | Not Applicable |
| Baseline Period | Saline (0.04 mL/min) for 1 hour | Saline (0.03 mL/min) for 0.75 hour |
| Testing Period | No saline control was included Hexamethonium (1, 10 & 100 µM) for 1 hr Nicotine (0.05 & 1 µM) for 1hr Methyllycaconitine (10 & 100 µM) for 1 hr Choline (10 & 100 µM) for 1 hr | Saline for 1.5 hr Hexamethonium (10 µM) for 1.5 hr Tolterodine (10 µM) for 1.5 hr TC-5213 (0.1, 1, & 10 µM) for 1.5 hr TC-5214 (0.1, 1, & 10 µM) for 1.5 hr |
| Washout Period | Saline (0.04 mL/min) for 1 hr only after nicotine treatment | Saline (0.03 mL/min) for 0.75 hour |
| Measurements | Intercontraction interval (ICI) | Intercontraction interval (ICI, timing between subsequent micturitions), Amplitude of bladder contractions (AM), Micturition frequency (MF), and Bladder capacity (BC) |
| Outcomes | Compared each group to its basal values for ICI Significant effects with nicotine (0.05 & 1 µM), hexamethonium (10 & 100 µM) & choline (10 & 100 µM) | Compared each group to its basal values for ICI Significant effects with Tolterodine (10 µM) & TC-5213 (1 & 10 µM) No significant effects with Hexamethonium or TC-5214 Compared each drug to the vehicle control No significant effects |

*Fig. 6*

- Animals
  - Female Sprague Dawley rats (200-290 g) from Charles River France.
  - Housing: 3 – 4 rats / cage

- Surgery
  - Rats were anesthetized with urethane (1.2 g/kg s.c., 3 mL/kg)
  - A polyethylene catheter was implanted into the bladder through the dome
  - Ureters were tied and cut

*Fig. 13*

Dynaflow Protocol Editor Pro

File  Edit  View  Help

Chip
160310-a3b4-OCS.dfp

| Channel | Content | Concentration |
|---------|---------|---------------|
| 1 | ACh | 30 |
| 2 | 0 | 0 |
| 3 | Control | 0 |
| 4 | 0 | 0 |
| 5 | 0 | 0 |
| 6 | 5231 | 0.1 |
| 7 | 5231 | 0.1 |
| 8 | Ach+5231 | 30+0.1 |
| 9 | 0 | 0 |
| 10 | 0 | 0 |
| 11 | 0 | 0 |
| 12 | 0 | 0 |
| 13 | 0 | 0 |

Protocol  Chip -- 160310-a3b4-OCS.dfc

Chip Create Date: 3/16/2010 | Chip Type: df48 | Path: W:\Axon\2010\March 2010\160310\160310-a3b4-OCS.d Version: 1.3   (Build: 1.1)

Fixed dose studies of 8 weeks (TC-5214) and 3 months duration (others)

| | UTI | Urinary Retention |
|---|---|---|
| TC-5214 0.1 mg | 0.85% | 0% |
| TC-5214 0.5 mg | 1.57% | 0% |
| TC-5214 1 mg | 1.42% | 0% |
| TC-5214 2 mg | 1.60% | 0.63% |
| TC-5214 4 mg | 1.80% | 0.91% |
| Vesicare 5 mg | 0.00% | 0.00% |
| Vesicare 10 mg | 2.00% | 0.80% |
| Toviaz 4 mg | 0.10% | 0.90% |
| Toviaz 8 mg | 0.90% | 1.20% |

Values in Table are Placebo corrected: Placebo UTIs = 0.31%, UR = 0.0%

*Fig. 24*

|  | base | treat | diff | base | treat | diff | base | treat | diff |
|---|---|---|---|---|---|---|---|---|---|
| CONTROL | | | | | | | | | |
| Targ 38 | 9.92 | 7.42 | -2.50 | 1.65 | 1.19 | -0.46 | 1.65 | 1.24 | -0.41 |
| Targ 52 | 8.33 | 8.75 | 0.42 | 1.39 | 1.42 | 0.03 | 1.39 | 1.46 | 0.07 |
| Targ 53 | 5.00 | 10.06 | 5.06 | 0.73 | 1.50 | 0.77 | 0.83 | 1.68 | 0.85 |
| Targ 54 | 6.67 | 9.43 | 2.76 | 1.01 | 1.46 | 0.45 | 1.11 | 1.57 | 0.46 |
| Targ 55 | 13.67 | 14.71 | 1.04 | 2.28 | 2.45 | 0.17 | 2.28 | 2.45 | 0.17 |
| Targ 58 | 5.62 | 6 | 0.38 | 0.80 | 0.92 | 0.12 | 0.94 | 1 | 0.06 |
| Targ 59 | 5.11 | 5.74 | 0.63 | 0.77 | 0.84 | 0.07 | 0.85 | 0.96 | 0.11 |
| Targ 62 | 3.37 | 5.99 | 2.62 | 0.56 | 0.90 | 0.34 | 0.56 | 1 | 0.44 |
| Mean | 7.21 | 8.51 | 1.30 | 1.15 | 1.34 | 0.19 | 1.20 | 1.42 | 0.22 |
| STD | 3.32 | 3.01 | 2.22 | 0.585 | 0.526 | 0.36 | 0.554 | 0.500 | 0.37 |
| Within Group | 0.142 | | | 0.179 | | | 0.139 | | |
| Between Group | MIC | 0.0852 | | MV | 0.0685 | | BC | 0.0871 | |

Fig. 30A

| Control | RV | | | BP | | | TP | | |
|---|---|---|---|---|---|---|---|---|---|
| | base | treat | diff | base | treat | diff | Base | treat | diff |
| Targ 38 | 0 | 0.04 | 0.04 | 7.52 | 5.13 | -2.39 | 13.05 | 24.2 | 11.17 |
| Targ 52 | 0 | 0.03 | 0.03 | 10.4 | 9.26 | -1.14 | 15.32 | 17.72 | 2.40 |
| Targ 53 | 0.1 | 0.17 | 0.07 | 10 | 9.87 | -0.13 | 19.37 | 19.12 | -0.25 |
| Targ 54 | 0.1 | 0.11 | 0.01 | 9.10 | 5.95 | -3.1515 | 18.54 | 20.84 | 2.30 |
| Targ 55 | 0 | 0 | 0 | 6.89 | 2.87 | -4.02 | 20.18 | 13.75 | -6.43 |
| Targ 58 | 0.14 | 0.08 | -0.06 | 14.09 | 14.2 | 0.11 | 18.15 | 22 | 3.85 |
| Targ 59 | 0.09 | 0.12 | 0.03 | 9.06 | 5.41 | -3.65 | 22.01 | 21.42 | -0.59 |
| Targ 62 | 0 | 0.1 | 0.1 | 3.51 | 5.43 | 1.92 | 9.15 | 13.1 | 3.95 |
| Mean | 0.054 | 0.081 | 0.028 | 8.82 | 7.27 | -1.56 | 16.97 | 19.02 | 2.05 |
| STD | 0.059 | 0.055 | 0.048 | 3.06 | 3.61 | 2.10 | 4.22 | 3.95 | 4.99 |
| Within group | 0.147 | | | 0.0739 | | | 0.284 | | |

*Fig. 30B*

DEXMECA

| | MP base | MP treat | MP diff | IMP base | IMP treat | IMP diff | SA base | SA treat | SA diff |
|---|---|---|---|---|---|---|---|---|---|
| Targ 36 | 49.06 | 60.21 | 11.15 | 9.31 | 13.68 | 4.37 | 3.85 | 4.45 | 0.6 |
| Targ 37 | 34.95 | 38.66 | 3.71 | 14.4359 | 15.65 | 1.2141 | 6.43 | 4.67 | -1.76 |
| Targ 41 | 35.5 | 36.51 | 1.01 | 7.05 | 5.53 | -1.52 | 3.29 | 0.96 | -2.33 |
| Targ 40 | 62.03 | 45.72 | -16.31 | 20.45 | 13.59 | -6.86 | 9.83 | 2.86 | -6.97 |
| Targ 46 | 45.98 | 41.67 | -4.31 | 13.51 | 12.3 | -1.21 | 4.42 | 4.26 | -0.16 |
| Targ 42 | 42.3 | 46.44 | 4.14 | 10.04 | 16.38 | 6.34 | 0.88 | 5.08 | 4.2 |
| Targ 45 | 64.55 | 47.06 | -17.49 | 25.73 | 11.2 | -14.53 | 8.12 | 4.87 | -3.25 |
| Targ 47 | 56.22 | 43.49 | -12.73 | 13.13 | 12.31 | -0.82 | 6.72 | 5.12 | -1.6 |
| Targ 48 | 99.21 | 77.04 | -22.16 | 39.63 | 29.36 | -10.27 | 20.52 | 13.76 | -6.76 |
| Mean | 54.42 | 48.53 | -5.89 | 17.03 | 14.44 | -2.59 | 7.12 | 5.11 | -2.00 |
| STD | 19.85 | 12.64 | 11.66 | 10.25 | 6.41 | 6.79 | 5.70 | 3.51 | 3.50 |

Within Group  0.168                0.286                0.124

Fig. 30D

Control

| | base | treat | diff | base | treat | diff | base | treat | diff |
|---|---|---|---|---|---|---|---|---|---|
| Targ 38 | 50.49 | 49.10 | -1.39 | 11.65 | 9.37 | -2.28 | 4.13 | 4.24 | 0.11 |
| Targ 52 | 45.94 | 31.19 | -14.74 | 16.13 | 18.23 | 2.1 | 5.73 | 8.96 | 3.23 |
| Targ 53 | 57.11 | 51.55 | -5.56 | 10.99 | 15.9 | 4.91 | 0.98 | 6.03 | 5.05 |
| Targ 54 | 42.46 | 43.07 | 0.61 | 10.99 | 9.75 | -1.24 | 1.89 | 3.8 | 1.91 |
| Targ 55 | 49.38 | 36.79 | -12.58 | 9.51 | 8.65 | -0.86 | 2.62 | 5.78 | 3.16 |
| Targ 58 | 50.77 | 48.44 | -2.33 | 22.16 | 20.05 | -2.11 | 8.07 | 5.84 | -2.23 |
| Targ 59 | 51.33 | 49.65 | -1.67 | 11.71 | 10.09 | -1.63 | 2.65 | 4.67 | 2.02 |
| Targ 62 | 15.19 | 22.76 | 7.57 | 6.02 | 9.06 | 3.04 | 2.51 | 3.63 | 1.12 |
| Mean | 45.33 | 41.57 | -3.76 | 12.40 | 12.64 | 0.24 | 3.57 | 5.37 | 1.80 |
| STD | 12.90 | 10.39 | 7.18 | 4.83 | 4.65 | 2.72 | 2.32 | 1.73 | 2.21 |

Within Group  0.182                 0.809                0.0548

Between Groups  MP 0.6626  IMP 0.289   SA ** 0.0187

Fig. 30E

|  | DEXMECA | | Bcomp |
|---|---|---|---|
|  | base | treat | diff |
| Targ 36 | 0.26 | 0.29 | 0.030 |
| Targ 37 | 0.36 | 0.14 | -0.220 |
| Targ 41 | 0.13 | 0.13 | 0.005 |
| Targ 40 | 0.09 | 0.26 | 0.175 |
| Targ 46 | 0.09 | 0.09 | 0.002 |
| Targ 42 | 0.08 | 0.13 | 0.054 |
| Targ 45 | 0.08 | 0.07 | -0.015 |
| Targ 47 | 0.04 | 0.06 | 0.015 |
| Targ 48 | 0.02 | 0.05 | 0.025 |
| Mean | 0.128 | 0.136 | 0.008 |
| STD | 0.111 | 0.088 | 0.102 |
|  | Within Group | | 0.823 |

Fig. 30F

| Control | base | treat | diff |
|---|---|---|---|
| Targ 38 | 0.30 | 0.06 | 0.24 |
| Targ 52 | 0.28 | 0.17 | 0.11 |
| Targ 53 | 0.09 | 0.18 | -0.09 |
| Targ 54 | 0.12 | 0.11 | 0.01 |
| Targ 55 | 0.17 | 0.23 | -0.06 |
| Targ 58 | 0.23 | 0.13 | 0.1 |
| Targ 59 | 0.07 | 0.06 | 0.01 |
| Targ 62 | 0.10 | 0.13 | -0.03 |
| Mean | 0.17 | 0.134 | 0.0363 |
| STD | 0.090 | 0.059 | 0.108 |
| Within Group | 0.375 | | |
| Between Group | Bcomp | 0.586 | |

Fig. 30G

METHOD OF TREATING BLADDER DISORDERS

CROSS REFERENCE TO RELATED APPLICATIONS

This application claims priority to U.S. Provisional Patent Application Ser. No. 61/614,892, filed 23 Mar. 2012 and U.S. Provisional Patent Application Ser. No. 61/696,097, filed 31 Aug. 2012, each of which is herein incorporated by reference in its entirety.

FIELD OF THE INVENTION

The present invention relates to exo-5-mecamylamine and the use of exo-S-mecamylamine in medical treatments.

BACKGROUND OF THE INVENTION

Overactive bladder (OAB) is a syndrome characterized by symptoms of "urgency with or without urge incontinence, usually with frequency and nocturia," where urgency is defined as "the complaint of a sudden compelling desire to pass urine which is difficult to defer." (Abrams et al., *The standardization of terminology of lower urinary tract function: report from the Standardization Subcommittee of the International Continence Society*, Neurourol. Urodyn. 21:167-178, 2002). OAB is one of several bladder diseases and may also be characterized by urge incontinence, detrusor instability, detrusor hyperreflexia, irritable bladder, spasmodic bladder, unstable bladder, incontinence—urge, or bladder spasms. OAB often presents itself as a strong, sudden need to urinate due to bladder spasms or contractions that can lead to frequent urination, in the daytime and at night, loss of urine (leaking) without meaning to urinate, and the sudden and urgent need to urinate (urinary urgency). Proper bladder control, therefore, requires the lower urinary tract and nervous system to work together to allow for the feeling and ability to respond to the urge to urinate at appropriate intervals, while minimizing leaking and urinary urgency.

The process of urination involves two phases: (i) filling and storage; and (ii) emptying. For the bladder to fill and store urine, the sphincter muscle (which controls the flow of urine out of the body) and bladder wall muscle (detrusor) must work together under nervous system control. During the filling and storage phase, the nervous system provides signals instructing the bladder to fill, and the bladder stretches so it can hold more urine. A typical human bladder holds anywhere from about 350 milliliters (ml) to about 550 ml of urine. A healthy adult human may, for example, feel the need to urinate when there is about 200 ml or more of urine in the bladder. The nervous system then provides signals instructing the bladder to empty. During the emptying phase, the detrusor muscle contracts and the sphincter muscle relaxes, working together to force urine out of the bladder, through the urinary tract, and out of the body.

Proper bladder control and control over urination frequency is part of normal childhood development. An infant's bladder automatically contracts when a certain amount of urine has collected in the bladder. As the child grows older and learns to control urination, part of the brain (cerebral cortex) helps prevent bladder muscle contractions. This allows for proper bladder control to delay urination until the child is ready to use the bathroom.

Disease states and advanced age, however, can alter a person's ability to control the bladder and urination frequency. The prevalence of OAB increases with age and is difficult to determine owing to the attached stigma, which may prevent patients from seeking medical care. OAB is estimated to affect 17% of the adult population in the United States and is ranked among the ten most common medical conditions. (Milson et al., *The prevalence of overactive bladder*, Am. J. Manag. Care 6 (11 suppl.):5565-573, 2000; Milson et al., *How widespread are the symptoms of an overactive bladder and how are they managed? A population-based prevalence study*, Br. J. Urol. Int. 87:760-66, 2001).

For example, a person's bladder may contract too often from nervous system (neurological) stimulation or bladder irritation, or a person suffering from OAB may leak urine because the bladder muscles contract at the wrong times. Often these contractions occur regardless of how much urine is in the bladder. OAB may have a variety of etiologies, some of which may not be true underlying causes of the disorder but nonetheless contribute to presentation of symptoms, including but not limited to bladder cancer, bladder inflammation, bladder outlet obstruction, bladder stones, infection, nervous system diseases (such as multiple sclerosis), nervous system injuries (such as stroke), and in men, urge incontinence also may be due to bladder changes caused by benign prostatic hypertrophy (BPH) or bladder outlet obstruction from an enlarged prostate. In many other cases, however, no cause can be found for OAB.

There are three main treatment approaches for OAB: medication, retraining, and surgery. Current medications used to treat OAB may relax bladder contractions to help improve bladder function. There are several types of medications that may be used alone or together. Anticholinergic medicines are reported to help relax the muscles of the bladder. These include oxybutynin (Oxytrol®, Ditropan®), tolterodine (Detrol®), darifenacin (Enablex®), trospium (Sanctura®), solifenacin (Vesicare®), and fesoterodine (Toviaz®). All of these anticholinergic medicines are competitive muscarinic receptor antagonists, and muscarinic receptors play an important role in several major cholinergically mediated functions, including contractions of urinary bladder smooth muscle and stimulation of salivary secretion. A relatively high incidence of dry mouth and, to a lesser extent, constipation is known as a potentially limiting side effect of anti-muscarinic therapy in humans. In addition, one significant contraindication, however, is that people with narrow-angle glaucoma cannot use anti-muscarinic medications. Flavoxate (Urispas) is a drug that calms muscle spasms. Studies have shown, however, that flavoxate is not always effective at controlling symptoms of urge incontinence. Tricyclic antidepressants (imipramine, doxepin) have also been used to treat urge incontinence because of their ability to "paralyze" the bladder smooth muscle. Reported possible side effects include: blurred vision, dizziness, dry mouth, fatigue, insomnia, and nausea. Mirabegron (Myrbetriq®) is a beta-3 adrenergic agonist that relaxes the detrusor smooth muscle during the storage phase of the urinary bladder fill-void cycle. Hypertension is a significant side effect of mirabegron, which also demonstrated very limited efficacy in human clinical trials.

All of these medicines have demonstrated limited efficacy, and not all patients achieve acceptable therapeutic responses, resulting in a significant unmet medical need. These treatments are also associated with therapy limiting side effects, notably dry mouth, dry eyes, blurred vision, constipation, hypertension, and cognitive dysfunction. The majority of available medications are metabolized by the cytochrome P450 pathway potentially leading to drug-drug interactions, especially in the elderly where OAB is most common and in whom poly pharmacy is also common. The limited efficacy and significant incidence of adverse effects diminish the usefulness of these drugs; often patients stop taking these medications altogether. More than 70% of patients do not continue therapy beyond nine months. (NDC Health Corporation: Persistency Data, Atlanta NDC Health Corporation, 2000). Of those remaining on treatment, some patients take less than the optimal dosage to avoid the side effects. Alternative OAB medications are needed with different safety, metabolic, tolerability, and efficacy profiles. Mecamylamine (N,2,3,3-tetramethylbicyclo[2.2.1]heptan-2-amine hydrochloride), was developed and characterized by Merck & Co., Inc., as a ganglionic blocker with clinically significant hypotensive actions (Stone et al., *Chemistry and structure-activity relationships of mecamylamine and derivatives*, J. Med. Pharm. Chem., 5(4):665-690, 1962). Mecamylamine was sold under the tradename Inversine®. Depending on preferred naming convention, the chemical name for mecamylamine may also be N,2,3,3-tetramethylnorbornan-2-amine. Mecamylamine exists as a racemic mixture of enantiomers and can be obtained according to the methods and processes described in U.S. Pat. No. 5,986,142, incorporated herein by reference for its teaching regarding methods of producing mecamylamine.

Unique characteristics of mecamylamine, including oral efficacy for treating hypertension, rapid onset, long duration of action, and nearly complete absorption from the gastrointestinal tract, made the drug a more desirable alternative to the existing ganglionic blockers. The average total daily dose of Inversine® (mecamylamine hydrochloride) used to treat high blood pressure was 25 mg, usually administered in three divided doses. The safety/tolerability profile of mecamylamine in humans has been established during decades of clinical use as an antihypertensive agent. The most common adverse reactions to the marketed drug include constipation, orthostatic dizziness, urinary retention, and blurred vision.

Bladder contraction is primarily controlled by the autonomic nervous system with input from higher centers. Ganglion blockers, such as racemic mecamylamine, decrease bladder contraction and lead to urinary retention. Kaplan et al. reported that racemic Inversine® doses of 2.5 mg BID produced changes in bladder contractility in spinal cord injury subjects. (Kaplan et al., *Reduction of bladder contractility after alpha-adrenergic blockade and after ganglionic blockade*, Acta Neurol. Scandinav. 59, 172-77, 1979). However, Kaplan et al. also reported that racemic mecamylamine administration resulted in a decrease in bladder electric potential (amplitude of contraction), which would indicate incomplete bladder emptying.

U.S. Pat. No. 7,101,916, herein incorporated by reference, provides for a pharmaceutical composition that includes a therapeutically effective amount of exo-S-mecamylamine or a pharmaceutically acceptable salt thereof, substantially free of exo-R-mecamylamine, in combination with a pharmaceutically acceptable carrier, wherein the pharmaceutical composition is characterized by a higher overall therapeutic index than a substantially similar pharmaceutical composition comprising exo-R-mecamylamine substantially free of exo-5-mecamylamine. The medical conditions disclosed therein include but are not limited to substance addiction (involving nicotine, cocaine, alcohol, amphetamine, opiate, other psychostimulant and a combination thereof), aiding smoking cessation, treating weight gain associated with smoking cessation, hypertension, hypertensive crisis, herpes type I and II, Tourette's Syndrome and other tremors, cancer (such as small cell lung cancer), atherogenic profile, neuropsychiatric disorders (such as bipolar disorder, depression, anxiety disorder, panic disorder, schizophrenia, seizure disorders, Parkinson's disease and attention deficit hyperactivity disorder), chronic fatigue syndrome, Crohn's disease, autonomic dysreflexia, and spasmogenic intestinal disorders. OAB is not described or disclosed in U.S. Pat. No. 7,101,916. The patent discloses that exo-5-mecamylamine may be administered intravenously, intramuscularly, transdermally, intrathecally, orally or by bolus injection. The dosage of exo-5-mecamylamine for treating the identified diseases is described in a range of about 0.5 mg to about 1000 mg, depending on dosage form, and exo-5-mecamylamine may be administered one to four times per day. Examples include a dose of about 2.5 mg per day for adults with drug-resistant Tourette's Syndrome and 1 mg per day or less for a small child with mild ADHD.

Purified exo-5-mecamylamine and exo-R-mecamylamine can be obtained according to methods discussed in U.S. Pat. No. 7,101,916, and references cited therein, also incorporated herein by reference for their teaching regarding the production of purified mecamylamine enantiomers. Exo-S-mecamylamine may also be referred to as dexmecamylamine, S-mecamylamine, TC-5214, or (S)—N,2,3,3-tetramethyl-norbornan-2-amine, and includes a pharmaceutically acceptable salt thereof.

Dexmecamylamine is a use-dependent potent inhibitor of the α3 nicotinic receptor subtype (e.g., α3β2 and α3β4). Such receptors are expressed in the urothelium and regulate bladder smooth muscle contraction. (Beckel et al., *Expression of functional nicotinic acetylcholine receptors in rat urinary bladder epithelial cells*, Am. J. Physiol. Renal Physiol. 290: F103-110, 2006). Dexmecamylamine, however, has not been studied previously in a rat model related to urinary function.

There remains a need for effective treatment of OAB, with specific focus toward symptomatic relief, having an improved side effect and tolerability profile.

SUMMARY OF THE INVENTION

One aspect of the present invention includes a method of treating overactive bladder, the method comprising the administration of a therapeutically effective amount of dexmecamylamine or a pharmaceutically acceptable salt thereof, substantially free of exo-R-mecamylamine, to a subject with overactive bladder.

One aspect of the present invention includes a method of treating overactive bladder, wherein the administration of dexmecamylamine is sufficient to increase the micturition interval relative to baseline in the subject in need thereof.

One aspect of the present invention includes a method of treating overactive bladder, wherein the administration of dexmecamylamine is sufficient to increase the micturition interval by at least 10% relative to baseline in the subject in need thereof.

One aspect of the present invention includes a method of treating overactive bladder, wherein the administration of dexmecamylamine is sufficient to increase the micturition interval by at least 10% relative to baseline without significant detrimental changes in bladder contraction amplitude in the subject in need thereof.

One aspect of the present invention includes a method of treating overactive bladder, the method comprising the oral administration of dexmecamylamine or a pharmaceutically acceptable salt thereof in an amount from about 0.1 mg to about 2.0 mg BID, substantially free of exo-R-mecamylamine, to a subject with overactive bladder.

One aspect of the present invention includes a method of treating overactive bladder, wherein the oral administration of dexmecamylamine is sufficient to increase the micturition interval by at least 10% relative to baseline in the subject in need thereof.

One aspect of the present invention includes a method of treating overactive bladder, wherein the dexmecamylamine or a pharmaceutically acceptable salt thereof is orally administered in an amount of about 0.5 mg BID.

One aspect of the present invention includes a method of treating overactive bladder, wherein the dexmecamylamine or a pharmaceutically acceptable salt thereof is orally administered in an amount of about 1.0 mg BID.

One aspect of the present invention includes a method of treating overactive bladder, wherein the dexmecamylamine or a pharmaceutically acceptable salt thereof is orally administered in an amount of about 2.0 mg BID.

One aspect of the present invention includes a method of treating overactive bladder, wherein the dexmecamylamine or a pharmaceutically acceptable salt thereof is orally administered in tablet form.

One aspect of the present invention includes a method of treating overactive bladder, wherein the administration of dexmecamylamine or a pharmaceutically acceptable salt thereof is sufficient to increase mean voided volume per micturition relative to baseline.

One aspect of the present invention includes a method of treating overactive bladder, wherein the administration of dexmecamylamine or a pharmaceutically acceptable salt thereof is sufficient to increase mean voided volume per micturition by at least 10% relative to baseline.

One aspect of the present invention includes a method of treating overactive bladder, wherein the administration of dexmecamylamine or a pharmaceutically acceptable salt thereof is sufficient to increase bladder capacity relative to baseline.

One aspect of the present invention includes a method of treating overactive bladder, wherein the administration of dexmecamylamine or a pharmaceutically acceptable salt thereof is sufficient to increase bladder capacity by at least 10% relative to baseline.

One aspect of the present invention includes a method of treating overactive bladder, the method comprising the administration of a therapeutically effective amount of dexmecamylamine or a pharmaceutically acceptable salt thereof, substantially free of exo-R-mecamylamine, to a subject with overactive bladder, wherein the administration of dexmecamylamine is sufficient to achieve a reduction of at least 0.6 micturitions per twenty-four hours relative to baseline in the subject in need thereof. Another aspect includes such method resulting in a reduction of at least 0.8 micturitions per twenty-four hours relative to baseline. Another aspect includes such method resulting in a reduction of at least 1.0 micturitions per twenty-four hours relative to baseline. Another aspect includes such method resulting in a reduction of at least 1.2 micturitions per twenty-four hours relative to baseline. Another aspect includes such method resulting in a reduction of at least 1.4 micturitions per twenty-four hours relative to baseline.

One aspect of the present invention includes a method of treating overactive bladder, wherein the administration of dexmecamylamine is sufficient to achieve a reduction of at least 0.6 micturitions per twenty-four hours relative to baseline without inducing dry mouth in the subject in need thereof. Another aspect includes such method resulting in a reduction of at least 0.8 micturitions per twenty-four hours relative to baseline, without inducing dry mouth. Another aspect includes such method resulting in a reduction of at least 1.0 micturitions per twenty-four hours relative to baseline, without inducing dry mouth. Another aspect includes such method resulting in a reduction of at least 1.2 micturitions per twenty-four hours relative to baseline, without inducing dry mouth. Another aspect includes such method resulting in a reduction of at least 1.4 micturitions per twenty-four hours relative to baseline, without inducing dry mouth.

One aspect of the present invention includes a method of treating overactive bladder, wherein the administration of dexmecamylamine is sufficient to achieve a reduction of at least 0.6 micturitions per twenty-four hours relative to baseline without inducing constipation in the subject in need thereof. Another aspect includes such method resulting in a reduction of at least 0.8 micturitions per twenty-four hours relative to baseline, without inducing constipation. Another aspect includes such method resulting in a reduction of at least 1.0 micturitions per twenty-four hours relative to baseline, without inducing constipation. Another aspect includes such method resulting in a reduction of at least 1.2 micturitions per twenty-four hours relative to baseline, without inducing constipation. Another aspect includes such method resulting in a reduction of at least 1.4 micturitions per twenty-four hours relative to baseline, without inducing constipation.

One aspect of the present invention includes a method of treating overactive bladder, wherein the administration of dexmecamylamine is sufficient to achieve a reduction of at least 0.6 micturitions per twenty-four hours relative to baseline without inducing hypertension in the subject in need thereof. Another aspect includes such method resulting in a reduction of at least 0.8 micturitions per twenty-four hours relative to baseline, without inducing hypertension. Another aspect includes such method resulting in a reduction of at least 1.0 micturitions per twenty-four hours relative to baseline, without inducing hypertension. Another aspect includes such method resulting in a reduction of at least 1.2 micturitions per twenty-four hours relative to baseline, without inducing hypertension. Another aspect includes such method resulting in a reduction of at least 1.4 micturitions per twenty-four hours relative to baseline, without inducing hypertension.

One aspect of the present invention includes a method of treating overactive bladder, wherein the administration of dexmecamylamine is sufficient to achieve a reduction of at least 0.6 micturitions per twenty-four hours relative to baseline without inducing blurred vision in the subject in need thereof. Another aspect includes such method resulting in a reduction of at least 0.8 micturitions per twenty-four hours relative to baseline, without inducing blurred vision. Another aspect includes such method resulting in a reduction of at least 1.0 micturitions per twenty-four hours relative to baseline, without inducing blurred vision. Another aspect includes such method resulting in a reduction of at least 1.2 micturitions per twenty-four hours relative to baseline, without inducing blurred vision. Another aspect includes such method resulting in a reduction of at least 1.4 micturitions per twenty-four hours relative to baseline, without inducing blurred vision.

One aspect of the present invention includes a method of treating overactive bladder, wherein the administration of dexmecamylamine is sufficient to achieve a reduction of at least 0.6 micturitions per twenty-four hours relative to baseline without significant detrimental changes in bladder contraction amplitude in the subject in need thereof. Another aspect includes such method resulting in a reduction of at least 0.8 micturitions per twenty-four hours relative to baseline, without significant detrimental changes in bladder contraction amplitude. Another aspect includes such method resulting in a reduction of at least 1.0 micturitions per twenty-four hours relative to baseline, without significant detrimental changes in bladder contraction amplitude. Another aspect includes such method resulting in a reduction of at least 1.2 micturitions per twenty-four hours relative to baseline, without significant detrimental changes in bladder contraction amplitude. Another aspect includes such method resulting in a reduction of at least 1.4 micturitions per twenty-four hours relative to baseline, without significant detrimental changes in bladder contraction amplitude.

One aspect of the present invention includes a method of treating overactive bladder, the method comprising the oral administration of dexmecamylamine or a pharmaceutically acceptable salt thereof in an amount from about 0.1 mg to about 2.0 mg BID, substantially free of exo-R-mecamylamine, to the subject with overactive bladder, wherein the administration of dexmecamylamine is sufficient to achieve a reduction of at least 0.6 micturitions per twenty-four hours relative to baseline in the subject in need thereof. Another aspect includes such method resulting in a reduction of at least 0.8 micturitions per twenty-four hours relative to baseline. Another aspect includes such method resulting in a reduction of at least 1.0 micturitions per twenty-four hours relative to baseline. Another aspect includes such method resulting in a reduction of at least 1.2 micturitions per twenty-four hours relative to baseline. Another aspect includes such method resulting in a reduction of at least 1.4 micturitions per twenty-four hours relative to baseline.

One aspect of the present invention includes a method of treating overactive bladder, the method comprising the administration of a therapeutically effective amount of dexmecamylamine or a pharmaceutically acceptable salt thereof, substantially free of exo-R-mecamylamine, to a subject with overactive bladder, wherein the administration of dexmecamylamine is sufficient to achieve a reduction of at least 0.6 urge urinary incontinence episodes per twenty-four hours relative to baseline in the subject in need thereof. Another aspect includes such method resulting in a reduction of at least 0.8 urge urinary incontinence episodes per twenty-four hours relative to baseline. Another aspect includes such method resulting in a reduction of at least 1.0 urge urinary incontinence episodes per twenty-four hours relative to baseline. Another aspect includes such method resulting in a reduction of at least 1.2 urge urinary incontinence episodes per twenty-four hours relative to baseline. Another aspect includes such method resulting in a reduction of at least 1.4 urge urinary incontinence episodes per twenty-four hours relative to baseline.

One aspect of the present invention includes a method of treating overactive bladder, wherein the administration of dexmecamylamine is sufficient to achieve a reduction of at least 0.6 urge urinary incontinence episodes per twenty-four hours relative to baseline without inducing dry mouth in the subject in need thereof. Another aspect includes such method resulting in a reduction of at least 0.8 urge urinary incontinence episodes per twenty-four hours relative to baseline, without inducing dry mouth. Another aspect includes such method resulting in a reduction of at least 1.0 urge urinary incontinence episodes per twenty-four hours relative to baseline, without inducing dry mouth. Another aspect includes such method resulting in a reduction of at least 1.2 urge urinary incontinence episodes per twenty-four hours relative to baseline, without inducing dry mouth. Another aspect includes such method resulting in a reduction of at least 1.4 urge urinary incontinence episodes per twenty-four hours relative to baseline, without inducing dry mouth.

One aspect of the present invention includes a method of treating overactive bladder, wherein the administration of dexmecamylamine is sufficient to achieve a reduction of at least 0.6 urge urinary incontinence episodes per twenty-four hours relative to baseline without inducing constipation in the subject in need thereof. Another aspect includes such method resulting in a reduction of at least 0.8 urge urinary incontinence episodes per twenty-four hours relative to baseline, without inducing constipation. Another aspect includes such method resulting in a reduction of at least 1.0 urge urinary incontinence episodes per twenty-four hours relative to baseline, without inducing constipation. Another aspect includes such method resulting in a reduction of at least 1.2 urge urinary incontinence episodes per twenty-four hours relative to baseline, without inducing constipation. Another aspect includes such method resulting in a reduction of at least 1.4 urge urinary incontinence episodes per twenty-four hours relative to baseline, without inducing constipation.

One aspect of the present invention includes a method of treating overactive bladder, wherein the administration of dexmecamylamine is sufficient to achieve a reduction of at least 0.6 urge urinary incontinence episodes per twenty-four hours relative to baseline without inducing hypertension in the subject in need thereof. Another aspect includes such method resulting in a reduction of at least 0.8 urge urinary incontinence episodes per twenty-four hours relative to baseline, without inducing hypertension. Another aspect includes such method resulting in a reduction of at least 1.0 urge urinary incontinence episodes per twenty-four hours relative to baseline, without inducing hypertension. Another aspect includes such method resulting in a reduction of at least 1.2 urge urinary incontinence episodes per twenty-four hours relative to baseline, without inducing hypertension. Another aspect includes such method resulting in a reduction of at least 1.4 urge urinary incontinence episodes per twenty-four hours relative to baseline, without inducing hypertension.

One aspect of the present invention includes a method of treating overactive bladder, wherein the administration of dexmecamylamine is sufficient to achieve a reduction of at least 0.6 urge urinary incontinence episodes per twenty-four hours relative to baseline without inducing blurred vision in the subject in need thereof. Another aspect includes such method resulting in a reduction of at least 0.8 urge urinary incontinence episodes per twenty-four hours relative to baseline, without inducing blurred vision. Another aspect includes such method resulting in a reduction of at least 1.0 urge urinary incontinence episodes per twenty-four hours relative to baseline, without inducing blurred vision. Another aspect includes such method resulting in a reduction of at least 1.2 urge urinary incontinence episodes per twenty-four hours relative to baseline, without inducing blurred vision. Another aspect includes such method resulting in a reduction of at least 1.4 urge urinary incontinence episodes per twenty-four hours relative to baseline, without inducing blurred vision.

One aspect of the present invention includes a method of treating overactive bladder, wherein the administration of dexmecamylamine is sufficient to achieve a reduction of at least 0.6 urge urinary incontinence episodes per twenty-four hours relative to baseline without significant detrimental changes in bladder contraction amplitude in the subject in need thereof. Another aspect includes such method resulting in a reduction of at least 0.8 urge urinary incontinence episodes per twenty-four hours relative to baseline, without significant detrimental changes in bladder contraction amplitude. Another aspect includes such method resulting in a reduction of at least 1.0 urge urinary incontinence episodes per twenty-four hours relative to baseline, without significant detrimental changes in bladder contraction amplitude. Another aspect includes such method resulting in a reduction of at least 1.2 urge urinary incontinence episodes per twenty-four hours relative to baseline, without significant detrimental changes in bladder contraction amplitude. Another aspect includes such method resulting in a reduction of at least 1.4 urge urinary incontinence episodes per twenty-four hours relative to baseline, without significant detrimental changes in bladder contraction amplitude.

One aspect of the present invention includes a method of treating overactive bladder, the method comprising the oral administration of dexmecamylamine or a pharmaceutically acceptable salt thereof in an amount from about 0.1 mg to about 2.0 mg BID, substantially free of exo-R-mecamylamine, to the subject with overactive bladder, wherein the administration of dexmecamylamine is sufficient to achieve a reduction of at least 0.6 urge urinary incontinence episodes per twenty-four hours relative to baseline in the subject in need thereof. Another aspect includes such method resulting in a reduction of at least 0.8 urge urinary incontinence episodes per twenty-four hours relative to baseline. Another aspect includes such method resulting in a reduction of at least 1.0 urge urinary incontinence episodes per twenty-four hours relative to baseline. Another aspect includes such method resulting in a reduction of at least 1.2 urge urinary incontinence episodes per twenty-four hours relative to baseline. Another aspect includes such method resulting in a reduction of at least 1.4 urge urinary incontinence episodes per twenty-four hours relative to baseline.

One aspect of the present invention includes a method of treating overactive bladder, the method comprising the administration of a therapeutically effective amount of dexmecamylamine or a pharmaceutically acceptable salt thereof, substantially free of exo-R-mecamylamine, to a subject with overactive bladder. In one embodiment, the administration of dexmecamylamine is sufficient to increase the micturition interval relative to baseline in the subject in need thereof. In one embodiment, the administration of dexmecamylamine is sufficient to increase the micturition interval by at least 10% relative to baseline in the subject in need thereof. In one embodiment, the administration of dexmecamylamine is sufficient to increase the micturition interval by at least 10% relative to baseline without significant detrimental changes in bladder contraction amplitude in the subject in need thereof.

One aspect of the present invention includes a method of treating overactive bladder, the method comprising the oral administration of dexmecamylamine or a pharmaceutically acceptable salt thereof in an amount from about 0.1 mg to about 2.0 mg BID, substantially free of exo-R-mecamylamine, to a subject with overactive bladder. In one embodiment, the oral administration of dexmecamylamine is sufficient to increase the micturition interval by at least 10% relative to baseline in the subject in need thereof. In one embodiment, the dexmecamylamine or a pharmaceutically acceptable salt thereof is orally administered in an amount of about 0.5 mg BID. In one embodiment, the dexmecamylamine or a pharmaceutically acceptable salt thereof is orally administered in an amount of about 1.0 mg BID. In one embodiment, the dexmecamylamine or a pharmaceutically acceptable salt thereof is orally administered in an amount of about 2.0 mg BID. In one embodiment, the dexmecamylamine or a pharmaceutically acceptable salt thereof is orally administered in tablet form. In one embodiment, the administration of dexmecamylamine is sufficient to increase the micturition interval by at least 10% relative to baseline without significant detrimental changes in bladder contraction amplitude in the subject in need thereof.

As one embodiment of any aspect of the present invention, the administration of dexmecamylamine or a pharmaceutically acceptable salt thereof is sufficient to increase mean voided volume per micturition relative to baseline. As one embodiment of any aspect of the present invention, the administration of dexmecamylamine or a pharmaceutically acceptable salt thereof is sufficient to increase mean voided volume per micturition by at least 10% relative to baseline. As one embodiment of any aspect of the present invention, the administration of dexmecamylamine or a pharmaceutically acceptable salt thereof is sufficient to increase bladder capacity relative to baseline. As one embodiment of any aspect of the present invention, the administration of dexmecamylamine or a pharmaceutically acceptable salt thereof is sufficient to increase bladder capacity by at least 10% relative to baseline.

One aspect of the present invention includes a method of treating overactive bladder, the method comprising the administration of a therapeutically effective amount of dexmecamylamine or a pharmaceutically acceptable salt thereof, substantially free of exo-R-mecamylamine, to a subject with overactive bladder, wherein the administration of dexmecamylamine is sufficient to achieve a reduction of at least about 0.6 micturitions per twenty-four hours relative to baseline in the subject in need thereof. In one embodiment, the administration of dexmecamylamine is sufficient to achieve a reduction of at least about 0.8 micturitions per twenty-four hours relative to baseline without inducing dry mouth in the subject in need thereof. In one embodiment, the administration of dexmecamylamine is sufficient to achieve a reduction of at least about 1.0 micturitions per twenty-four hours relative to baseline in the subject in need thereof. In one embodiment, the administration of dexmecamylamine is sufficient to achieve a reduction of at least about 1.2 micturitions per twenty-four hours relative to baseline in the subject in need thereof. In one embodiment, the administration of dexmecamylamine is sufficient to achieve a reduction of at least about 1.4 micturitions per twenty-four hours relative to baseline in the subject in need thereof.

One aspect of the present invention includes a method of treating overactive bladder, the method comprising the administration of a therapeutically effective amount of dexmecamylamine or a pharmaceutically acceptable salt thereof, substantially free of exo-R-mecamylamine, to a subject with overactive bladder, wherein the administration of dexmecamylamine is sufficient to achieve a reduction of at least about 0.6 urge urinary incontinence episodes per twenty-four hours relative to baseline in the subject in need thereof. In one embodiment, the administration of dexmecamylamine is sufficient to achieve a reduction of at least about 0.8 urge urinary incontinence episodes per twenty-four hours relative to baseline. In one embodiment, the administration of dexmecamylamine is sufficient to achieve a reduction of at least about 1.0 urge urinary incontinence episodes per twenty-four hours relative to baseline in the subject in need thereof. In one embodiment, the administration of dexmecamylamine is sufficient to achieve a reduction of at least about 1.2 urge urinary incontinence episodes per twenty-four hours relative to baseline in the subject in need thereof. In one embodiment, the administration of dexmecamylamine is sufficient to achieve a reduction of at least about 1.4 urge urinary incontinence episodes per twenty-four hours relative to baseline in the subject in need thereof.

One aspect of the present invention includes a method of treating overactive bladder in a subject, the method comprising the oral administration of dexmecamylamine or a pharmaceutically acceptable salt thereof in an amount from about 0.1 mg to about 2.0 mg BID, substantially free of exo-R-mecamylamine, to the subject with overactive bladder, wherein the administration of dexmecamylamine is sufficient to achieve a reduction of at least about 0.6 micturitions per twenty-four hours relative to baseline in the subject in need thereof. In one embodiment, the oral administration of dexmecamylamine is sufficient to achieve a reduction of at least about 0.8 micturitions per twenty-four hours relative to baseline in the subject in need thereof. In one embodiment, the oral administration of dexmecamylamine is sufficient to achieve a reduction of at least about 1.0 micturitions per twenty-four hours relative to baseline in the subject in need thereof. In one embodiment, the oral administration of dexmecamylamine is sufficient to achieve a reduction of at least about 1.2 micturitions per twenty-four hours relative to baseline in the subject in need thereof. In one embodiment, the oral administration of dexmecamylamine is sufficient to achieve a reduction of at least about 1.4 micturitions per twenty-four hours relative to baseline in the subject in need thereof. In one embodiment, the dexmecamylamine or a pharmaceutically acceptable salt thereof is orally administered in an amount of about 0.5 mg BID. In one embodiment, the dexmecamylamine or a pharmaceutically acceptable salt thereof is orally administered in an amount of about 1.0 mg BID. In one embodiment, the dexmecamylamine or a pharmaceutically acceptable salt thereof is orally administered in an amount of about 2.0 mg BID. In one embodiment, the dexmecamylamine or a pharmaceutically acceptable salt thereof is orally administered in tablet form.

One aspect of the present invention includes a method of treating overactive bladder in a subject, the method comprising the oral administration of dexmecamylamine or a pharmaceutically acceptable salt thereof in an amount from about 0.1 mg to about 2.0 mg BID, substantially free of exo-R-mecamylamine, to the subject with overactive bladder, wherein the administration of dexmecamylamine is sufficient to achieve a reduction of at least about 0.6 urge urinary incontinence episodes per twenty-four hours relative to baseline in the subject in need thereof. In one embodiment, the oral administration of dexmecamylamine is sufficient to achieve a reduction of at least about 0.8 urge urinary incontinence episodes per twenty-four hours relative to baseline in the subject in need thereof. In one embodiment, the oral administration of dexmecamylamine is sufficient to achieve a reduction of at least about 1.0 urge urinary incontinence episodes per twenty-four hours relative to baseline in the subject in need thereof. In one embodiment, the oral administration of dexmecamylamine is sufficient to achieve a reduction of at least about 1.2 urge urinary incontinence episodes per twenty-four hours relative to baseline in the subject in need thereof. In one embodiment, the oral administration of dexmecamylamine is sufficient to achieve a reduction of at least about 1.4 urge urinary incontinence episodes per twenty-four hours relative to baseline in the subject in need thereof. In one embodiment, the dexmecamylamine or a pharmaceutically acceptable salt thereof is orally administered in an amount of about 0.5 mg BID. In one embodiment, the dexmecamylamine or a pharmaceutically acceptable salt thereof is orally administered in an amount of about 1.0 mg BID. In one embodiment, the dexmecamylamine or a pharmaceutically acceptable salt thereof is orally administered in an amount of about 2.0 mg BID. In one embodiment, the dexmecamylamine, or a pharmaceutically acceptable salt thereof is orally administered in tablet form.

One aspect of the present invention includes a method of treating overactive bladder in a human.

The scope of the present invention includes methods, uses, compound for use, compound for treating overactive bladder, as well as uses of compound for the manufacture of a medicament for treating overactive bladder. The scope of the present invention is intended to encompass such inventions regardless of particular claim format.

The scope of the present invention includes all combinations of aspects, embodiments, and preferences herein described.

BRIEF DESCRIPTION OF THE FIGURES

FIG. 1 illustrates a hypothetical model of nicotinic cholinergic signaling in the urothelium disclosed in Beckel et al., *Expression of functional nicotinic acetylcholine receptors in rat urinary bladder epithelial cells*, Am. J. Physiol. Renal Physiol. 290:F103-110, 2006.

FIG. 2 depicts the cystometry for the intravesical model of conscious rats.

FIG. 6 illustrates a comparative tabular summary of the OAB assay performed by UROSphere versus the Beckel et al. study assays.

FIG. 8 illustrates that dexmecamylamine (TC-5214 and TI-11179 in the figure) demonstrates a statistically significant increase in inter-contraction interval (ICI)

FIG. 9 illustrates that dexmecamylamine (TC-5214 and TI-11179 in the figure) demonstrates a statistically significant increase in bladder capacity (BC).

FIG. 10 illustrates that dexmecamylamine (TC-5214 and TI-11179 in the figure) demonstrates a statistically significant decrease in micturition frequency (MF).

FIG. 11 illustrates that dexmecamylamine (TC-5214 and TI-11179 in the figure) demonstrates no change in bladder contraction amplitude (AM).

FIG. 12 presents the ICI data reanalyzed using median values and demonstrates the effects of intravesically administered hexamethonium and dexmecamylamine (TC-5214) on bladder function in anesthetized animals.

FIG. 13 illustrates the settings for the electrophysiology system used to measure $\alpha3\beta4$ function.

FIG. 24 is a table showing rates of urinary tract infection and urinary retention in human patients administered dexmecamylamine in a clinical trial.

FIGS. 30A-30G show tabulated data for bladder activity after administration of dexmecamylamine.

DETAILED DESCRIPTION OF THE INVENTION

Figure 3:
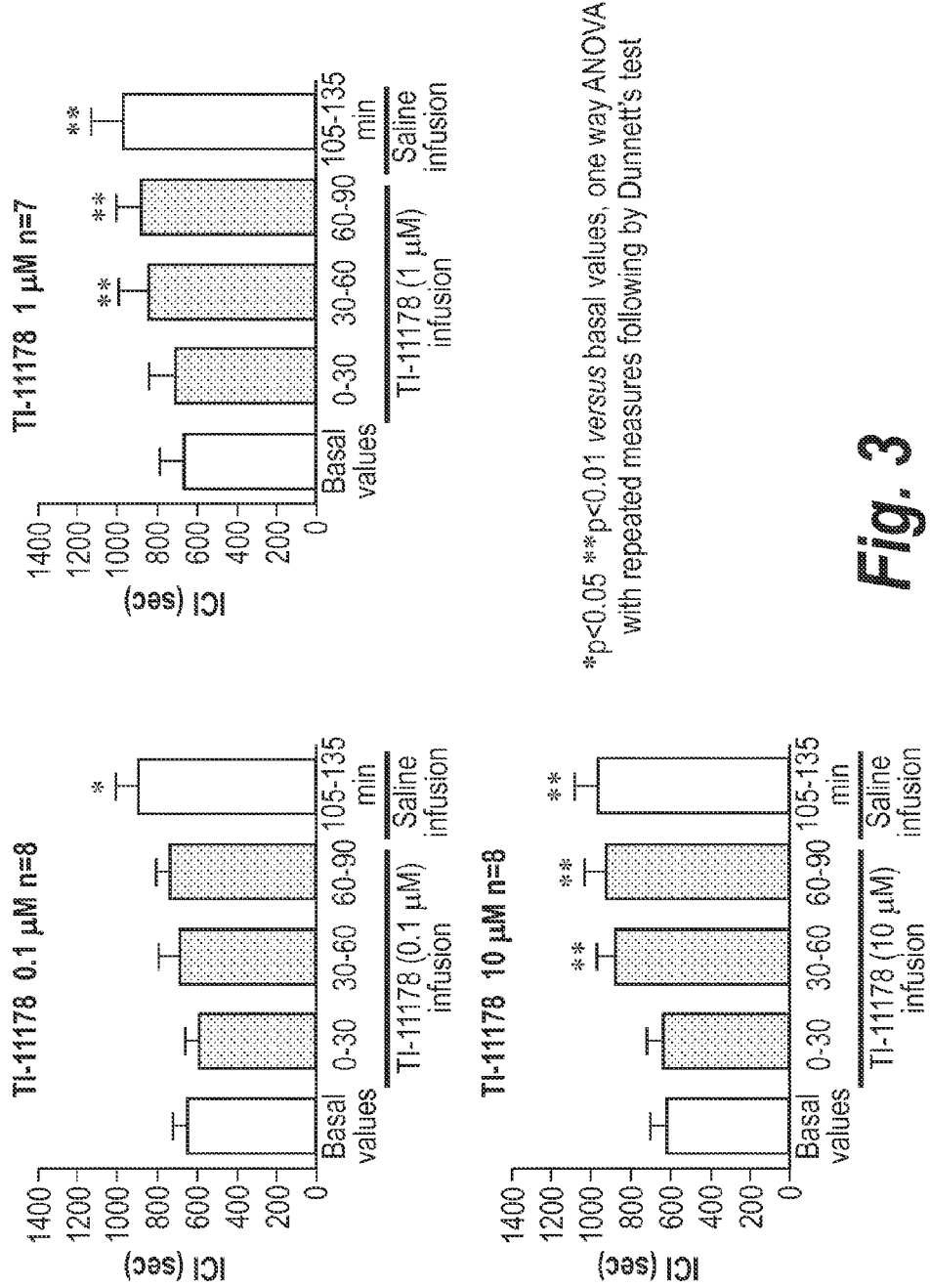
FIG. 3 illustrates the effects of dosing exo-R-mecamylamine (also referred to as TC-5213 and as TI-11178 in the figure), at doses of 0.1, 1, and 10 μM.

Dexmecamylamine is a selective nicotinic acetylcholine receptor (nAChR) channel modulator. While the precise molecular targets associated with effects on the bladder are still under investigation, dexmecamylamine functionally interacts with human α4β2, α3β2, and α3β4 nicotinic receptors and the known interactions of dexmecamylamine with α3-containing nicotinic receptors suggests it is likely to prove beneficial in the treatment of OAB. Nonclinical studies with dexmecamylamine have been conducted to evaluate the potential for treatment in OAB, and clinical studies using dexmecamylamine for treating OAB are being proposed.

It has now been found that because dexmecamylamine is excreted almost entirely unchanged in the urine, dexmecamylamine reaches higher concentrations in the urine compared to the plasma. The exposure differential results in the ability of dexmecamylamine to target local nicotinic receptors in the urothelium that affect bladder contraction frequency while limiting systemic side effects. Consequently, the potential for dexmecamylamine to treat OAB through its action on nAChRs in the bladder urothelium warrants further investigation.

More recently, dexmecamylamine was evaluated as adjunctive therapy in the treatment of major depressive disorder (MDD) in a large international Phase 3 depression program. Although dexmecamylamine failed to demonstrate efficacy in the treatment of depression, the compound proved to be well tolerated at doses up to and including the top dose evaluated, 4 mg twice daily (BID). More than 2400 subjects have received dexmecamylamine in double-blind or open-label studies.

No safety studies using dexmecamylamine have been performed in OAB. Phase 2 and Phase 3 clinical studies using dexmecamylamine in Major Depressive Disorder (MDD) have been conducted and completed. Dexmecamylamine was generally safe and well-tolerated in these studies. Briefly, in the fixed dose Phase 3 studies in MDD, at doses of 2 mg BID (the maximum doses to be studied in the OAB study), the most frequent treatment emergent adverse events that were reported more than 2% more commonly in the dexmecamylamine group compared to placebo group were: constipation (15.2% dexmecamylamine vs. 3.8% placebo); and dry mouth (7.0% dexmecamylamine vs. 1.3% placebo). There were no noteworthy differences in any measurements of vital signs, blood or urine laboratory measurements, ECG conduction intervals, or suicidality. In these fixed dose studies, the treatment emergent adverse events reported for doses less than 2 mg BID are similar to placebo.

Additional pre-clinical studies on mecamylamine and its stereoisomers have demonstrated that dexmecamylamine provides a superior safety profile over mecamylamine and its R-isomer (see U.S. Pat. No. 7,101,916), but there have not been any previously published pre-clinical or clinical studies using dexmecamylamine to treat OAB or to assess the safety and efficacy profile for the OAB indication. Pre-clinical in vivo studies in rat models described herein support the safety and efficacy of using dexmecamylamine, substantially free of exo-R-mecamylamine, to treat OAB in humans with a favorable side effect profile. In short, it is unexpected that administration of relatively low systemic doses of dexmecamylamine, substantially free of exo-R-mecamylamine, in human patients will result in the safe and efficacious treatment of OAB.

Unless stated otherwise, the following terms and phrases as used herein are intended to have the following meanings. The fact that a particular term or phrase is not specifically defined should not be correlated to indefiniteness or lacking clarity, but rather terms herein are used within their ordinary meaning. When trade names are used herein, applicants intend to independently include the tradename product and the active pharmaceutical ingredient(s) of the tradename product.

For reference herein, "dexmecamylamine substantially free of exo-R-mecamylamine" includes dexmecamylamine in amounts greater than or equal to 95% by weight and exo-R-mecamylamine 5% or less by weight. More preferably, "dexmecamylamine substantially free of exo-R-mecamylamine" includes dexmecamylamine greater than or equal to 98% by weight and exo-R-mecamylamine 2% or less by weight. More preferably, "dexmecamylamine substantially free of exo-R-mecamylamine" includes dexmecamylamine greater than or equal to 99% by weight and exo-R-mecamylamine 1% or less by weight. Even more preferably, "dexmecamylamine substantially free of exo-R-mecamylamine" includes exo-5-mecamylamine greater than or equal to 99.5% by weight and exo-R-mecamylamine 0.5% or less by weight. Most preferably, "dexmecamylamine substantially free of exo-R-mecamylamine" includes exo-s-mecamylamine greater than or equal to 99.7% by weight and exo-R-mecamylamine 0.3% or less by weight.

As used herein, the term "pharmaceutically acceptable" refers to carrier(s), diluent(s), excipient(s) or salt forms of the compound of the present invention that are compatible with the other ingredients of the formulation and not deleterious to the recipient of the pharmaceutical composition.

As used herein, the term "pharmaceutical composition" refers to the compound of the present invention optionally in combination with one or more pharmaceutically acceptable carriers, diluents, or excipients. Pharmaceutical compositions preferably exhibit a degree of stability to environmental conditions so as to make them suitable for manufacturing and commercialization purposes.

As used herein, the terms "effective amount", "therapeutically effective amount", and "effective dose" refer to an amount of the compound of the present invention sufficient to elicit the desired pharmacological or therapeutic effects, thus resulting in an effective treatment of a bladder disorder. Treatment of a bladder disorder may be manifested by delaying or preventing the onset or progression of the disorder, as well as the onset or progression of symptoms associated with the disorder. Treatment of a bladder disorder may also be manifested by a decrease or elimination of symptoms, reversal of the progression of the disorder, as well as any other contribution to the well-being of the patient.

As used herein, the terms "micturition" and "urination" refer to the ejection of urine from the bladder through the urethra. The terms "micturition interval" (MI) and "inter-contraction interval" (ICI) refer to the time interval between two consecutive micturitions. The term "bladder contraction amplitude" is defined as the difference between bladder pressure, at the peak of bladder contraction (maximum bladder pressure), minus baseline bladder pressure. The term "micturition pressure" refers to bladder pressure during micturition, including but not limited to threshold bladder pressure necessary to evoke a bladder contraction and/or maximum bladder pressure during micturition or both.

In certain embodiments, the administration of dexmecamylamine, substantially free of exo-R-mecamylamine, can eliminate, ameliorate, reduce, relieve, or treat one or more symptoms of overactive bladder, including frequency of urination, urgency of urination, occurrences of nocturia, and occurrences of incontinence. For example, in certain embodiments, the methods of the invention can provide about 10% reduction in the number of mean daily micturitions, e.g., a reduction of about 1 micturition per day. In other embodiments, the methods of the invention can provide reduced sensations of urgency, e.g., through inhibition of α3 receptors in the urothelium or other afferent bladder associated nerves, diminishing bladder contraction, and/or affecting afferent signaling to the brain (via P2X), thereby reducing and/or blocking the sensation of urgency. In other embodiments the methods of the invention can increase bladder capacity and/or micturition interval without significant detrimental changes in micturition pressure or bladder contraction amplitude. In further embodiments, the methods of the invention can provide a reduction in occurrences of nocturia, reducing night time urination to 1 or less events per night, e.g., by maintaining a therapeutic concentration during night hours through a once daily or BID dosing regimen. In still other embodiments, the methods of the invention can provide a reduction in occurrences of urinary incontinence, e.g., about a 20-25% mean reduction in the number of episodes of urinary incontinence would translate to a reduction of about 1 episode per day.

The effective dose for overactive bladder can vary, depending upon factors such as the condition of the patient, the severity of the symptoms of the disorder, and the manner in which the pharmaceutical composition is administered. To be administered in an effective dose, compounds may be administered in an amount of as low as about 0.1 mg to about 4 mg; in certain embodiments, about 0.25 mg to 2 mg; in certain embodiments, about 0.5 mg to about 1 mg. Thus, an effective dose typically represents the amount that may be administered as a single dose, or as one or more doses that may be administered over a 24 hours period. The dose may be once daily or may be divided so as to provide twice daily (BID), three times a day (QD), four times a day (QID), or more doses.

In certain embodiments of the present invention an effective dose is about 0.25 mg, 0.5 mg, about 1 mg, or about 2 mg, as free base equivalents, twice daily, orally.

In certain embodiments, one or more of the dosage strengths may include an optional aesthetic film coating, such as 5.4 mg of Opadry® 03B 150008 Red per tablet for a non-functional film coat.

The present invention includes a salt or solvate of the compounds herein described, including combinations thereof such as a solvate of a salt. The compounds may exist in solvated, for example hydrated, as well as unsolvated forms, and the present invention encompasses all such forms. Typically, but not absolutely, the salts of the present invention are pharmaceutically acceptable salts. Salts encompassed within the term "pharmaceutically acceptable salts" refer to nontoxic salts of the compounds of this invention. Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates. In certain embodiments, S-mecamylamine hydrochloride is a preferential salt form.

Although it is possible to administer the compound of the present invention in the form of a bulk active chemical, it is preferred to administer the compound in the form of a pharmaceutical composition or formulation. Thus, one aspect the present invention includes pharmaceutical compositions comprising dexmecamylamine and/or pharmaceutically acceptable salts thereof and one or more pharmaceutically acceptable carriers, diluents, or excipients. Another aspect of the invention provides a process for the preparation of a pharmaceutical composition including admixing dexmecamylamine and/or pharmaceutically acceptable salts thereof with one or more pharmaceutically acceptable carriers, diluents or excipients.

The manner in which the compound of the present invention is administered can vary. The compound of the present invention is preferably administered orally. Preferred pharmaceutical compositions for oral administration include tablets, capsules, caplets, syrups, solutions, and suspensions.

One embodiment of an oral pharmaceutical composition includes about 0.6 mg S-mecamylamine hydrochloride; about 6.1 mg microcrystalline cellulose, grade I; about 102.5 mg microcrystalline cellulose, grade II; about 6.0 mg hydroxypropyl cellulose; about 3.6 mg croscarmellose sodium; about 0.6 mg colloidal silicon dioxide; and about 0.6 mg magnesium.

One embodiment of a pharmaceutical composition includes about 1.2 mg S-mecamylamine hydrochloride; about 12.2 mg microcrystalline cellulose, grade I; about 95.8 mg microcrystalline cellulose, grade II; about 6.0 mg hydroxypropyl cellulose; about 3.6 mg croscarmellose sodium; about 0.6 mg colloidal silicon dioxide; and about 0.6 mg magnesium.

One embodiment of a pharmaceutical composition includes about 2.4 mg S-mecamylamine hydrochloride; about 24.4 mg microcrystalline cellulose, grade I; about 82.4 mg microcrystalline cellulose, grade II; about 6.0 mg hydroxypropyl cellulose; about 3.6 mg croscarmellose sodium; about 0.6 mg colloidal silicon dioxide; and about 0.6 mg magnesium.

One embodiment for manufacture includes blending and sieving the excipients as is known in the art.

The pharmaceutical compositions can also be administered via injection, namely, intravenously, intramuscularly, subcutaneously, intraperitoneally, intraarterially, intrathecally, and intracerebroventricularly. Intravenous administration is a preferred method of injection. Suitable carriers for injection are well known to those of skill in the art and include 5% dextrose solutions, saline, and phosphate buffered saline.

The formulations may also be administered using other means, for example, rectal administration. Formulations useful for rectal administration, such as suppositories, are well known to those of skill in the art. The compounds can also be administered by inhalation, for example, in the form of an aerosol; topically, such as, in lotion form; transdermally, such as, using a transdermal patch (for example, by using technology that is commercially available from Novartis and Alza Corporation), by powder injection, or by buccal, sublingual, or intranasal absorption.

Pharmaceutical compositions may be formulated in unit dose form, or in multiple or subunit doses. The pharmaceutical compositions may be administered to a patient or subject such as a warm-blooded animal, for example, a mammal such as a mouse, rat, cat, rabbit, dog, pig, cow, or monkey; but advantageously is administered to a human being. In addition, the time of day (e.g., morning, evening, before bedtime) and the number of times per day (e.g., once per day, twice per day) that the pharmaceutical composition is administered can vary.

EXAMPLES

Example 1

Dexmecamylamine in OAB: Intravesical Model in Conscious Rats (1) In a first study (performed by UROsphere), female Sprague Dawley rats (200-270 g) from Charles River France, housed in 3-4 rats per cage were anesthetized with isoflurane (1.5-3%). Two days after cystometry, a polyethylene catheter was implanted in the bladder through the dome and exteriorized at the scapular level. Each rat was housed individually after surgery. The cystometry is depicted in FIG. 2. This is the first known experiment using the intravesical model in conscious rats to test dexmecamylamine for potential efficacy in treating OAB.

The effects of dosing exo-R-mecamylamine (also referred to as TC-5213 and as TI-11178), at doses of 0.1, 1, and 10 µM are depicted in FIG. 3.

Figure 4:
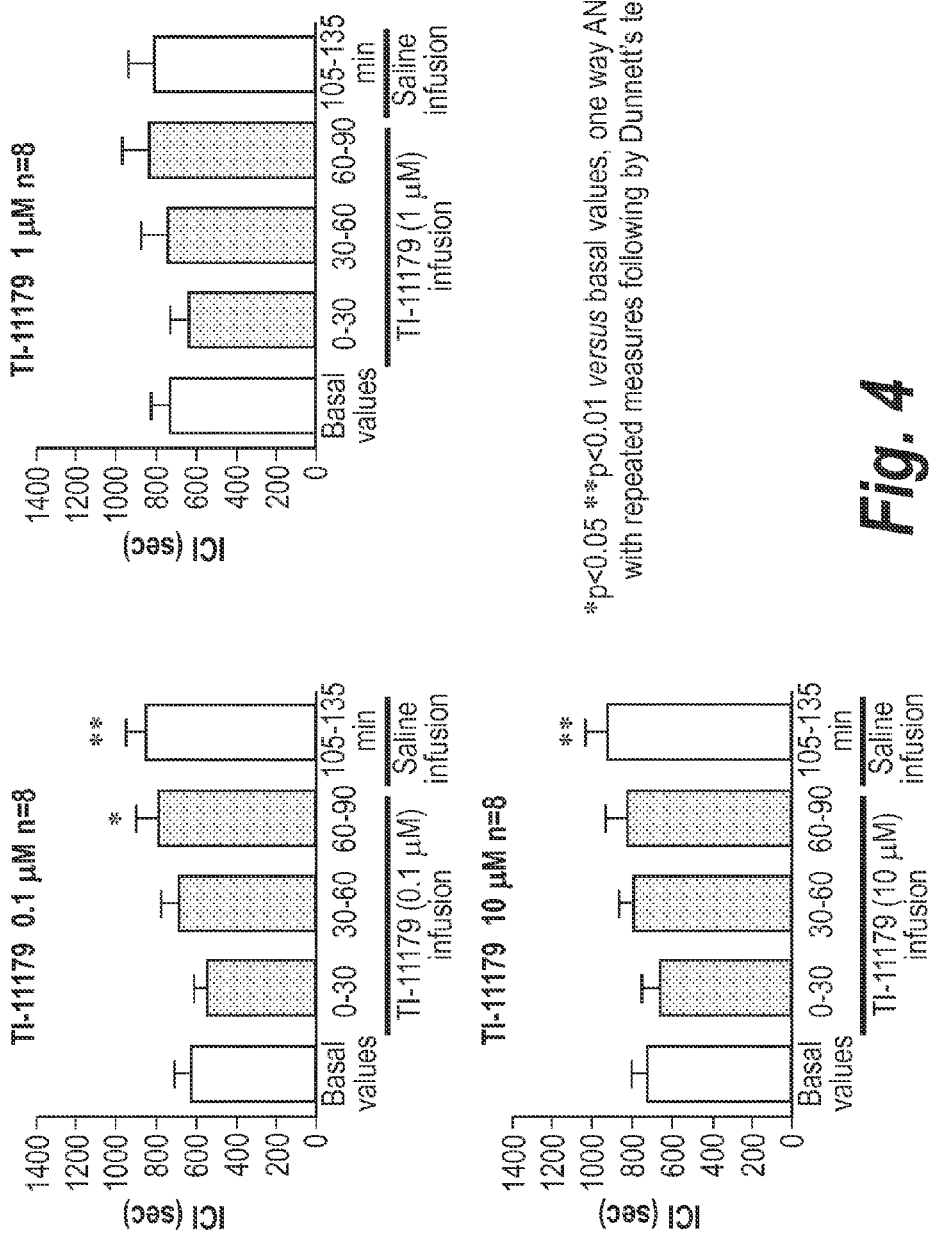
FIG. 4 illustrates the effects of dosing exo-5-mecamylamine (also referred to as dexmecamylamine, TC-5214, and as TI-11179 in the figure), at doses of 0.1, 1, and 10 μM.

The effects of dosing dexmecamylamine (also referred to as TC-5214 and as TI-11179), at doses of 0.1, 1, and 10 µM are depicted in FIG. 4.

Figure 5:
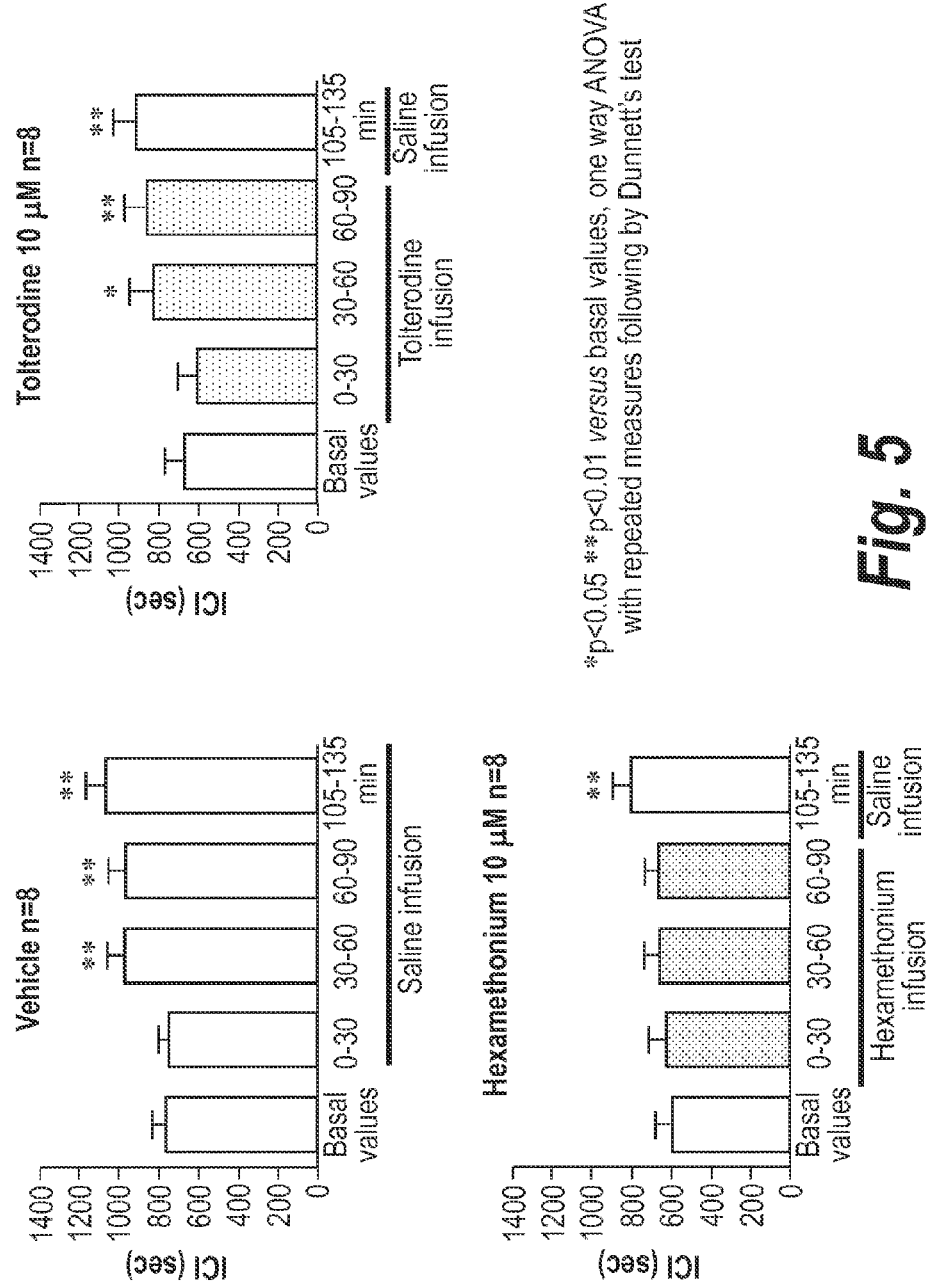
FIG. 5 illustrates the effects of dosing hexamethonium (10 μM) and tolterodine (10 μM).

The effects of dosing hexamethonium (10 µM) and tolterodine (10 µM) are depicted in FIG. 5.

(2) In a second dexmecamylamine study in conscious rats, approximately twelve female Sprague Dawley rats received either normal saline or 10 µM dexmecamylamine intravesically (rate of 10 mL/hr.) over a period of approximately 60 minutes, during which cystometric parameters including micturition frequency (MF), intercontraction interval and bladder capacity were recorded. Dexmecamylamine did not produce statistically significant changes in any of the cystometric parameters relative to baseline parameters. The results of the two dexmecamylamine studies are limited to intravesical administration of dexmecamylamine in conscious rats, in contrast to the accepted anesthetized rat model for OAB described in Example 2. Taken together and in context, the results are useful as comparators to the anesthetized rat model for OAB in Example 2 and support the conclusion that dexmecamylamine works by inhibiting afferent signaling from the bladder.

A comparative tabular summary of the OAB assays performed by UROsphere in a conscious rat model, versus the Beckel et al. study assays, is illustrated in FIG. 6. (Beckel et al., *Expression of functional nicotinic acetylcholine receptors in rat urinary bladder epithelial cells*, Am J Physiol Renal Physiol, 290: F103-F110, 2006, first published 6 Sep. 2005, herein incorporated by reference). The Beckel et al. study in anesthetized rats administered the test compounds (hexamethonium, nicotine, methyllycaconitine, and choline) intravesically. The comparative results of these two studies suggest, possibly, that intravesical administration in conscious rats is not an acceptable animal model for OAB.

The Beckel study found significant effects on nicotinic receptors expressed in rat urinary bladder epithelial cells with nicotine (0.05 and 1 µM), hexamethonium (10 and 100 µM), and choline (10 and 100 µM), while the UROsphere study found significant effects with tolterodine (10 µM) and TC-5213 (1 and 10 µM) but not with hexamethonium (10 µM) or TC-5214 (0.1, 1 and 10 µM).

One theory, to which the present inventors should not be bound, is that in conscious rats supraspinal mechanisms tonically decrease the frequency of bladder contraction (floor effect) whereas in anesthetized rats (i.e., without CNS inhibitory inputs) there is an increase in the inter-contraction interval allowing inhibition to be observed following administration of hexamethonium or TC-5214. The present inventors, therefore, sought testing of TC-5214 in an anesthetized rat model.

Example 2

Dexmecamylamine in OAB: Intravesical Model in Anesthetized Rats

Figure 7:
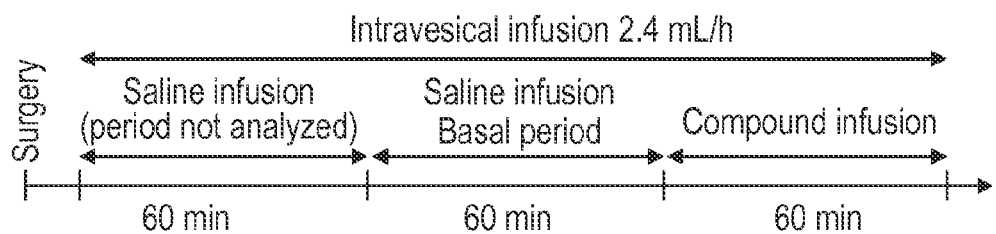
FIG. 7 illustrates the infusion for the intravesical model of anesthetized rats.
Figure 8:
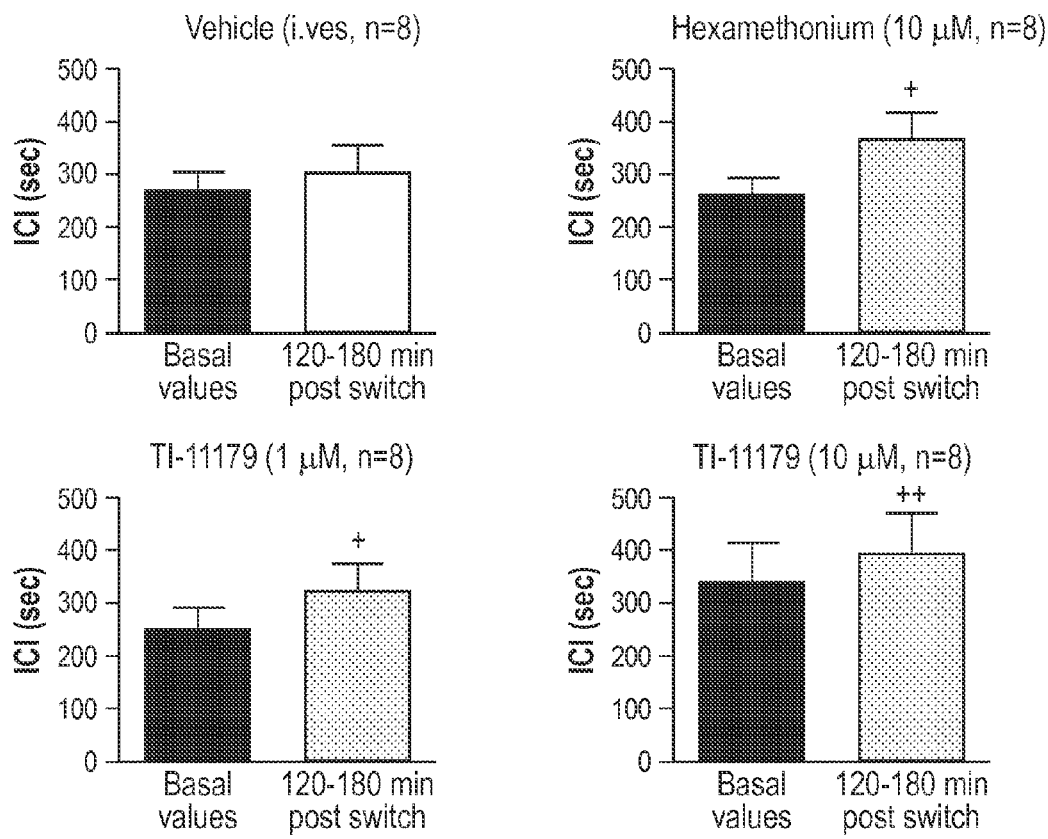
FIGS. 8-12, illustrate that dexmecamylamine at concentrations of 1 μM and 10 μM produced similar changes in cystometry as 10 μM hexamethonium (positive control).
Figure 9:
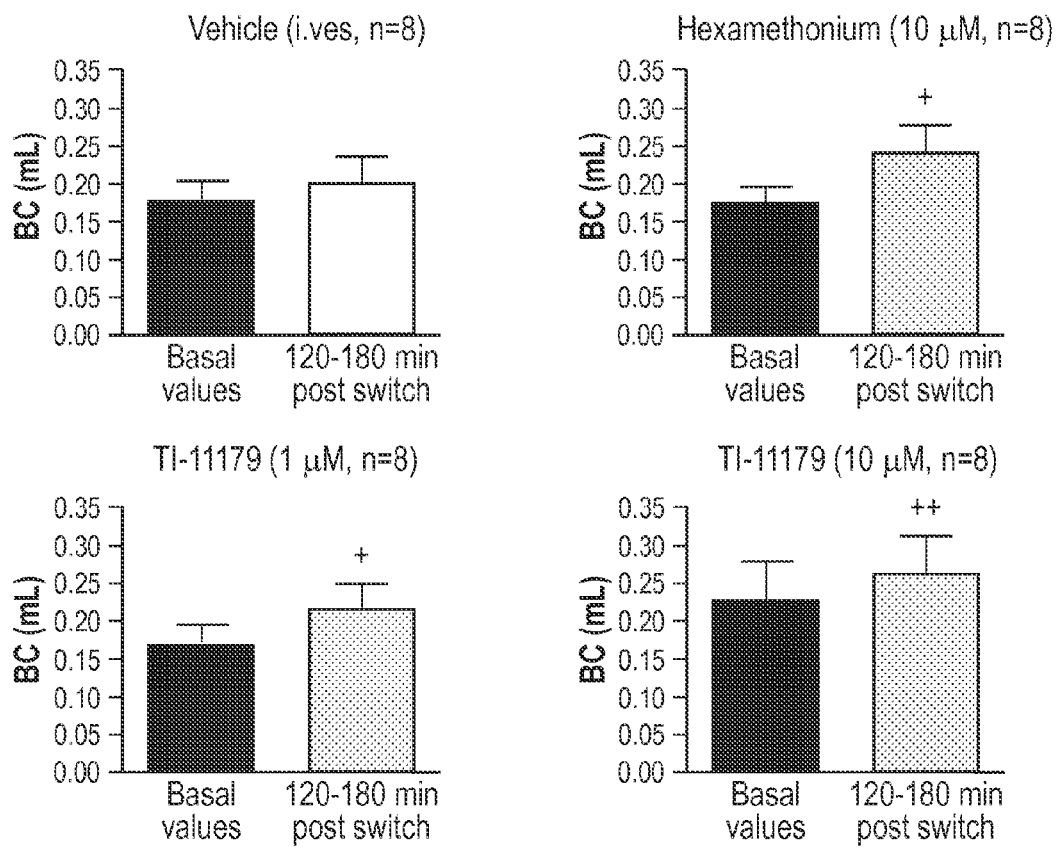
Figure 10:
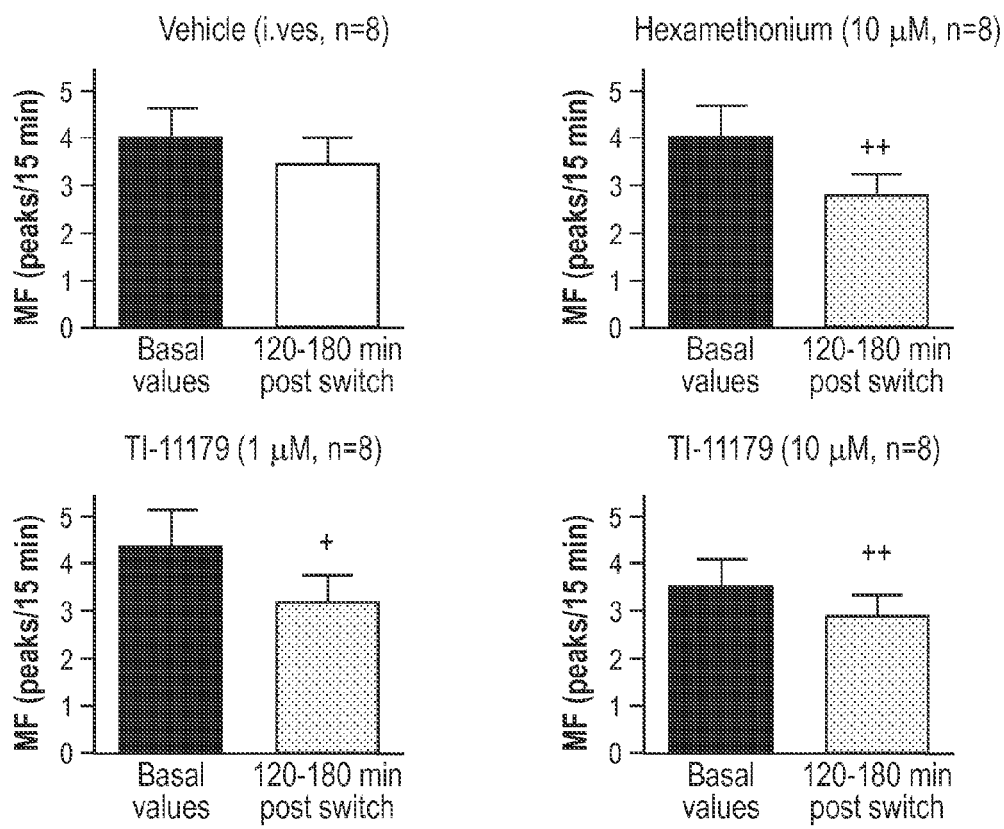

Female Sprague Dawley rats (200-290 g) from Charles River France, housed in 3-4 rats per cage were anesthetized with urethane (1.2 g/kg) s.c., 3 mL/kg). A polyethylene catheter was implanted into the bladder through the dome. Ureters were tied and cut. Intravesical infusion periods with saline followed by an intravesical infusion period with one of the test compounds, hexamethonium (10 µM) or dexmecamylamine (1 and 10 µM), are depicted in FIG. 7.

The intravesical anesthetized rat model is a model of increased bladder contraction frequency. The model is a "simplified" well established model used to evaluate OAB agents, recognizing that there are decreased inputs from cortical centers. This is the first known experiment using the intravesical anesthetized rat model of increased bladder contraction frequency to test dexmecamylamine for potential efficacy in treating OAB.

Figure 11:
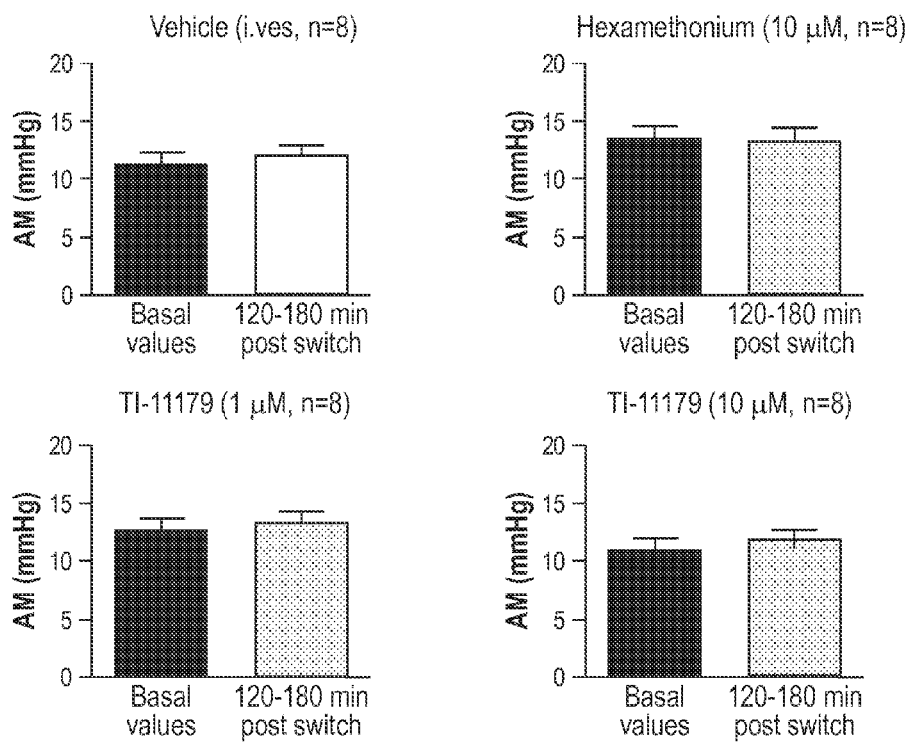
Figure 12:
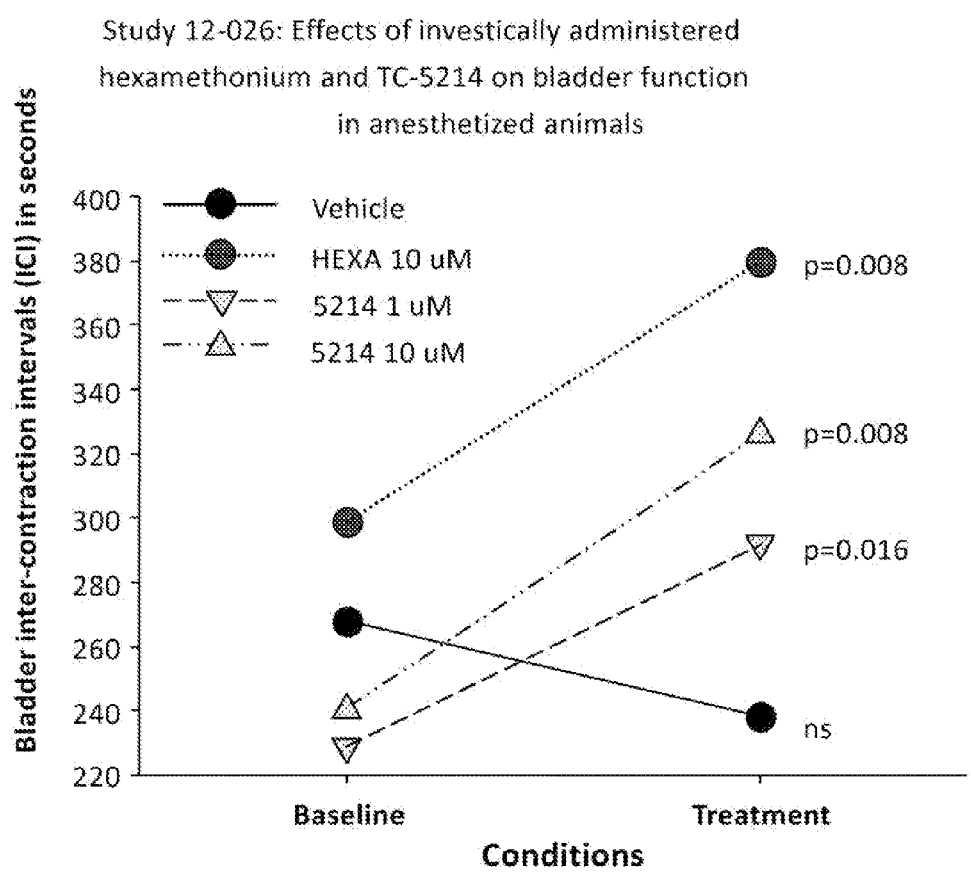

As shown in FIGS. 8-12, dexmecamylamine at concentrations of 1 µM and 10 µM produced similar changes in cystometry as 10 µM hexamethonium. Dexmecamylamine demonstrated a statistically significant increase in inter-contraction interval (ICI), FIG. 8. Dexmecamylamine demonstrated a statistically significant increase in bladder capacity (BC), FIG. 9. Dexmecamylamine demonstrated a statistically significant decrease in micturition frequency (MF), FIG. 10. Dexmecamylamine demonstrated no significant decrease in bladder contraction amplitude (AM), FIG. 11. Rather, dexmecamylamine was substantially similar to placebo. The result of no significant decrease in bladder contraction amplitude, as shown in FIG. 11, contrasts with the significant decrease in bladder electric potentials for bladder contraction amplitude shown by Kaplan in his studies of racemic mecamylamine administered to seven spinal cord injured patients (Kaplan et al., *Reduction of bladder contractility after alpha-adrenergic blockade and after ganglionic blockade*, Acta Neurol. Scandinav. 59, 172-77, 1979). Kaplan therefore concluded that the use of racemic mecamylamine to control autonomic hyperreflexia may result in a reduction in the ability of the urinary bladder to effectively contract (Kaplan at p. 176). FIG. 12 presents the Inter-Contraction Interval (ICI) data reanalyzed using median values and demonstrates the effects of intravesically administered hexamethonium and dexmecamylamine on bladder function in anesthetized animals.

This is a positive study supporting the efficacy of dexmecamylamine for the treatment of OAB with the potential for an improvement in side effect profile. For example, the findings of increased bladder capacity with no significant decrease in bladder contraction amplitude demonstrate that dexmecamylamine supports effective bladder emptying, thereby contributing to the increase in ICI and the decrease in MF without a detrimental effect on, or interference with, the ability of the bladder to contract.

These experimental results are significant in supporting the safe and effective use of relatively low doses of dexmecamylamine to treat OAB.

Dexmecamylamine at concentrations of 1 µM and 10 µM produced similar changes to those observed with 10 µM hexamethonium, a known nicotinic receptor antagonist, including a statistically significant increase in inter-contraction interval (ICI), a statistically significant increase in bladder capacity (BC), a statistically significant decrease in micturition frequency (MF), and no significant change in bladder contraction amplitude (AM). These results are consistent with effects on afferent signaling. The magnitude of the effects noted at 1 µM dexmecamylamine were similar to those noted at 10 µM, suggesting local effects approaching $E_{max}$ at 1 µM, translating to expected mean concentrations in humans following a 0.5 mg BID dosing of approximately 3 µM. Similarly, 1 mg BID dexmecamylamine will produce mean urine concentrations of approximately 6 µM. These results suggest that the administration of relatively low doses of dexmecamylamine can have profound positive effects on symptoms of OAB, such as urge, high micturition frequency, urinary incontinence and nocturia, with a favorable side effect profile. The results also suggest that relatively low doses of dexmecamylamine will affect afferent signaling from the bladder.

Example 3

Oral Agent for Intravesical Drug Delivery

One aspect of the present invention is the use of dexmecamylamine as an oral agent for intravesical drug delivery. Oral doses (up to 4 mg BID) of dexmecamylamine evaluated during clinical studies for depression produced concentrations in the bladder in excess of 10 µM. As shown above, similar concentrations of hexamethonium produce meaningful changes in the frequency of bladder contraction. Nicotinic receptors, including α3, α7, and β4, are expressed in the bladder urothelium itself. Agents that block nicotinic receptors in the bladder, such as hexamethonium, decrease bladder contractions and may block sensation of urgency. Inhibition of the α3 receptor diminishes bladder contraction frequency and afferent signaling to the brain (via P2X), thereby blocking or reducing the sensation of urgency. Support for this mechanism includes experiments demonstrating that A3-knockout rodents exhibit distended bladders. (Xu et al., *Megacystis, mydriasis, and ion channel defect in mice lacking the α3 neuronal nicotinic acetylcholine receptor*, Proc. Natl. Acad. Sci., Vol. 96, pp. 5746-5751, May 1999.)

During the dexmecamylamine clinical program for depression, including the initial phase 1 study (conducted by Targacept), ≥90% of orally administered dexmecamylamine was excreted unchanged in the bladder. This suggests that dexmecamylamine may also work locally in the bladder to inhibit bladder contraction frequency without significantly decreasing bladder contraction amplitude, such as shown in the anesthetized rat model for OAB described in Example 2.

Moreover, in a randomized, double-blind, sequential, ascending single dose, active comparator (racemic mecamylamine) cross-over study to evaluate the safety, tolerability, pharmacokinetics and pharmacodynamics of TC-5214 (S-(+)-mecamylamine) in healthy young male subjects, measurements were made to assess whether stereoconversion occurred from exo-S to exo-R. As shown by plasma PK analysis, all TC-5213 plasma concentrations following TC-5214 administration were either below the limit of quantification (BLQ) or zero. There was no evidence of TC-5214 interconversion to TC-5213 following TC-5214 administration. As shown by urine PK analyses, all but one urine collection period across all subjects had a zero TC-5213 concentration following administration of TC-5214. Reference is made to Protocol TC-5214-23-CLP-001 from IND 116299, herein incorporated by reference in its entirety.

In earlier non-human studies (mouse carcinogenicity studies), urinary retention was noted with dexmecamylamine but at much higher doses and concentrations than achieved in the clinical program for depression and the intravesical drug delivery studies disclosed herein. Near identical observations were noted in the Summary Basis of Approval for Toviaz®. Further, the Summary Basis of Approval for Detrol® indicates similar (lower rates) of bladder dilatation, as is noted in dexmecamylamine's carcinogenicity studies. Urinary retention, and concomitant urinary tract infection, is not anticipated to be a therapy-limiting side effect for relatively low doses and concentrations of dexmecamylamine (FIG. 24).

Example 4

Use-Dependent Inhibition of Human α3β4 Channels by TC-5213 (Exo-R-Mecamylamine), TC-5214 (Exo-5-Mecamylamine), and TC-5231 (Racemic Mecamylamine)

The objective of this study was to examine and compare the use-dependent effects of exo-R-mecamylamine, dexmecamylamine and racemic mecamylamine on human α3β4 channels expressed in CHO cells (ChanTest®). Based on previously published data (Giniatullin, R. A. et al., *Rapid relief of block by mecamylamine of neuronal nicotinic acetylcholine receptors of rat chromaffin cells in vitro: an electrophysiological and modeling study*, Mol. Pharmacol. 2000 October, 58(4):778-87.), racemic mecamylamine is a use-dependent blocker, hence its effect depends on concentration and number of co-applications with agonist. There was an assumption that the dependence on the number of co-applications would be the most relevant to clinical concentrations, since upon the time of exposure in vivo, the number of open channels could reach substantial numbers; perhaps due to channel spontaneous opening, flickering, and endogenous transmitter release as a result of brain activity. All experiments were performed using a conventional Dynaflow (Cellectricon Inc.) electrophysiological system. Dynaflow settings: To achieve continuous exposure to the drug we used following Dynaflow chip loading. An example of standard chip loading for use-dependent experiments with example for 30 µM ACh and 0.1 µM of TC-05231 (racemic mecamylamine). For the following experiments, ACh always consisted of 30 µM and concentrations of compounds were, 0.03, 0.1, 0.3 and 1.0 (µM). FIG. 13 illustrates the settings.

Application Sequence
Configuration of the Dynaflow Chip

Channel #1 contained the agonist solution (30 µM ACh) and channels #2 through #5 were loaded with control solutions, channel #6 and channel #7 were loaded with TC-5231 (racemic mecamylamine) (0.1 µM) and channel #8 with 30 µM ACh+0.1 µM TC-5231. Applications were performed by positioning the cell in front of channel #1 for 1 second, followed by channel #3, then back to channel #1 by rapidly moving the Dynaflow chip, which consisted of both the laminar flow from the channels and the entire bath solution. The additional channels between control and ACh-containing channel were used: (1) to provide the needed space for an additional washout to avoid contaminating the control channels with the agonist solution; and (2) to allow for the necessary amount of time for the Dynaflow stage to reach its optimum scanning speed.

The following steps were made during experiments:
3.1. Establishment of recording baseline: First, pipette with cells moved to channel #3. Then cells were exposed to ACh by moving cells to channel #1 for 1 second and back to channel #3. This movement of cells was repeated 10 times at 30 second intervals;
3.2. Collection data on use-dependent inhibition: After establishment of stable baseline, cells were moved to channel #6 and exposed to a test compound for 30 sec. Then cells were moved to channel #8 for 1 second and back to channel #6 for 30 seconds (total 10 times with intervals 30 seconds); and
3.3. To test reversibility of block (washout): repeat step 1. Note: with this chip setting, during repeated application of acetylcholine plus test compound, there was no interruption in application of compounds. For all calculations, peak current amplitude was normalized to the peak current amplitude evoked by the 10th application of acetylcholine.

Experimental Results

Figure 14:
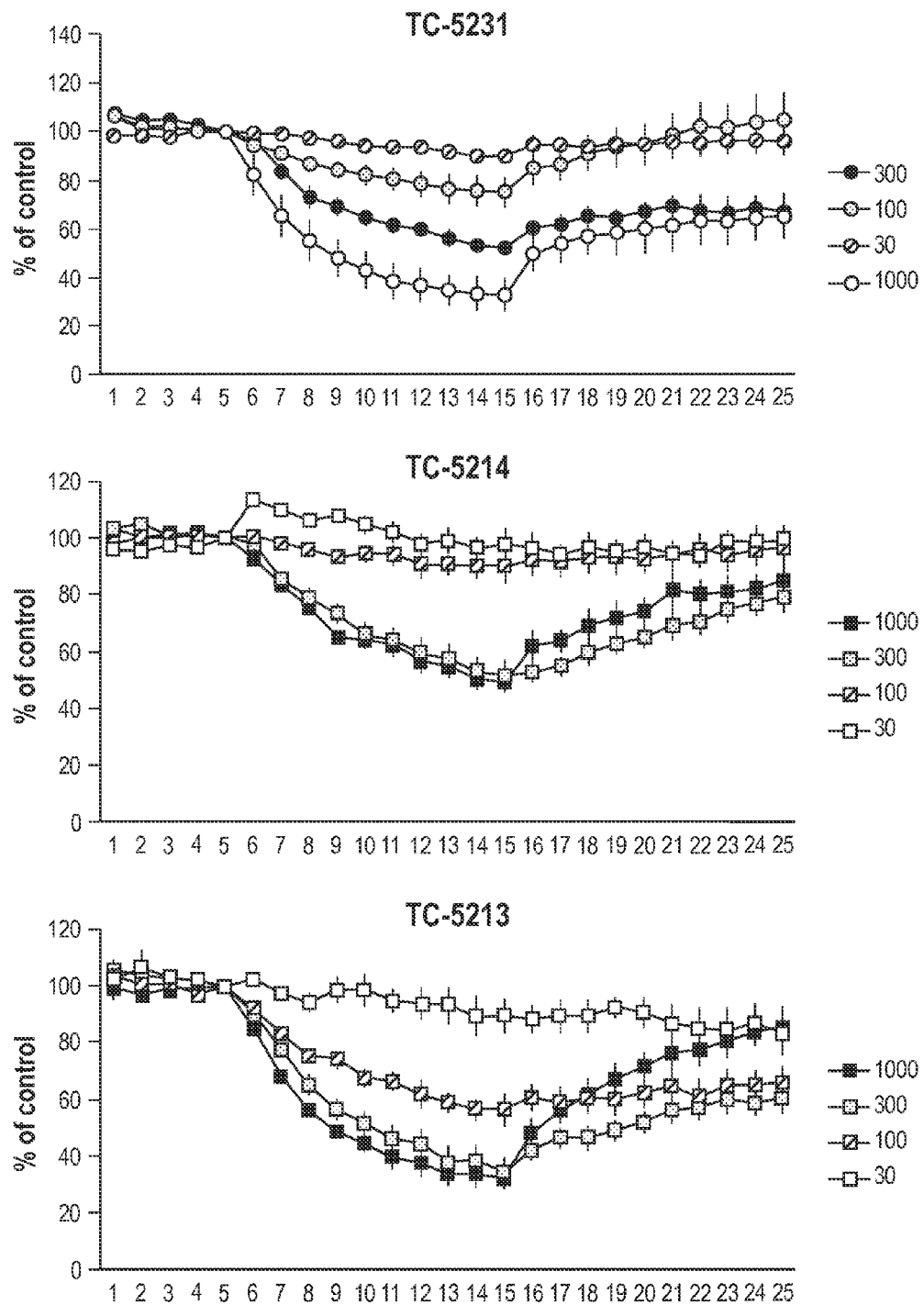
FIG. 14 illustrates experimental results of $\alpha3\beta4$ function, where plots represent concentration response and use-dependence for TC-5231, TC-5214 and TC-5213 (x=6 to 15), (x=6 to 15) and reversibility of inhibition after 10 consequent pulses of agonist alone (x=16 to 25).

Use-dependent inhibition of human α3β4 channels: The graphs illustrated in FIG. 14 summarize the experimental results. Plots represent concentration response and use-dependence for TC-5231 (racemic mecamylamine), TC-5214 (S(+) mecamylamine) and TC-5213 (R(−) mecamylamine) (x=6 to 15). They also demonstrate reversibility of inhibition after 10 consequent pulses of agonist alone (x=16-25).

The graphs in FIG. 14 illustrate the use-dependent inhibition of the human α3β4 receptor stimulated by an activating concentration of the endogenous neurotransmitter acetylcholine. Four different concentrations of the inhibitors were added to acetylcholine and applied at the 6th application (30 nM, 100 nM, 300 nM and 1000 nM) of TC-5231 (racemic mecamylamine; FIG. 14, top panel), TC-5214 [S(+)mecamylamine; FIG. 14, middle panel] and TC-5213 [R(−)mecamylamine; FIG. 14, lower panel]. Whereas both TC-5231 and TC-5213 significantly inhibited the human α3β4 receptor at concentrations of 100 nM (20% and 60% respectively; see assymptotes to the curve with orange circles), TC-5214 resulted in minor to no detectable inhibition.

TC-5213 also showed persistent inhibition even after it was removed from the bath (>16th application). This is significant because 100 nM represents a clinically-relevant concentration achieved in patients at therapeutic doses. These results indicate that at therapeutic doses, systemic concentrations of TC-5214, in contrast to TC-5231 and TC-5213, will not inhibit ganglionic receptors mediating the cardiovascular and gastro-intestinal side effects, but can still achieve the intravesical concentrations needed to positively benefit patients with overactive bladder and related disorders. This is important because systemic inhibition of ganglionic α3β4 receptor would compromise the ability of the bladder to contract (decrease bladder contraction amplitude), thereby exacerbating OAB conditions (decrease the ability of voiding and increasing the residual volume). These data show that for purposes of efficacy and tolerability, TC-5214 is preferable to TC-5231 and TC-5213.

Figure 15:
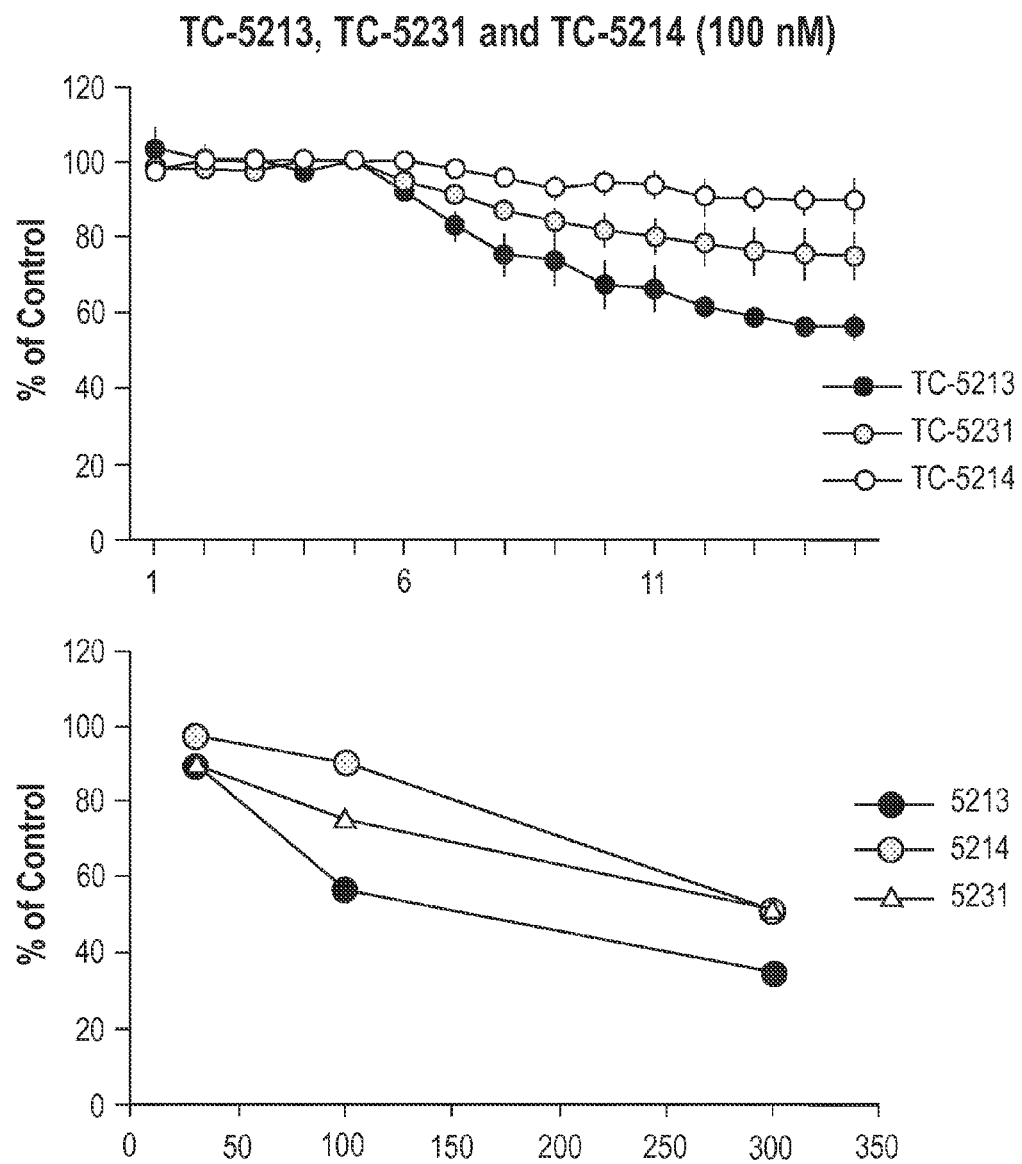
FIG. 15 provides a graphic illustration of Selectivity of use-dependent inhibition and Recovery of human $\alpha3\beta4$ channels by/after 30 and 100 nM TC-5213, TC-5214 and TC-5231, noting effects of TC-5213 were persistent after drug wash out (66% residual inhibition) whereas TC-5214 and TC-5231 exhibited full recovery.
Figure 16:
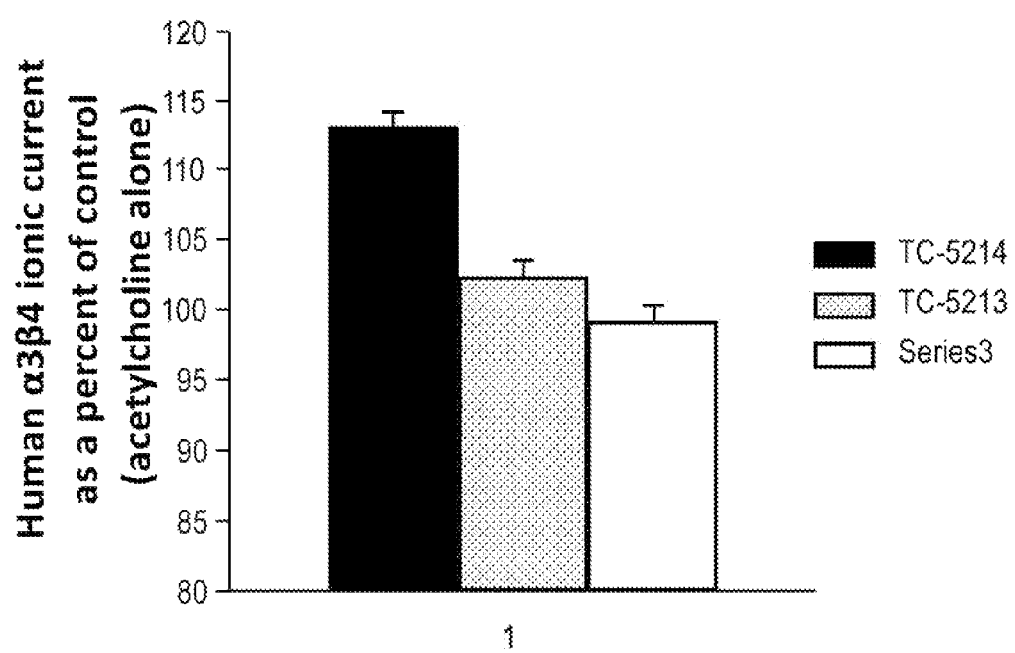
FIG. 16 provides a bar graph illustration of a concurrent weak positive modulation of $\alpha3\beta4$ function by TC-5214, which was apparent at 30 nM concentrations (t-test, $p<0.05$).

Selectivity of use-dependent inhibition and recovery of human α3β4 channels by/after 30 and 100 nM TC-5213, TC-5214 and TC-5231: At concentrations 30 nM and 100 nM, TC-5214 showed selectivity compared to TC-5213 and TC-5231 (Tables 3 and 5; FIGS. 14-16). At the end of 10 applications for TC-5214 at 100 nM, use-dependent inhibition was 10.1%±6%. In contrast, for TC-5231 and TC-5213 at 100 nM, use-dependent inhibition was 24.8%±6.5% and 43.5%±3.5%, respectively. Importantly, at a concentration 300 nM, there was a trend towards selectivity between TC-5214 and TC-5213. Effects of compounds at 1 μM concentration were found to be non-selective.

There was also a significantly "better" recovery (washout) found after application of TC-5214. As can be seen from Table 3, the inhibitory effect of TC-5213 persisted during wash out (66%) whereas TC-5214 and TC-5231 exhibited full recovery. Since the "off" rate of use-dependent blockers is a critical parameter in the determination of use-dependent inhibition efficacy (Giniatullin, R. A. et al., Mol. Pharmacol. 2000 October; 58(4):778-87), this could be an important difference favoring TC-5214. These inhibitory effects can contribute to persistent systemic side effects of TC-5213 and can have detrimental effects on the amplitude of bladder contraction (through inhibition of the parasympathetic innervation to the bladder).

These data support dexmecamylamine (TC-5214) as the superior compound for treating OAB in comparison to TC-5213 and racemic mecamylamine. Dexmecamylamine provides the best chance for bladder selectivity over systemic effects in a relevant dosing range, namely 0.25 mg to 2 mg, BID. As will be discussed in more detail hereinafter, Example 6 confirms this hypothesis of systemic side effects attributable to TC-5213, including histopathology findings and even deaths with 50 mg/kg doses.

TABLE 1

100 nM inhibition of α3β4

| Compound | Inhibition by (%) * | recovery (%) ** |
|---|---|---|
| TC-5231 | 25% ± 7% | 105% ± 11% |
| TC-5213 | 44% ± 4% | 66% ± 3% |
| TC-5214 | 10% ± 6% | 96% ± 6% |

* % of inhibition after 10 co-applications of 30 uM of Ach and compound (100 nM)
** % of recovery following 10 application of Ach (30 uM)

FIG. 15 provides a graphic illustration.

One possible explanation for racemic mecamylamine selectivity at 100 nM concentrations could be a concurrent weak positive modulation of α3β4 function by the TC-5214 component, which was apparent at 30 nM concentrations shown in Table 5. (Student paired t-test, p<0.05). Table 2 and FIG. 16 illustrate the difference. Consistently, positive modulation of α4β2 function for TC-5214 (1 μM) were published previously (Fedorov, N. B., Benson, L. C., Graef, J., Lippiello, P. M., & Bencherif, M., *Differential pharmacologies of mecamylamine enantiomers: positive allosteric modulation and noncompetitive inhibition*, J Pharmacol Exp Ther. 2009 February; 328(2):525-32. doi: 10.1124/jpet.108.146910. Epub 2008 Oct. 28).

Regardless of the reason, any positive effects on bladder function from the dexmecamylamine component of racemic mecamylamine were more than outweighed by the negative effects (e.g., see Kaplan et al.).

TABLE 2

| TC-5214 | | | TC-5213 | | | TC-5231 | | |
|---|---|---|---|---|---|---|---|---|
| 100 | 0 | 5 | 100 | 0 | 5 | 100 | 0 | 5 |
| 113.264623 | 2.82920213 | 5 | 102.535045 | 1.26940077 | 5 | 99.2881312 | 1.41013807 | 5 |

FIG. 16 provides a bar graph illustration.

Use-dependent inhibition of human α3β4 channels by TC-5213, TC-5214 and TC-5231: First box is control, second box is use-dependent inhibition and third box is recovery. The following data demonstrate the use-dependent effect of dexmecamylamine as an inhibitor of the α3β4 receptors.

TABLE 3

| 100 nM | | | | | | | | |
|---|---|---|---|---|---|---|---|---|
| dexmecamylamine TC-5214 | | | exo-R-mecamylamine TC-5213 | | | racemic mecamylamine TC-5231 | | |
| 110.39235 | 6.2141471 | 6 | 110.35523 | 9.0479008 | 4 | 94.412941 | 5.1680018 | 5 |
| 107.18628 | 5.1227994 | 6 | 108.59288 | 7.2954074 | 4 | 96.847203 | 4.2885468 | 5 |
| 104.74997 | 4.5360767 | 6 | 106.34885 | 8.5958926 | 4 | 97.879158 | 2.9980296 | 5 |
| 103.10643 | 3.5325503 | 6 | 107.67991 | 8.6666311 | 4 | 97.878542 | 3.4017681 | 5 |
| 98.985098 | 2.3924454 | 6 | 104.04671 | 7.3811188 | 4 | 98.744361 | 2.8755266 | 5 |
| 97.905403 | 2.0609577 | 6 | 103.44049 | 6.06131 | 4 | 98.469778 | 3.3080718 | 5 |
| 100.01443 | 3.1166409 | 6 | 100.76959 | 3.9047766 | 4 | 98.375194 | 2.536996 | 5 |
| 99.956018 | 1.987225 | 6 | 101.00448 | 1.7329819 | 4 | 97.792694 | 1.7948292 | 5 |
| 100.59721 | 1.6498968 | 6 | 97.385468 | 1.7748968 | 4 | 100.70982 | 0.9870814 | 5 |
| 100 | 0 | 6 | 100 | 0 | 4 | 100 | 0 | 5 |
| 100.03239 | 2.0142467 | 6 | 92.210629 | 2.1774717 | 4 | 94.464556 | 1.0577062 | 5 |
| 98.018959 | 0.6596969 | 6 | 83.206797 | 4.1626432 | 4 | 91.195345 | 1.4420997 | 5 |
| 95.531371 | 1.9129955 | 6 | 75.674174 | 5.9400009 | 4 | 87.085813 | 2.8770038 | 5 |
| 93.136953 | 3.1999231 | 6 | 74.249328 | 7.0160156 | 4 | 84.285059 | 3.5763014 | 5 |
| 94.602801 | 3.194326 | 6 | 67.706155 | 6.4281519 | 4 | 82.00118 | 4.4589227 | 5 |
| 93.986743 | 3.8561403 | 6 | 66.573255 | 6.2468855 | 4 | 80.353516 | 4.9143355 | 5 |
| 90.593834 | 5.0771255 | 6 | 61.865653 | 3.2056265 | 4 | 78.261037 | 5.5987387 | 5 |
| 90.275854 | 3.4656582 | 6 | 58.963629 | 2.0360446 | 4 | 76.491576 | 6.2747431 | 5 |
| 89.841416 | 3.9367964 | 6 | 56.565328 | 2.8873945 | 4 | 75.579606 | 6.8104438 | 5 |
| 89.90028 | 6.1331845 | 5 | 56.453752 | 3.4754598 | 4 | 75.21029 | 6.4648369 | 5 |
| 91.621097 | 5.0727371 | 5 | 60.745723 | 2.656892 | 4 | 84.855951 | 7.2317484 | 5 |
| 91.789093 | 5.9140928 | 5 | 58.976029 | 2.1847971 | 4 | 86.429423 | 6.991911 | 5 |
| 92.64822 | 5.6061841 | 5 | 60.371587 | 1.2714806 | 4 | 91.171745 | 7.6882322 | 5 |
| 92.723276 | 5.8249451 | 5 | 59.981154 | 3.4267924 | 4 | 93.397577 | 8.4717592 | 5 |
| 92.455228 | 5.4086464 | 5 | 62.180699 | 1.9942915 | 4 | 94.836997 | 8.7550595 | 5 |
| 94.095883 | 5.2464941 | 5 | 64.274318 | 2.5206339 | 4 | 98.261348 | 9.2172416 | 5 |
| 95.563812 | 6.5416379 | 5 | 60.852844 | 3.8413171 | 4 | 101.91971 | 10.375935 | 5 |
| 93.81432 | 5.9104828 | 5 | 65.147761 | 1.5063322 | 4 | 101.66473 | 9.9789978 | 5 |
| 95.451183 | 5.3687557 | 5 | 65.368158 | 1.1070995 | 4 | 103.7206 | 11.777492 | 5 |
| 96.483696 | 6.4348657 | 5 | 65.874034 | 3.1596615 | 4 | 104.733 | 11.470592 | 5 |

TABLE 4

| 300 nM | | | | | | | | |
|---|---|---|---|---|---|---|---|---|
| TC-5214 | | | TC-5213 | | | TC-5231 | | |
| 102.95931 | 6.4054921 | 7 | 113.75295 | 4.8469718 | 5 | 108.84896 | 9.9589044 | 5 |
| 99.069946 | 5.9273447 | 7 | 106.31727 | 3.7909686 | 5 | 105.9134 | 7.3719102 | 5 |
| 99.583804 | 4.375694 | 7 | 114.52802 | 5.257688 | 5 | 107.3931 | 5.506939 | 5 |
| 100.76254 | 4.7122439 | 7 | 106.55685 | 1.1653987 | 5 | 109.69744 | 3.7161102 | 5 |
| 100.11077 | 4.0872098 | 7 | 104.49124 | 3.07758 | 5 | 109.28488 | 4.2874228 | 5 |
| 103.05656 | 2.9577742 | 7 | 105.31958 | 3.224589 | 5 | 107.35406 | 3.062586 | 5 |
| 104.46395 | 3.1259492 | 7 | 104.60854 | 2.257558 | 5 | 104.19653 | 2.0250528 | 5 |
| 101.01783 | 1.1765285 | 7 | 103.57829 | 2.5566723 | 5 | 104.65607 | 1.2395652 | 5 |
| 100.62119 | 0.6719512 | 7 | 102.09307 | 3.4845279 | 5 | 102.49753 | 0.3622462 | 5 |
| 100 | 0 | 7 | 100 | 0 | 5 | 100 | 0 | 5 |
| 97.548897 | 1.0623045 | 7 | 90.458465 | 4.4256901 | 5 | 96.193858 | 3.5793021 | 5 |
| 85.334103 | 2.1138694 | 7 | 78.139911 | 4.7992073 | 5 | 83.84755 | 3.549978 | 5 |
| 78.517612 | 3.8313513 | 7 | 65.513844 | 7.1550546 | 5 | 72.986089 | 4.4471529 | 5 |
| 73.053559 | 3.8278624 | 7 | 56.431325 | 5.2103141 | 5 | 69.142662 | 3.740215 | 5 |
| 65.607261 | 4.4987848 | 7 | 51.799043 | 6.2828504 | 5 | 64.596603 | 3.2495542 | 5 |
| 63.439835 | 5.19681 | 7 | 46.014919 | 7.7513643 | 5 | 61.402301 | 3.3728104 | 5 |
| 59.038336 | 5.793906 | 7 | 44.212937 | 4.3176713 | 5 | 59.716547 | 3.0914395 | 5 |
| 57.131162 | 5.6053348 | 7 | 38.380987 | 4.5879007 | 5 | 56.12511 | 3.5187892 | 5 |
| 52.683045 | 5.6139651 | 7 | 38.546831 | 2.4148485 | 5 | 53.222979 | 3.2557417 | 5 |
| 51.253682 | 5.623505 | 7 | 34.541595 | 4.9947726 | 5 | 52.049329 | 3.1945627 | 5 |
| 51.581387 | 3.5589241 | 7 | 42.54486 | 5.5179244 | 5 | 60.192409 | 3.514451 | 5 |
| 54.661803 | 3.7571081 | 7 | 46.474766 | 5.77099 | 5 | 61.883019 | 4.1659489 | 5 |
| 59.503024 | 4.5582749 | 7 | 46.257894 | 4.5235158 | 5 | 65.224604 | 3.8789578 | 5 |
| 62.606603 | 3.9701393 | 7 | 49.008736 | 4.0317497 | 5 | 64.388073 | 3.6378415 | 5 |
| 64.790725 | 3.9040039 | 7 | 52.053213 | 6.1996969 | 5 | 67.031073 | 3.7789297 | 5 |
| 68.737101 | 4.6421408 | 7 | 55.93872 | 4.594645 | 5 | 69.16669 | 4.4640233 | 5 |
| 70.112156 | 4.7770958 | 7 | 57.608963 | 4.6727491 | 5 | 67.234281 | 5.4331615 | 5 |
| 74.684926 | 5.2140126 | 7 | 60.061573 | 4.0783444 | 5 | 66.399164 | 5.4451556 | 5 |
| 76.819073 | 4.5521525 | 7 | 58.922163 | 5.9425867 | 5 | 68.666938 | 5.0034297 | 5 |
| 78.883194 | 5.3562543 | 7 | 60.542367 | 6.286265 | 5 | 66.778343 | 5.1885986 | 5 |

TABLE 5

| 30 nM | | | | | | | | |
|---|---|---|---|---|---|---|---|---|
| TC-5214 | | | TC-5213 | | | TC-5231 | | |
| 94.799131 | 3.5994367 | 4 | 104.3922 | 10.356613 | 5 | 100.58705 | 3.6831127 | 5 |
| 93.825159 | 3.3889088 | 4 | 102.76657 | 10.180107 | 5 | 102.32698 | 3.5680617 | 5 |
| 96.199165 | 2.310386 | 4 | 102.69376 | 9.2804036 | 5 | 102.98707 | 3.2123497 | 5 |
| 99.507708 | 4.0716336 | 4 | 101.89359 | 8.3396757 | 5 | 102.75969 | 3.1041884 | 5 |
| 99.076715 | 2.7960076 | 5 | 103.92156 | 8.6565769 | 5 | 103.20532 | 2.8255128 | 5 |
| 95.465536 | 2.1201299 | 5 | 102.41921 | 7.1317475 | 5 | 105.27945 | 1.6973968 | 5 |
| 95.101684 | 1.787585 | 5 | 106.63281 | 6.5433234 | 5 | 101.68368 | 1.1237255 | 5 |
| 97.103106 | 1.0424245 | 5 | 102.64983 | 2.6376679 | 5 | 100.71962 | 0.8707862 | 5 |
| 96.615475 | 1.7529366 | 5 | 101.90402 | 1.6956302 | 5 | 100.4595 | 0.5170502 | 5 |
| 100 | 0 | 5 | 100 | 4.494E−15 | 5 | 100 | 0 | 5 |
| 113.26462 | 2.8292021 | 5 | 102.53504 | 1.2694008 | 5 | 99.288131 | 1.4101381 | 5 |
| 109.57438 | 3.2952628 | 5 | 97.751618 | 2.3277392 | 5 | 98.973844 | 2.0480434 | 5 |
| 106.02957 | 2.4692013 | 5 | 94.195149 | 3.6036648 | 5 | 97.504563 | 2.4721139 | 5 |
| 107.58769 | 2.7211102 | 5 | 98.967697 | 4.6421027 | 5 | 95.884199 | 2.2385475 | 5 |
| 104.59838 | 3.2883366 | 5 | 98.466942 | 5.7759388 | 5 | 94.250625 | 2.8561002 | 5 |
| 102.02842 | 3.7447374 | 5 | 95.1253 | 4.4363881 | 5 | 93.728802 | 3.0713623 | 5 |
| 97.82038 | 4.133905 | 5 | 94.025806 | 5.8318955 | 5 | 93.669297 | 2.7199943 | 5 |
| 99.029516 | 4.9536502 | 5 | 93.078059 | 6.6197534 | 5 | 91.601042 | 2.7924188 | 5 |
| 96.286812 | 4.3177829 | 5 | 89.705141 | 7.4639661 | 5 | 89.960737 | 2.433162 | 5 |
| 97.417897 | 6.3846851 | 5 | 89.376743 | 6.1311363 | 5 | 89.926044 | 3.1929139 | 5 |
| 96.434957 | 5.8609708 | 4 | 88.360538 | 5.1914307 | 5 | 94.523427 | 4.0699516 | 5 |
| 94.161876 | 3.6469089 | 4 | 89.495279 | 6.1739177 | 5 | 94.553983 | 3.5127065 | 5 |
| 96.543055 | 5.7577529 | 4 | 89.659469 | 5.8472073 | 5 | 93.637268 | 3.8515846 | 5 |
| 94.970866 | 4.8120363 | 4 | 92.591636 | 3.8651883 | 5 | 95.167907 | 3.4554664 | 5 |
| 96.377479 | 5.7245919 | 4 | 90.718366 | 5.6875749 | 5 | 94.856684 | 4.1668212 | 5 |
| 94.333263 | 4.4372781 | 4 | 87.119874 | 6.7537548 | 5 | 95.316517 | 6.3640526 | 5 |
| 93.371397 | 4.0381683 | 4 | 85.341358 | 7.464389 | 5 | 95.462746 | 5.9018601 | 5 |
| 98.36072 | 4.5338015 | 4 | 84.540382 | 8.2135355 | 5 | 96.142912 | 5.7776922 | 5 |
| 98.636649 | 5.8554277 | 4 | 86.94742 | 7.6200591 | 5 | 96.283323 | 5.6766562 | 5 |
| 99.042661 | 5.5610899 | 4 | 83.619418 | 7.9508634 | 5 | 96.012256 | 6.0484626 | 5 |

TABLE 6

| 1 μM | | | | | | | | |
|---|---|---|---|---|---|---|---|---|
| TC-5214 | | | TC-5213 | | | TC-5231 | | |
| 96.39899 | 1.829195 | | 97.70107 | 1.984375 | 4 | 121.1859 | 5.420887 | 5 |
| 96.51473 | 0.695204 | | 97.48142 | 2.890754 | 4 | 116.845 | 4.32041 | 5 |
| 97.68779 | 0.269208 | | 96.66966 | 2.800078 | 4 | 113.3898 | 5.136158 | 5 |
| 108.353 | 7.136077 | | 96.01851 | 2.620766 | 4 | 112.3336 | 5.345277 | 5 |
| 107.2434 | 5.037438 | | 96.93107 | 1.512881 | 4 | 109.7435 | 3.972616 | 5 |
| 102.8616 | 1.854046 | | 99.76924 | 2.608671 | 4 | 106.112 | 2.746303 | 5 |
| 100.4161 | 0.442032 | | 97.09279 | 2.325055 | 4 | 102.1579 | 1.72143 | 5 |
| 101.6344 | 2.205819 | | 98.62896 | 1.853728 | 4 | 101.9503 | 1.495283 | 5 |
| 101.794 | 1.443128 | | 99.29466 | 1.031324 | 4 | 100.1569 | 1.022417 | 5 |
| 100 | 0 | | 100 | 0 | 4 | 100 | 4.49E−15 | 5 |
| 92.53268 | 2.447038 | 3 | 85.11564 | 3.07191 | 4 | 82.46272 | 8.312036 | 5 |
| 83.81636 | 2.231796 | 3 | 68.35014 | 4.855187 | 4 | 65.16617 | 8.888026 | 5 |
| 75.35581 | 2.347373 | 3 | 56.1508 | 4.78996 | 4 | 55.13761 | 8.704415 | 5 |
| 64.9239 | 1.144999 | 3 | 48.74004 | 5.054257 | 4 | 47.91268 | 7.84048 | 5 |
| 63.97583 | 3.314988 | 3 | 44.63599 | 3.873483 | 4 | 42.86861 | 7.897341 | 5 |
| 62.82698 | 4.777017 | 3 | 39.82354 | 3.653287 | 4 | 38.353 | 7.73543 | 5 |
| 56.47567 | 4.345875 | 3 | 37.06584 | 3.441066 | 4 | 36.73945 | 7.404197 | 5 |
| 54.74194 | 4.430054 | 3 | 33.83352 | 3.506873 | 4 | 34.80258 | 6.540568 | 5 |
| 50.33582 | 4.141828 | 3 | 33.32621 | 3.237948 | 4 | 33.45718 | 7.327446 | 5 |
| 49.47643 | 4.357938 | 3 | 32.62919 | 2.21073 | 4 | 32.68246 | 6.854276 | 5 |
| 61.90095 | 5.964619 | 3 | 48.21741 | 2.979368 | 4 | 49.22791 | 7.266173 | 5 |
| 63.62609 | 4.103672 | 3 | 55.7894 | 3.338959 | 4 | 53.8566 | 8.025551 | 5 |
| 68.94209 | 6.123336 | 3 | 61.49629 | 4.102461 | 4 | 57.13106 | 8.14341 | 5 |
| 71.75098 | 6.175651 | 3 | 67.0089 | 3.666067 | 4 | 58.33385 | 9.61363 | 5 |
| 73.91898 | 5.226601 | 3 | 71.22387 | 3.344186 | 4 | 60.01828 | 10.67689 | 5 |
| 81.16921 | 9.231035 | 3 | 76.09989 | 2.947101 | 4 | 61.44627 | 11.16075 | 5 |
| 79.68482 | 6.027379 | 3 | 77.56543 | 2.377629 | 4 | 63.36574 | 10.62031 | 5 |
| 80.54732 | 6.371814 | 3 | 80.89717 | 3.283041 | 4 | 63.32628 | 10.25186 | 5 |
| 81.93064 | 5.602924 | 3 | 84.65681 | 2.193083 | 4 | 64.56011 | 9.466372 | 5 |
| 84.81023 | 8.071495 | 3 | 85.29092 | 3.326475 | 4 | 65.24648 | 9.576739 | 5 |

Example 5

Dexmecamylamine Pharmacology

Nicotinic acetylcholine receptor activation in capsaicin sensitive C-fiber afferents in the bladder can induce detrusor overactivity. In the central nervous system, nicotinic acetylcholine receptor activation in the spinal cord has an excitatory effect on the micturition reflex, whereas acetylcholine receptor activation in the brain has an inhibitory effect on the micturition reflex. In addition, the nicotine induced spinal cord excitatory effect may be mediated by the activation of glutamatergic mechanisms.

As shown herein, dexmecamylamine inhibits glutamate receptors in a use-dependent manner. Dexmecamylamine blocks sympathetic activity in the bladder and the excitatory glutamate receptor-mediated spinal reflex. A relatively low dose (0.001 mg/kg to 0.03 mg/kg) of dexmecamylamine is believed to inhibit $\alpha3\beta4^*$, P2X2 in the urothelium, and NR2A-B in the spinal afferent to the bladder without sufficient systemic exposure that will inhibit parasympathetic function, thereby providing a unique mechanism of action for dexmecamylamine in contrast to TC-5213, racemic mecamylamine, and other ganglionic blockers (e.g., muscarinic receptor antagonists) currently approved to treat OAB. This extension of the mechanism of action distinguishes TC-5214 from any of the ganglionic blockers currently approved to treat OAB.

FIGS. 17-22 illustrate the effects of various levels of dexmecamylamine at the NMDA (N-methyl-D-aspartate) receptors.

All experiments were carried out at receptors expressed in *Xenopus oocytes* using the method of cDNA expression. Currents evoked by glutamate were recorded using the standard two electrode voltage-clamp configuration (TVEC). *Xenopus oocytes* were prepared and injected using standard procedures.

Briefly, ovaries are harvested from *Xenopus Laevis* females that have been deeply anesthetized and pithed following the animal rights rule from the Geneva canton. A small piece of ovary is isolated for immediate preparation while the remaining part is placed at 4° C. in a sterile Barth solution containing in mM NaCl 88, KCl 1, NaHCO$_3$ 2.4, HEPES 10, MgSO$_4$.7H2O 0.82, Ca(NO$_3$)$_2$.4H$_2$O 0.33, CaCl$_2$.6H$_2$O 0.41, at pH 7.4, and supplemented with 20 µg/ml of kanamycine, 100 unit/ml penicillin and 100 µg/ml streptomycin. On the second day following dissociation, oocytes are injected with 2 ng of cDNA per oocyte containing the NR1a-NR2A or NR1a-NR2B using an automated injector (Hogg et al., J. Neurosci. Methods, 2008). All recordings are performed at 18° C. and cells superfused with OR2 medium containing in mM: NaCl 82.5, KCl 2.5, HEPES 5, CaCl$_2$.2H$_2$O 2.5, pH 7.4. Cells were held at −80 mV. Data were filtered at 10 Hz, captured at 100 Hz and analyzed using HiQ proprietary data acquisition and analysis software running under Matlab (Mathworks Inc.).

Statistical analysis were performed either using Matlab (Mathworks inc.) or Excel (Microsoft).

Figure 17:
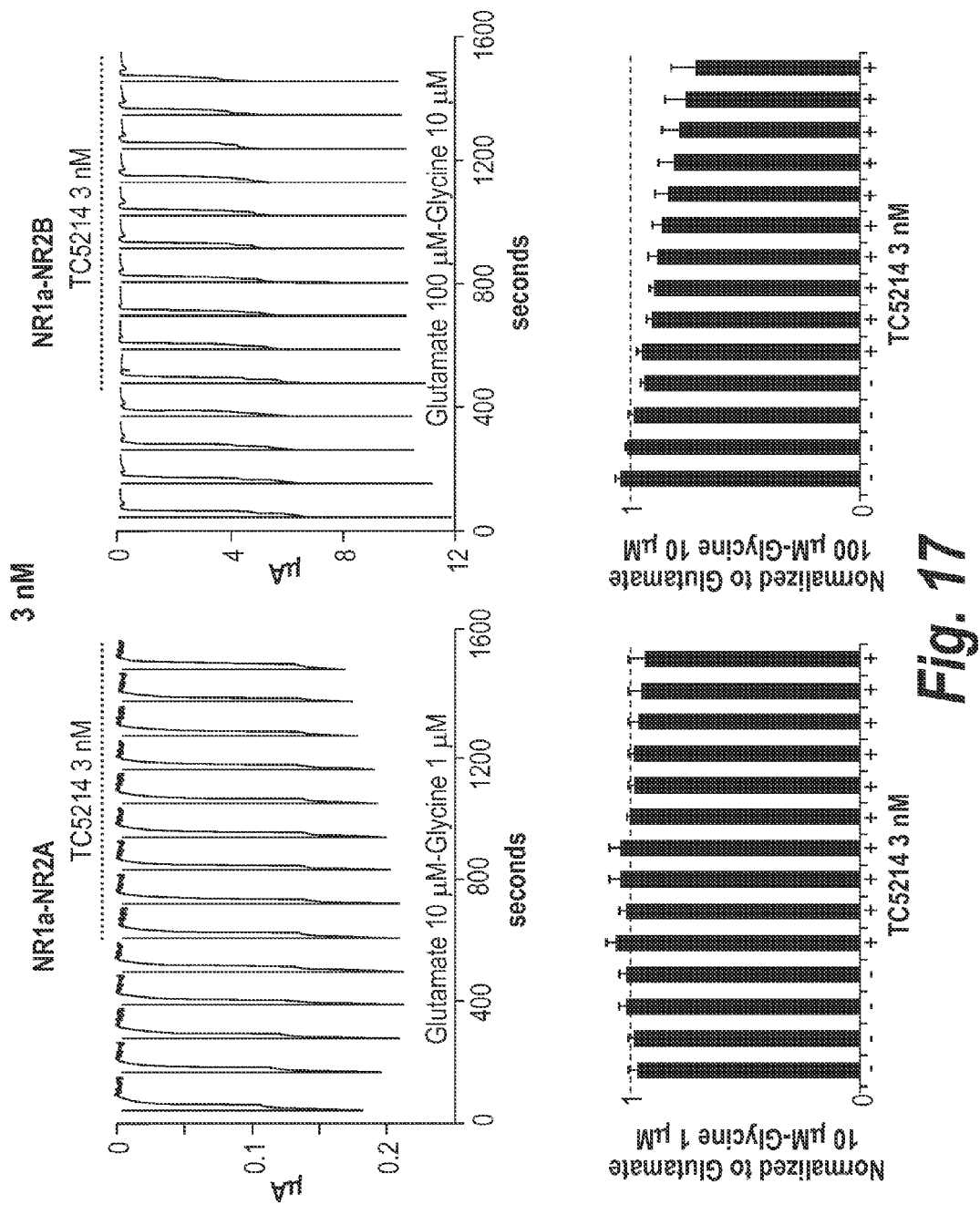
FIG. 17 illustrates the effects, of 3 nM TC-5214 (dexmecamylamine) on currents evoked by Glutamate $10\infty$M-Glycine $1\infty$M at the NMDA (N-methyl-D-aspartate) receptors subtypes NR1a-NR2A (Left panels) and NR1a-NR2B (right panels) as ionic currents expressed in ∝A (Top Figures) or as histograms normalized to the response induced by 'Glutamate 10∝-Glycine 1∝M (100%).
Figure 18:
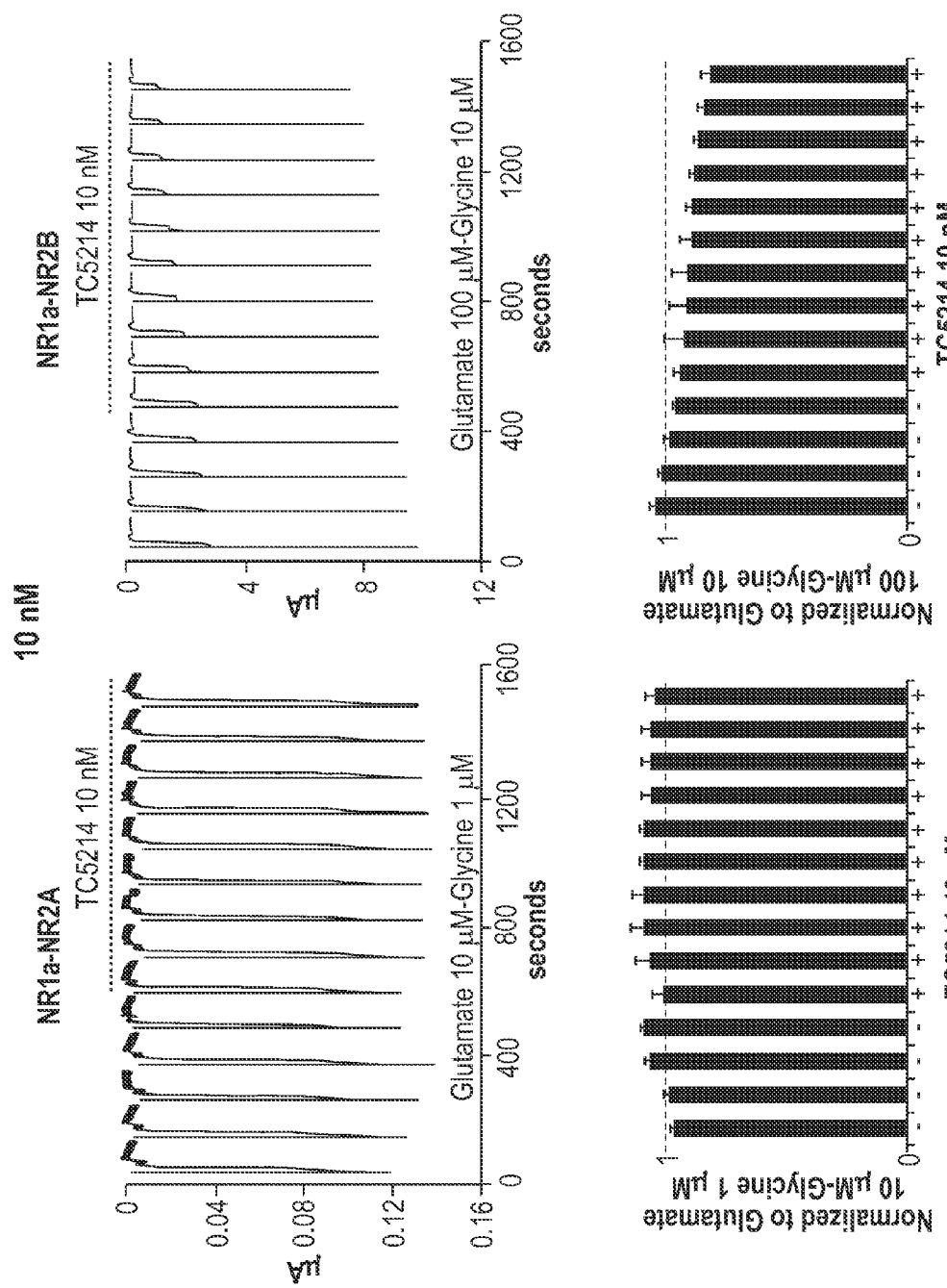
FIG. 18 illustrates the effects of 10 nM TC-5214 (dexmecamylamine) on, currents evoked by Glutamate 10∝M-Glycine 1∝M at the NMDA (N-methyl-D-aspartate) receptors subtypes NR1a-NR2A (Left panels) and NR1a-NR2B (right panels) as ionic currents expressed in ∝A (Top Figures) or as histograms normalized to the response induced by Glutamate 10∝M-Glycine 1∝M (100%).
Figure 19:
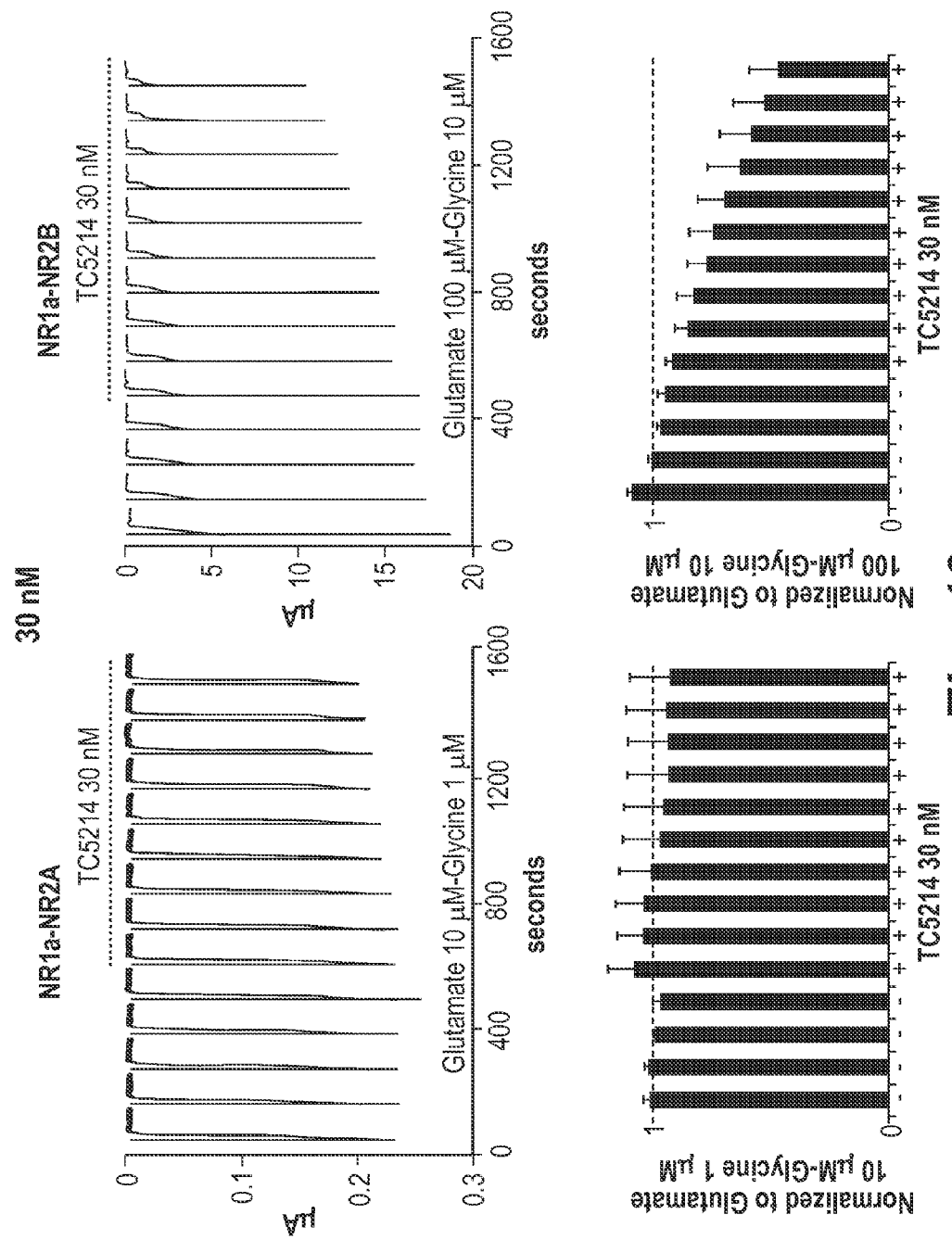
FIG. 19 illustrates the effects of 30 nM TC-5214 (dexmecamylamine) on currents evoked by Glutamate 10∝M-Glycine 1∝M at the NMDA (N-methyl-D-aspartate) receptors subtypes NR1a-NR2A (Left panels) and NR1a-NR2B (right panels) as ionic currents expressed in ∝A (Top Figures) or as histograms normalized to the response induced by Glutamate 10∝M-Glycine 1∝M (100%).
Figure 20:
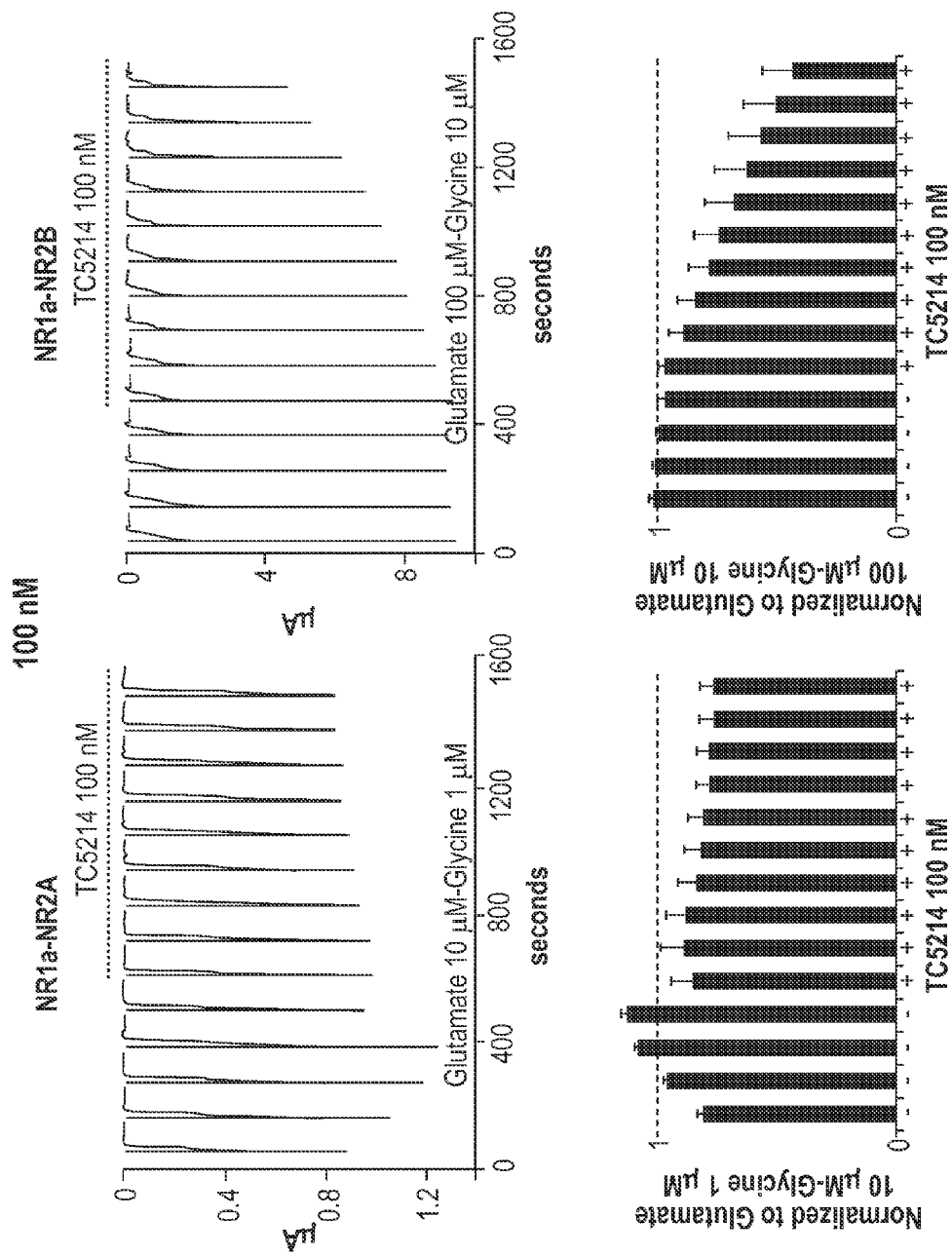
FIG. 20 illustrates the effects of 100 nM TC-5214 (dexmecamylamine) on currents evoked by Glutamate 10∝M-Glycine 1∝M at the NMDA (N-methyl-D-aspartate) receptors subtypes NR1a-NR2A (Left panels) and NR1a-NR2B (right panels) as ionic currents expressed in ∝A (Top Figures) or as histograms normalized to the response induced by Glutamate 10∝M-Glycine 1∝M (100%).
Figure 21:
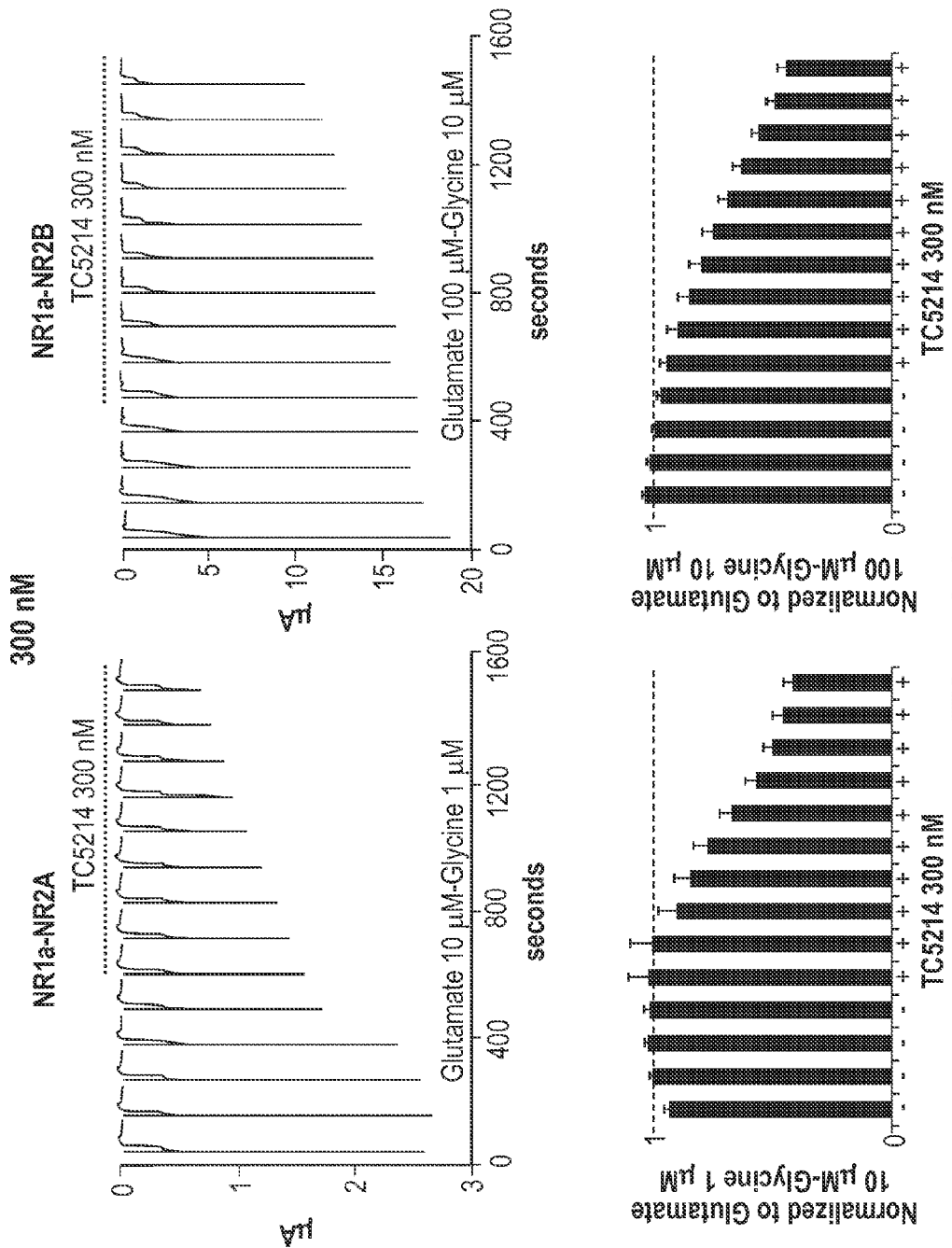
FIG. 21 illustrates the effects of 300 nM TC-5214 (dexmecamylamine) on currents evoked by Glutamate 10∝A-Glycine 1∝M at the NMDA (N-methyl-D-aspartate) receptors subtypes NR1a-NR2A (Left panels) and NR1a-NR2B (right panels) as ionic currents expressed in ∝A (Top Figures) or as histograms normalized to the response induced by Glutamate 10∝M-Glycine 1∝M (100%)

Oocytes expressing the NR1a-NR2A or NR1a-NR2B receptors were challenged at periodic intervals with a glutamate test pulse. Test drug was then applied during a sustained period and its effects monitored by measuring the amplitude and time course of the glutamate evoked currents. A typical result obtained in Study-I with this protocol is illustrated in FIG. 17.

Experiments were carried out with the NR1a-NR2A and NR1a-NR2B at least in triplicate. Positive reference compounds (ketamine and MK-801) were tested using the same protocol.

To further evaluate effects of TC-5214, experiments using sustained exposure to this compound followed by a recovery period were carried out at NR1a-NR2A and NR1a-NR2B receptors. Measurements were made with (nM) 0, 3, 10, 30, 100, 300, TC-5214 and recovery monitored during 10 minutes. In addition, the same experimental protocol will be used with cells in control conditions to assess the stability of the measurements. Effects were measured in at least three cells.

A use-dependent protocol was used to identify non-competitive inhibition of the receptors. Cells expressing the NMDA receptors were tested for their sensitivity to TC-5214 at 30 nM, using the same protocol as described above. Cells from the same batch were tested in parallel using the same incubation time with an identical concentration of TC-5214 (30 nM) but in absence of pulses during the incubation time with the compound. Two glutamate pulses were applied at the end of the incubation time, and recovery monitored as for the control conditions.

Figure 22:
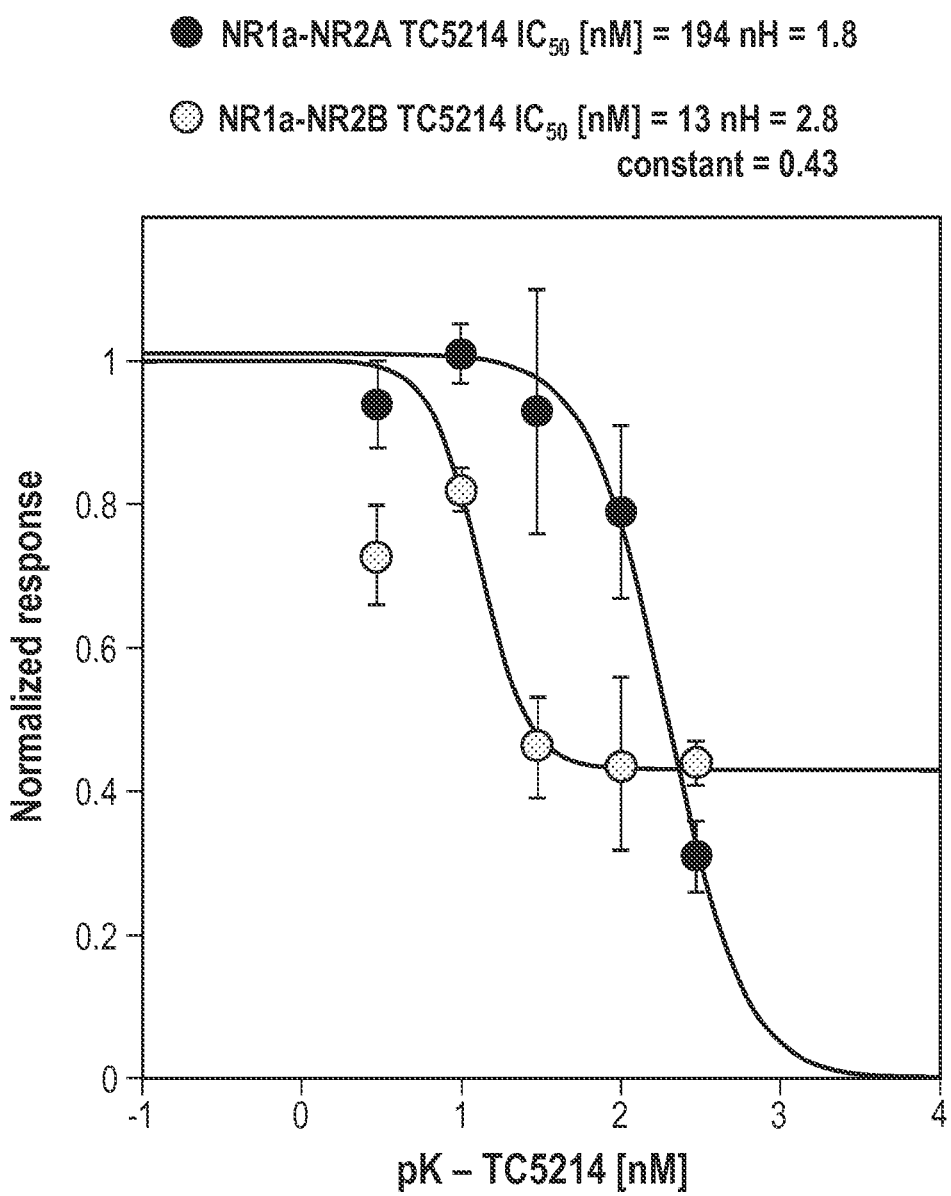
FIG. 22 illustrates the effects of the various concentrations of TC-5214 (dexmecamylamine) on currents evoked by Glutamate 10∝-Glycine 1∝M at the NMDA (N-methyl-D-aspartate) receptors subtypes NR1a-NR2A (green circles) and NR1a-NR2B (red circles) normalized to control response induced by Glutamate 10∝M-Glycine 1∝M (100%), The X-axis is a negative logarithmic scale of the concentration of TC-5214 (dexmecamylamine). The parameters derived from analysis of the curves are shown above the Figures as the $IC_{50}$ (concentration resulting in 50% inhibition of the response) and Hill coefficient (slope of the inhibition curve nH).
Figure 23:
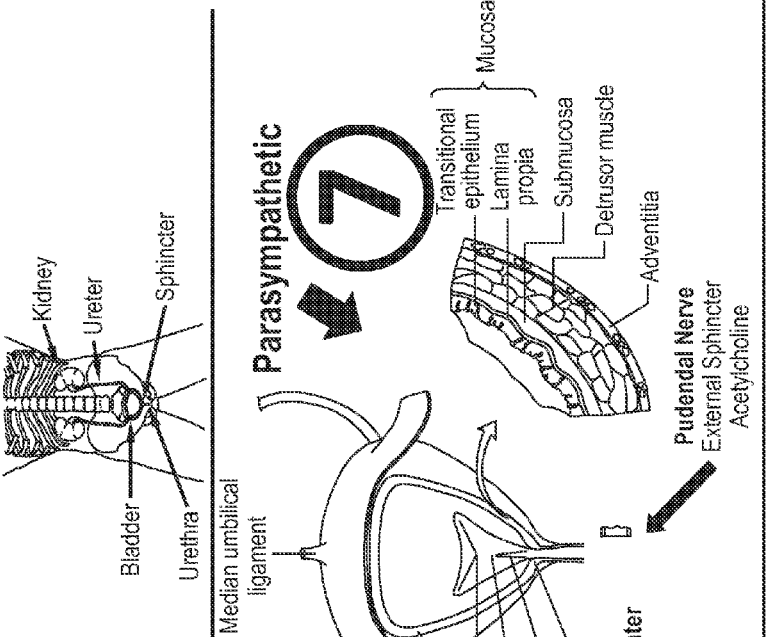
FIG. 23 illustrates a summary of pharmacologic rationale for bladder regulation with TC-5214. The area designated "1" illustrates are two identified brain regions, the pontine micturition center (PMC) and the paraventricular nucleus of the hypothalamus (PNH), which express α4β2 receptors contributing to the supraspinal inhibitory pathways of bladder contractility. This is consistent with the increased bladder contractility in anesthetized animals and in animals or human with spinal cord lesions interrupting these inhibitory controls of bladder contraction. An antagonist such as mecamylamine would therefore inhibit these inhibitory centers resulting in increased bladder activity. TC-5214, to the contrary, is expected to have little to no effects or could even be beneficial through positive allosteric modulation of the α4β2 NNR. The area designated "2" illustrates bladder afferents and efferents to and from the spinal cord as involving NMDA receptors (N1A and N2b) resulting in a positive feedback loop, increasing bladder contractility. NMDA antagonists inhibit bladder contractility. TC-5214 potently (10-30 nM) inhibits both of these NMDA receptors therefore resulting in interruption of the positive feedback loop, contributing to decreased detrusor activity. The area designated "3" illustrates the autonomic nervous system. Both sympathetic and parasympathetic nervous systems are implicated in regulating bladder contractility with relaxation through the sympathetic system (norepinephrine released from postganglionic sympathetic fibers) and contraction through the parasympathetic system (acetylcholine released at the target sites in the bladder through cholinergic parasympathetic fibers). The inhibition of sympathetic activity would inhibit bladder relaxation but these effects are expected to be minimal because TC-5214 will have little inhibitory effects at α3β4 (reference FIG. 14) and will be counteracted by the inhibition by TC-5214 of overactive parasympathetic fibers which exert a greater control of bladder contractility, namely a low dose inhibition of overactive parasympathetic will be greater than the inhibition of relaxation through sympathetic inhibition, thereby resulting in a net positive effect in overactive bladder. The area designated "4" illustrates the bladder and purinergic receptors. In addition to autonomic control, multiple receptors are present within the bladder. All the effects within the bladder are expected because of the present finding that TC-5214 is eliminated unchanged in the urine. Purinergic receptors. P2X2 and P2X3, are tightly linked to the nicotinic receptors present on the urothelium. There is a co-activation and co-inhibition through the α3β4 nicotinic receptors. Inhibition of α3β4 will result in co-inhibition of P2X receptors further decreasing detrusor overactivity. The area designated "5" illustrates that α6-containing nicotinic receptors are found in rodent bladder and are sensitive to TC-5214. Receptors expressed in oocytes were stimulated with acetylcholine alone or with and increasing concentrations of TC-5214. Lastly, the areas designated "6" and "7" illustrate the inhibition of sympathetic and parasympathetic activities with TC-5214.

No appreciable effect of vehicle control was observed, but the positive controls (MK-801) produced nearly complete inhibition of NR1NR2a receptors with little evidence of recovery immediately following wash-out consistent with the literature data. Blinded comparison of ketamine vs. TC-5214 at 100 nM showed comparable levels of plateau inhibition (−50%) with clear evidence for recovery following washout. Similar findings were made with NR1a-NR2B receptors. Individual traces at both NR1a-NR2A and NR1a-NR2B using TC-5214 at increasing concentrations of 3, 10, 30, 100, 300 nM (FIG. 17 through for to 21, respectively) illustrates the dose dependency of TC-5214 at both subtypes. In each graph, current traces (top) and normalized responses to control activation (Glutamate 10 µM-Glycine 1 µM alone) are shown. These data are summarized in FIG. 22 showing a complete inhibition of NR1a-NR2A and a partial inhibition of NR1a-NR2B and supporting the hypothesis that systemic exposure of TC-5214 in the efficacious range for inhibition of $\alpha3\beta4$ receptors (30-100 nM), will also result in partial inhibition of the NMDA receptors (NR1a-NR2A and NR1a-NR2B) thereby providing additional inhibition of excitatory spinal inputs to the bladder and increasing bladder intercontraction intervals.

Example 6

Exo-R-Mecamylamine (TC-5213) Toxicity Study: 28-Day Repeated Oral Toxicity Studies in Rats 1. Summary of TC-5213 28-Day Study in Rats The purpose of this study was to evaluate the potential toxicity of TC-5213 administered orally in Sprague Dawley rats for 4 weeks. Eighty rats (40/sex) were assigned to 4 groups of 10/sex/group. Test article in purified water or water (vehicle) alone were administered once daily via oral gavage at a dose volume of 10 mL/kg. The dose levels were 0, 1, 10, and 50 mg/kg/day. Animals were given TC-5213-23 orally (gavage) for 28 days except those given the test article at 50 mg/kg from Day 1 to 7, followed by a dose of 40 mg/kg/day on the subsequent 21 days. The dose levels were calculated based on the free base form of the test article.

Early deaths were observed at 50 mg/kg/day (4/10 males and 5/10 females died after three to seven doses) during the first week of dosing, thereby necessitating a dose reduction thereafter to 40 mg/kg. Distended urinary bladder, full of urine, was observed in early dead animals (3 males and 2 females).

Treatment-related clinical signs including decreased activity, decreased defecation, cold to touch, semi-closed eyes, dilated pupils, ocular discharge, tremors, and prostration were noted at 50 mg/kg/day during the first week of dosing. After the dose level was reduced to 40 mg/kg/day from Day 8, most of the signs were no longer observed. At ≥10 mg/kg/day, semi-closed eyes, dilated pupils, and decreased activity were observed in some rats. No test article related signs were observed at 1 mg/kg/day.

Statistically significant body weight losses were observed in both males and females throughout the whole 4-week dosing period at 50→40 mg/kg/day and in males during the first two weeks at 10 mg/kg/day. Significant decreases in the body weight and corresponding food consumption reductions were observed in males at the end of first week dosing and in females during the first 3 weeks dosing period at 50→40 mg/kg/day and in both males and females at the end of the first week dosing at 10 mg/kg/day.

No test article related changes in opthalmological examinations were observed at any dose levels.

At the end of the study, clinical pathology changes were observed at 50→40 mg/kg/day as following: slight increases in neutrophils; slight decreases in lymphocyte and platelets; slight increases in ALT, AST, and calcium (also observed at 10 mg/kg/day,), Total Cholesterol; slight decreases in potassium; slight decrease in PH of urine and slight increase in Urine Specific Gravity.

During the necropsy, decreased organ weights of prostate gland, seminal vesicles and thymus were observed at 50→40 mg/kg/day. These organ weight losses were considered stress related. No remarkable findings in survived animals during the necropsy. The No-Observed-Effect-Level (NOEL) was considered to be 1 mg/kg/day for both males and females in this study.

2. Comparison of TC-5213 and TC-5214 Toxicity in Rats

The toxicity of TC-5213 or TC-5214 was assessed in rats in a repeat oral dosing study for 28 or 30 days respectively. For both studies, the NOEL was 1 mg/kg/day. Similar slight clinical signs including pupil dilation, (semi-)closed eyes, and decreased activity were observed at 10 mg/kg/day for both compounds. However, TC-5214 did not produce any mortalities nor any histopathologic changes at doses up to and including 50 mg/kg/day. In contrast, daily oral administration of TC-5213 at dose levels of 50→40 mg/kg/day resulted in mortality, organ weight and/or microscopic changes in the testes, epididymides, prostate gland and seminal vesicles in the males; in the ovaries and vagina in the females.

Example 7

Oral Administration of Dexmecamylamine in Rat Model

A further study was conducted to evaluate the effects of TC-5214 on bladder function in awake, conscious Sprague Dawley rats. General surgical procedures and cytometric data collection have been previously described. Zhao, et al., *Impaired bladder function in aging male rats*, Urol. July 184(1):378-385, 2010.

Nine female Sprague Dawley rats received intravesical saline at a rate of 10 mL/hr. Following a 60-minute baseline evaluation, rats were administered dexmecamylamine at a dose of 1 mg/kg by oral gavage, a dose previously determined to be the "No Effect Dose" in safety pharmacology studies. Two hours following the oral administration of dexmecamylamine, cystometric parameters were collected over a period of one hour. Unexpectedly and surprisingly, dexmecamylamine produced statistically significant (Student paired-t test) increases in the micturition interval, bladder capacity, and micturition volume without producing detrimental changes in micturition pressure, bladder contraction amplitude, or bladder compliance relative to baseline values. Table 7 shows the changes in cystometric parameters following oral administration (gavage) of dexmecamylamine:

TABLE 7

| | micturition interval | Bcap | MV | RV (Bcap-MV) | BP (baseline) | TP | MP | IMP | SA (IMP-BP) | B compliance |
| --- | --- | --- | --- | --- | --- | --- | --- | --- | --- | --- |
| First 1H | 6.44 ± 1.24 | 1.04 ± 0.24 | 1.06 ± 0.21 | 0.06 ± 0.02 | 10.39 ± 1.96 | 23.27 ± 3.82 | 55.1 ± 5.53 | 16.94 ± 3.94 | 6.55 ± 2.01 | 0.11 ± 0.03 |
| Last 1H | 9.44 ± 1.87 | 1.58 ± 0.31 | 1.45 ± 0.28 | 0.09 ± 0.04 | 8.60 ± 1.10 | 23.3 ± 2.0 | 48.2 ± 4.54 | 15.6 ± 2.91 | 6.99 ± 2.57 | 0.13 ± 0.03 |

Figure 25:
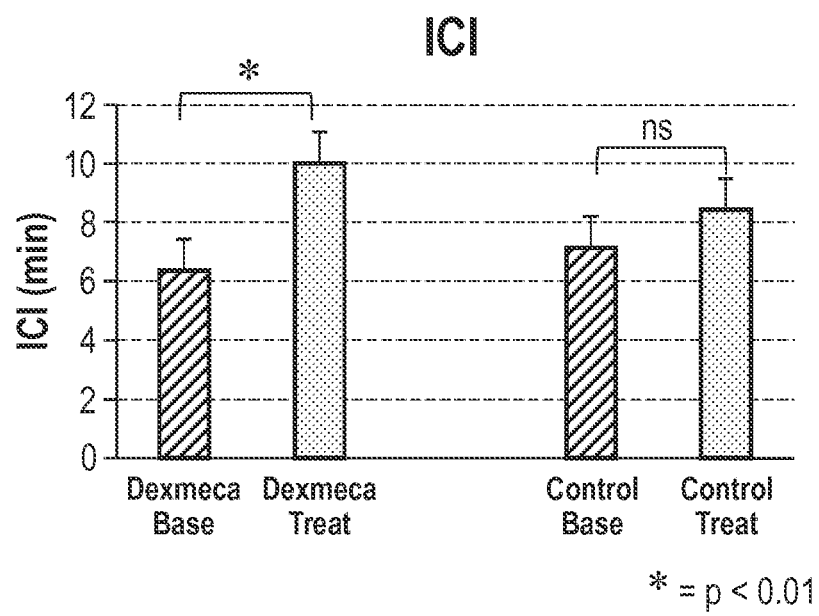
FIG. 25 shows the change in inter-contraction interval (ICI) after administration of dexmecamylamine compared to control. An alternative description for this measurement could be the change in micturition interval (minutes).

FIG. 25 shows the change in micturition interval (minutes) following oral administration (gavage) of dexmecamylamine. As noted herein, an alternative description of this parameter is a change in inter-contraction interval (ICI) after administration of dexmecamylamine compared to control. TC-5214 provided a statistically significant increase in ICI.

Figure 26A:
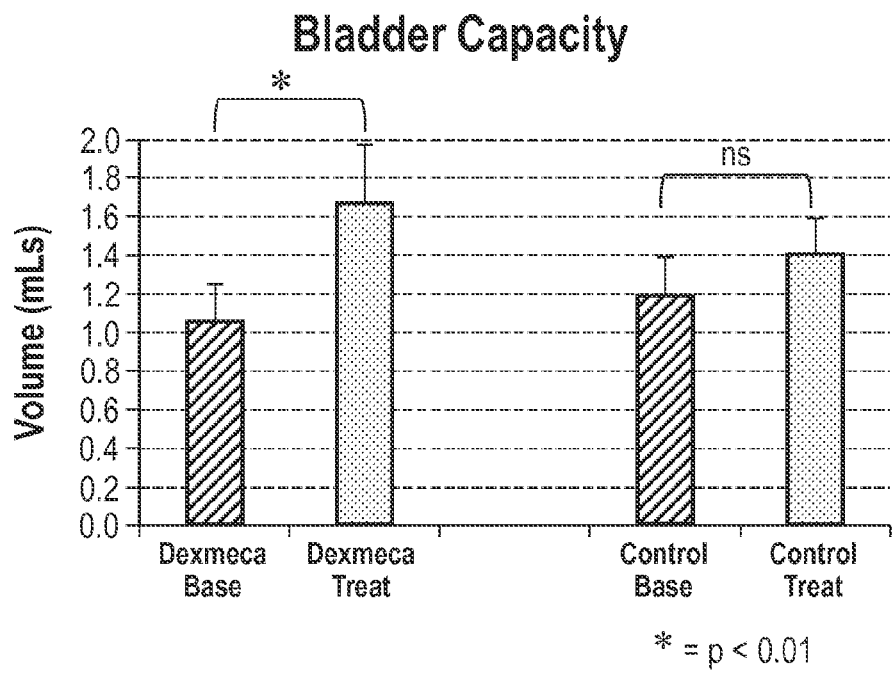
FIG. 26 shows the changes in bladder capacity (FIG. 26A) andmicturition volume (FIG. 26B) following oral administration (gavage) of dexmecamylamine compared to control.
Figure 26B:
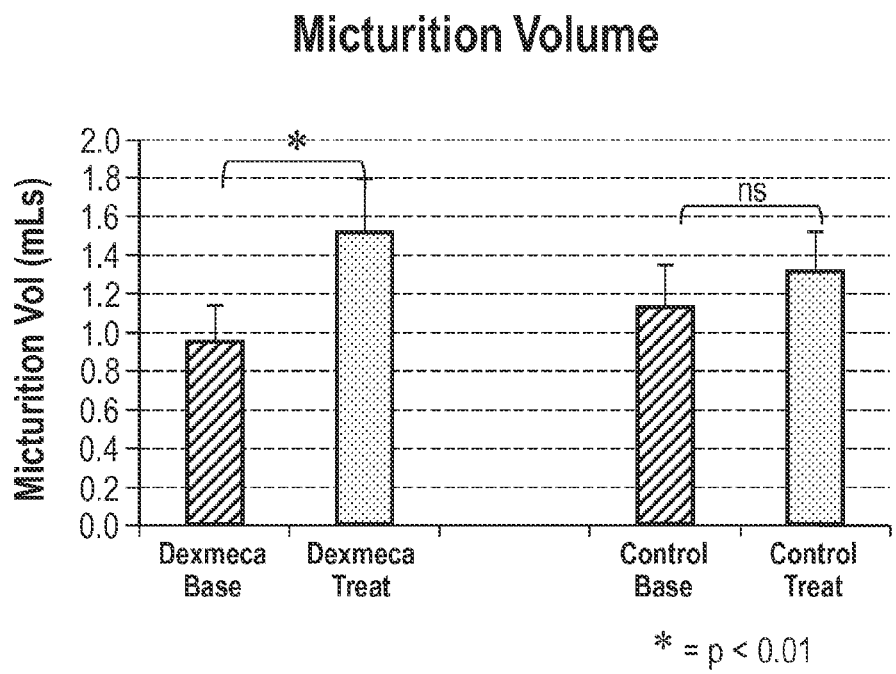

FIG. 26 shows the changes in bladder capacity (FIG. 26A) and micturition volume (FIG. 26B) following oral administration (gavage) of dexmecamylamine compared to control. TC-5214 provided a statistically significant increase in each of bladder capacity and micturition volume.

Figure 27:
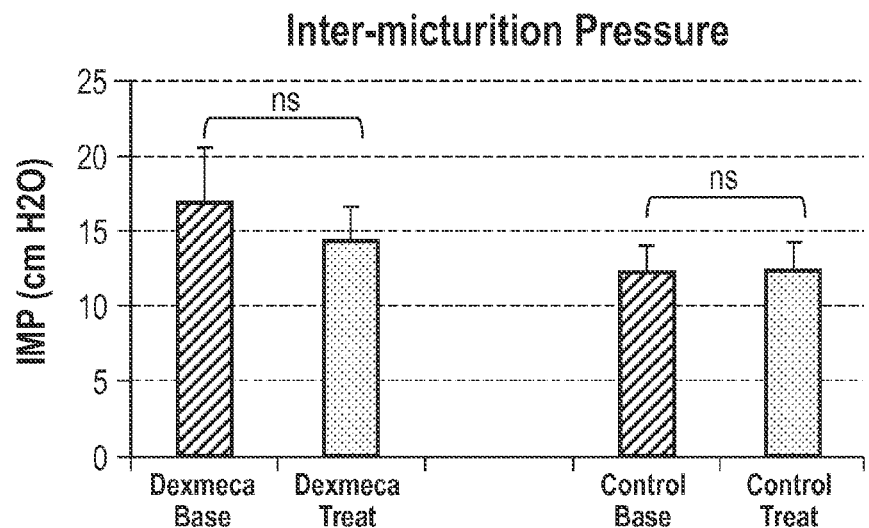
FIG. 27 shows the changes in inter-micturition pressure following oral administration (gavage) of dexmecamylamine compared to control.

FIG. 27 shows the change in inter-micturition pressure following oral administration (gavage) of dexmecamylamine compared to control.

Figure 28:
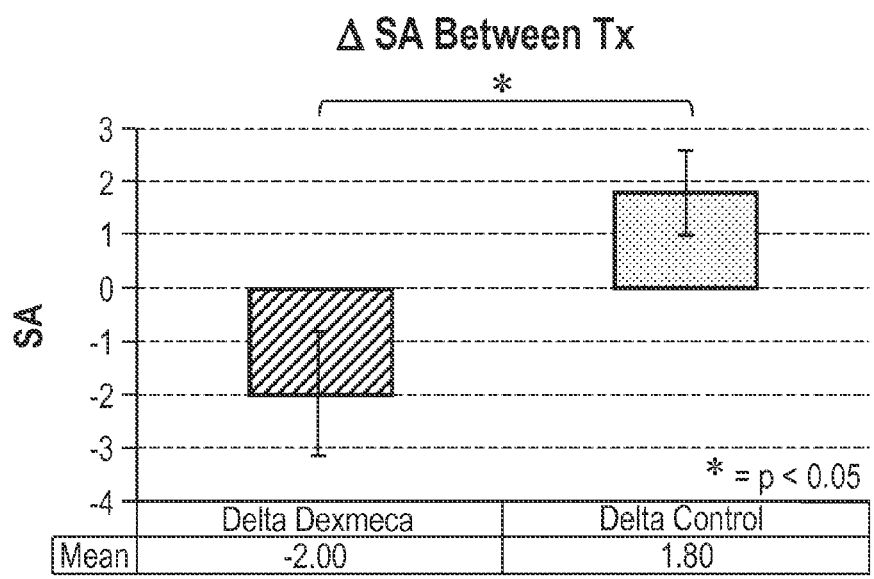
FIG. 28 shows the change in spontaneous activity following oral administration (gavage) of dexmecamylamine compared to control.

FIG. 28 shows the change in spontaneous activity, a surrogate for urge, following oral administration (gavage) of dexmecamylamine compared to control. TC-5214 provided a statistically significant differential in SA between treatment groups.

Figure 29:
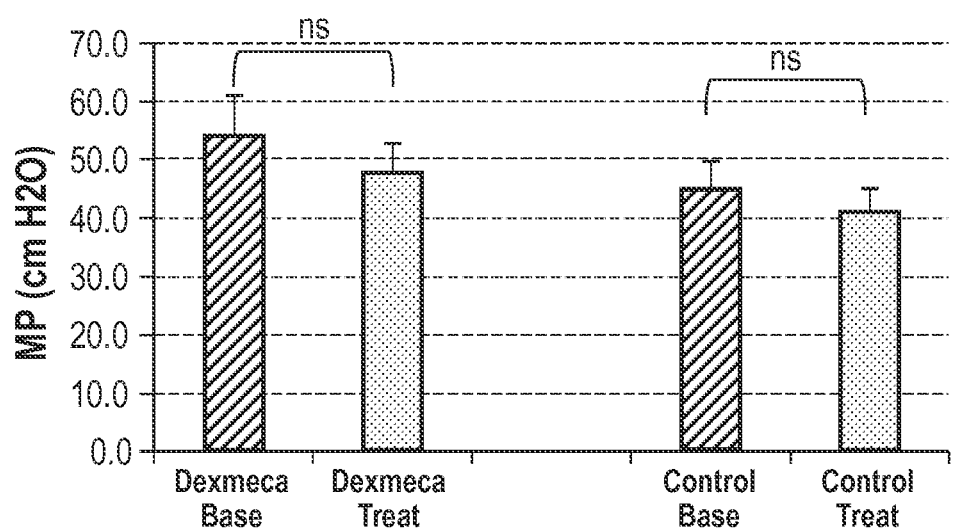
FIG. 29 shows the bladder contraction amplitude following oral administration (gavage) or decmecamylamine compared to control.
Figure 30C:
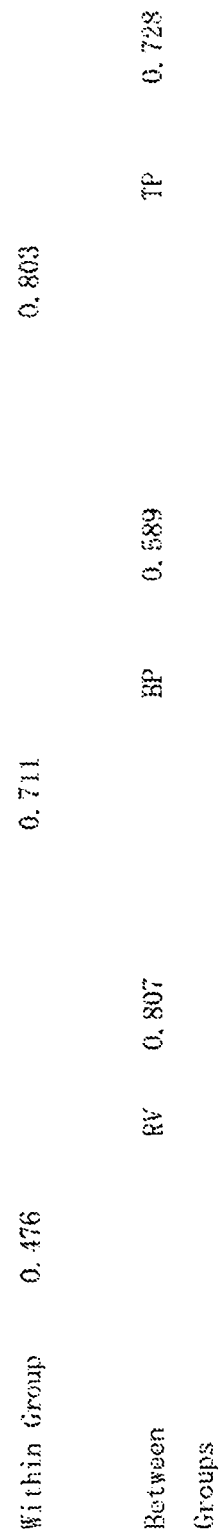

FIG. 29 shows the bladder contraction amplitude following oral administration (gavage) of decmecamylamine compared to control, namely that TC-5214 was placebo-like regarding amplitude of contraction.

FIGS. 30A-30G show tabulated data for bladder activity after administration of dexmecamylamine or control.

As these data demonstrate, administration of dexmecamylamine surprisingly, and in direct contrast to the results reported by Kaplan et al., has an insignificant effect on bladder contraction amplitude while creating a significant decrease in bladder spontaneous activity. For example, FIG. 29 illustrates that TC-5214 was placebo-like in the effect on the amplitude of contraction. As noted herein, this is in direct contrast to the findings associated with racemic mecamylamine by Kaplan et al.

The data further demonstrate, in particular FIG. 28, the surprising and unexpected effect of TC-5214 on SA, which is an approximate index of spontaneous bladder contractions between micturitions. This differential in SA is believed to be indicative of decreasing urge in a patient with overactive bladder. Reference is made to Hodges et al., *Voiding Pattern Analysis as a Surrogate for Cystometric Evaluation in Uroplakin II Knockout Mice*, The Journal of Urology, Vol. 179, 2046-2051, May 2008. These are significant and unexpected results given that bladder spontaneous activity may be considered as a surrogate for the urge to urinate in humans.

The oral administration of dexmecamylamine in the conscious rat model further supports the unexpected efficacy and favorable side effect profile of systemically administered dexmecamylamine to treat OAB. The decrease in the bladder spontaneous activity following oral administration of dexmecamylamine is consistent with a combination of: (1) inhibition of afferent signaling through inhibition of α3β4; and (2) inhibition of spinal activation of the bladder through NMDA receptors. A lack of effect on amplitude of contraction is unexpected and indicates that dexmecamylamine preferentially effects the urothelial afferent axis over the efferent PNS.

Example 8

Dexmecamylamine Oral Administration in Humans

FIG. 24 is a table showing rates of urinary tract infection (UTI) and urinary retention in human patients administered dexmecamylamine in a yet unpublished clinical trial for treatment of depression. Patients received orally administered dexmecamylamine tablets of 0.1 mg, 0.5 mg, 2 mg or 4 mg BID (twice daily). At the end of the trial period, the patients were evaluated and the rates of side effects, including urinary tract infection (UTI) and urinary retention, were recorded. This study confirmed that oral administration of dexmecamylamine to human subjects occurred without therapy-limiting side effects due to urinary retention.

Example 9

A Randomized, Double-Blind, Placebo-Controlled, Parallel Group, Fixed Dose Study to Evaluate the Efficacy, Safety, and Tolerability of Dexmecamylamine in the Treatment of Subjects with Overactive Bladder (OAB)

The following is a prophetic example of an intended clinical protocol to evaluate the efficacy, safety, and tolerability of dexmecamylamine in the treatment of human subjects with overactive bladder. Reference is made to Targacept Study Number TC-5214-23-CRD-003, herein incorporated by reference in its entirety.

Synopsis

| | |
|---|---|
| Name of Finished Product: Dexmecamylamine hydrochloride | Name of Active Substance: Dexmecamylamine |

Title of Study: A Randomized, Double-Blind, Placebo Controlled, Parallel Group, Fixed Dose Study to Evaluate the Safety, Tolerability, and Efficacy of Dexmecamylamine in the Treatment of Subjects with Overactive Bladder (OAB).
Co-Investigators: Michael Chancellor MD, Peter Sand MD
Study Period: Estimated screening expected to start April 2013; Expected completion June 2014
Phase of development: 2b study
Objective(s):
Primary:

To assess the efficacy of dexmecamylamine in the treatment of Overactive Bladder (OAB)

Figure 31:
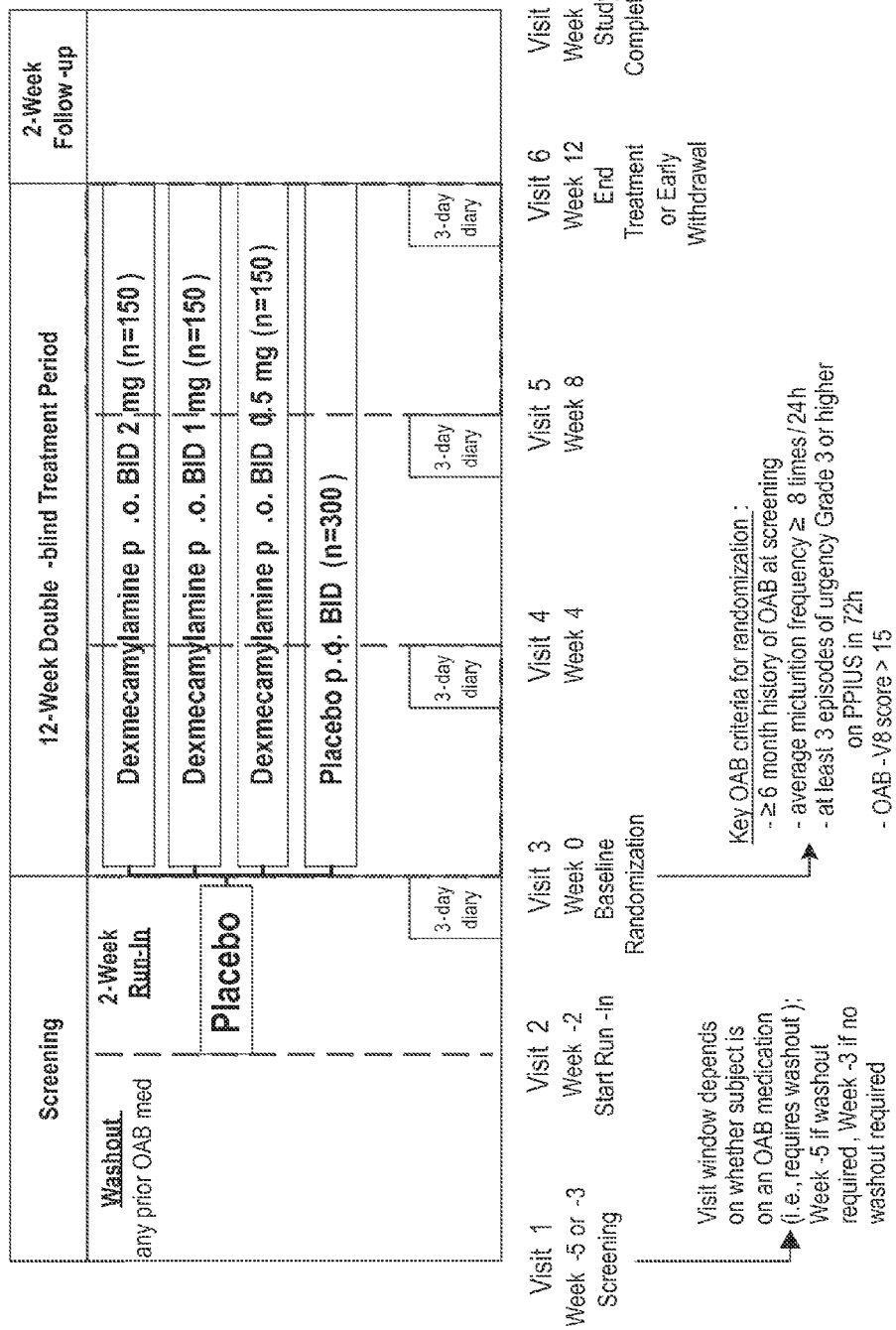
FIG. 31 is a graphical depiction of an overactive bladder clinical trial study. As shown, the length of study participation for a subject is about 17-19 weeks depending on whether a subject requires washout from OAB medications, namely a 3-5 week screening period that includes a 2 week washout, as needed, a 2 week single-blind placebo run-in, 12 weeks of double-blind treatment with 2 weeks of follow-up.

Secondary:

To assess the safety, tolerability and pharmacokinetic profile of dexmecamylamine in subjects with OAB Methodology: This is a randomized, double-blind, placebo-controlled, parallel group, fixed dose study.
Number of Subjects:

Sufficient subjects will be screened and complete a 2-week Run-In Period such that at least 750 total subjects will be randomized into the Double-Blind Treatment Period of the study. There will be 3 active arms (0.5 mg bid, 1 mg bid and 2 mg bid) with 150 subjects per arm and 1 placebo arm (placebo bid) with 300 subjects. The strategy of randomizing twice as many subjects to the placebo arm as to each active treatment arm was chosen to primarily avoid expectation bias. A subject's expectation that they will have an increased chance of receiving active treatment has been shown to increase the placebo response and hence decrease the ability to identify an efficacy signal in a number of studies in other therapeutic areas. In addition this approach results in a modest (6%) decrease in the total sample size required.
The target proportion of OAB "wet" subjects in the study will be at least 75%; however, randomization will not be stratified according to OAB type. An OAB "wet" subject is defined as one who had at least one UUI episode on the 3-day diary during the Run-In Phase. The proportion of OAB "wet" subjects to OAB "dry" subjects will be monitored and enrollment of OAB "dry" subjects may be limited during the study in an attempt to randomize at least 75% OAB "wet" subjects.
Study Overview:
Study Periods:

As shown in FIG. 31, the length of study participation for a subject is about 17-19 weeks depending on whether a subject requires washout from OAB medications (a 3-5 week screening period that includes a 2 week washout, as needed, a 2 week single-blind placebo run-in, 12 weeks of double-blind treatment with 2 weeks of follow-up). There are 7 visits with a ±3 day visit window, except for subjects requiring washout of OAB medications the Run-In Visit (Visit 2, Week −2) should occur after at least a 2

| Name of Finished Product: Dexmecamylamine hydrochloride | Name of Active Substance: Dexmecamylamine |
|---|---| week washout. Subjects on an OAB medication will have a Screening Visit (Visit 1) on about Week −5. This will allow sufficient time to obtain final central laboratory results prior to initiation of the washout on Week −4. Subjects not on OAB medications at Visit 1 should have their Screening Visit about 1 week (Week −3) prior to the initiation of the Run-In Period which will begin for all subjects on Week −2 (Visit 2).

Study assessments:

At the Screening Visit (Visit 1) following informed consent, initial eligibility will be verified per the inclusion/exclusion criteria before blood is drawn for safety labs. Key initial eligibility criteria will include a verified and documented history of OAB of at least 6 months duration, urge predominant incontinence as verified with the 3 Incontinence Questions (3IQ) questionnaire, and a post-void residual urine (PVR) of <150 mL. Subjects with exclusionary laboratory results have the opportunity of a repeat test and subjects may be enrolled, at the discretion of the investigator, if the repeat test is within the eligible range and is consistent with the subject's clinical picture. All subjects, who meet the preliminary eligibility criteria at the Screening Visit and do not have exclusionary abnormalities in the laboratory tests, will washout of their current OAB medication if on an OAB medication, and all subjects will return for Visit 2 about 2 weeks (±3 days) before the Baseline visit (Week 0, Visit 3).

At the Run-In (Visit 2, Week −2) the appropriate washout of OAB medications will be confirmed and subjects must have a sufficient degree of bother based on a score of greater than 15 on the OAB-V8 questionnaire. Subjects who continue to be eligible will be trained on the use of the bladder diary, and study drug for the placebo Run-In Period will be distributed and the subject instructed on how and when to take the study drug. Subjects will complete a diary on the last 3 days of the Run-In Period. Subjects will take 1 tablet of study drug in the AM and 1 tablet in the PM during the Run-In Period and subjects will begin dosing the evening of Visit 2. Subjects will record in their bladder diary the time of each micturition and each episode of incontinence. In addition on day 1 of diary data collection, subjects will measure and record the volume of each voluntary micturition over a 24 hr period. Subjects who forget to complete the void volume on diary day 1 or cannot measure void volume on diary day 1 can complete this task on diary day 2 or 3.

Following the two-week Run-In Period, subjects will return to the clinic for Visit 3 (Baseline, Week 0)) during which, if eligible, they will have baseline assessments and be randomized into the study and given blinded study drug. Prior to randomization, subjects must have demonstrated during the Run-In Period the ability to appropriately take study drug and complete the diary (see inclusion criteria) and must continue to have a sufficient degree of bother based on a score of greater than 15 on the OAB-V8 questionnaire. Following randomization, subjects will return every 4 weeks (Visits 4-6, Weeks 4, 8, and 12) for a safety evaluation including adverse even assessment, evaluation of study drug compliance, efficacy-related assessments using the following instruments: Patient Perception of Bladder Condition (PPBC); Clinical Global Impression of Improvement (CGI-I); Overactive Bladder Questionnaire (OABq), a disease specific quality of life and bother questionnaire; the Urgency Questionnaire, and collection of bladder diaries, and to obtain additional Study drug supplies for the following 4 weeks. Subjects will complete a bladder diary the 3 days prior to each visit. There will be a Follow-up visit (Visit 7, Week 14) 2 weeks after the end of double-blind treatment. All subjects will have a post void residual (PVR) urine volume ultrasound evaluation at screening, baseline and during each visit during the Double-Blind Treatment Period, except Visit 5 (Week 8). The Columbia Suicide Severity Rating Scale (CSSRS) will be completed at all visits except Run-In Visit (Visit 2, Week −2). Dosing and the number and timing of assessments will be slightly different between PK and Non-PK subjects during the Double-Blind Treatment Period to accommodate PK sampling (see Time and Events Schedule). All subjects will take 1 tablet of double-blind study drug in the AM and 1 tablet in the PM during the Double-Blind Treatment Period without regards to meal times. PK subjects will dose in the clinic at each visit during the Double-Blind Treatment Period and therefore visits will generally be required to occur in the morning. Non-PK subjects are not required to dose in the office and there is no constraint on the time of day a visit can occur. Non-PK subjects will take their first dose of blinded study drug in the evening of the day of randomization.

Population Pharmacokinetic Substudy:

About 200 PK subjects will participate in a population pharmacokinetic (PK) sub-study. Sparse population blood samples to document plasma exposure of dexmecamylamine will be collected at Week 0, (Visit 3, Baseline), Week 4 (Visit 4) and Week 12 (Visit 6, End of Double-Blind Treatment Period). Plasma samples at these visits will be collected at pre-dose, at least 2 hours after dosing, and at least 5 hours after dosing. A urine sample for dexmecamylamine concentration determination will also be collected at these visits at 3 hours post-dose. Sites enrolling PK subjects will be required to randomize at least two PK subjects prior to enrolling non-PK subjects or unless otherwise agreed by the Sponsor. Once this criterion is met or enrollment of about 200 PK subjects is complete, whichever happens first, a site may also enroll non-PK subjects.

-continued

| Name of Finished Product: Dexmecamylamine hydrochloride | Name of Active Substance: Dexmecamylamine |

Inclusion Criteria:

At the Screening visit (Visit 1, Week −3, or −5 if washout of OAB drugs is required), subjects must meet all of the following criteria:
1. Subjects must have a documented medical history (e.g., chart note or letter from subject's physician) of overactive bladder for ≥6 months. (Site must confirm at least a 6 month history through, for example, chart note or letter from subject's physician, direct knowledge of subject's OAB history, review of pharmacy prescription record or from dates on subject's OAB medication bottle or others as determined).
2. Males or females aged ≥18 years.
3. Body Mass Index (BMI) ≤38.
4. Women of childbearing potential must be currently using or willing to use an acceptable form of contraception as specified in the protocol.
5. Able to understand the informed consent, and provide written informed consent.
6. Capable of walking unassisted to use the bathroom and able to measure voided urine volume and complete the diary without assistance.
7. If the subject is currently being treated with an OAB medication, the subject is willing to discontinue OAB medications while participating in this study.
8. Subjects should meet all applicable inclusion criteria and not meet any applicable exclusion criteria to progress into the next phase.

Prior to the Run-In Visit (Visit 2, Week −2), the results of all laboratory assessments unavailable at Screening Visit should be evaluated for continued eligibility and tests repeated, as necessary. At the Run-In Visit (Visit 2, Week −2), subjects must meet the following criteria to progress:
1. Confirm that any OAB medication has been discontinued at least 2 weeks prior to visit.
2. Understand how to fill out the bladder diary.
3. Have a score of greater than 15 on the OAB-V8 screening questionnaire to indicate sufficient OAB symptom bother.
4. Subjects should continue to meet all applicable inclusion criteria and not meet any applicable exclusion criteria to progress into the next phase.

At the Baseline visit (Visit 3, Week 0) subjects must meet the following criteria prior to randomization:
1. Subject was compliant with completing the 3-day bladder diary as instructed and at least 80% compliant with taking the study drug during the Run-In Period.
2. Based on the 3-day Run-In bladder diary all subjects must meet either criterion "a" or "b" below. OAB "wet" and "dry" classification is based on the presence or absence, respectively, of UUIs in the Run-In diary.
    a. If the subject is classified as OAB "dry" there was an average of ≥8 micturitions per 24 hours in the Run-In diary and no UUI episodes in the Run-In diary.
    b. If the subject is classified as OAB "wet" there were ≥3 UUI episodes over the 3-day Run-In diary period and an average of ≥8 micturitions per 24 hours
3. Have a bother score of more than 15 on the OAB-V8 scale.
4. Fulfilled all the inclusion and none of the exclusion criteria.

Exclusion Criteria:

To participate in the study, subjects must not meet any of the following criteria:
1. Receiving any drug or non-drug treatment for OAB except as noted elsewhere after the Screening visit including physical therapy and electrical or magnetic stimulation. Bladder training programs and behavior modifications for OAB are allowed but must have started at least 3 months prior to screening and must not change during the study period.
2. Diagnosis of a neurological disease affecting bladder function (including Parkinson's disease, demyelinating disease such as multiple sclerosis, transverse myelitis, spinal cord injury, brain or spinal tumor, stroke, diabetic neuropathy, spina bifida, caudal agenesis, motor neuron disease).
3. Incontinent subjects where the incontinence is not predominantly urge incontinence based on the 3IQ questionnaire (if questions 1a is checked, question 3b must be checked [i.e., leaked most often due to urge . . .]).
4. Insensate incontinence, overflow incontinence or incontinence due to urinary fistula.
5. History of incomplete bladder emptying, bladder outflow obstruction or PVR bladder urine volume >150 mL as determined by a post-void bladder ultrasound on Screening (Visit 1) or Baseline (Visit 3).
6. Males with benign prostatic hyperplasia or with a prostate-specific antigen (PSA) ≥4 ng/mL at Visit 1(unless a negative biopsy within one year of the Screening Visit) or a significantly rising PSA based on the investigator's opinion if historical data is available.
7. Other urinary tract pathology such as malignancy, ureteric reflux, bladder stone, uninvestigated hematuria, urethral stricture, or cystitis.
8. Urinary tract infection (UTI) or history of recurrent UTIs (2 uncomplicated UTIs in 6 months or 3 positive cultures within the preceding 12 months).

| Name of Finished Product: Dexmecamylamine hydrochloride | Name of Active Substance: Dexmecamylamine |
|---|---|

9. Polyuria (>3000 mL/24 hr).
10. Nocturia due to renal insufficiency or heart failure.
11. Diuretics or hormone replacement therapy initiated or modified within 3 months of screening.
12. Prior treatment with intravesical or intraprostatic botulinum toxin in the last 2 years or planned treatment during the study.
13. Impaired renal function or an estimated creatinine clearance (Cockcroft and Gault equation) of less than 30 mL/min
14. An ALT, AST or alkaline phosphatase ≥2x ULN or bilirubin ≥1.5x ULN.
15. Women who are pregnant, lactating/nursing or plan to become pregnant, or are postpartum (<1 year).
16. Women with a uterovaginal prolapse that is visible at the introitus.
17. Past or present history of clinically significant obstructive gastrointestinal disease.
18. Myasthenia gravis.
19. Angle closure glaucoma.
20. Pelvic or pelvic floor surgery within 6 months prior to screening.
21. Surgery (minor outpatient allowed) of any kind within 3 months of Screening or planned during the study.
22. Prior implantation of interstim electrodes or vaginal surgical mesh.
23. Presence of an active infection except for minor skin infections.
24. Presence of a clinically significant medical condition that has been unstable, including clinically significant changes in treatment, within 3 months prior to patient screening (Visit 1) or a clinically significant uncontrolled medical condition at any time during the screening process (after Visit 1 to Visit 3).
25. Substance abuse (i.e., drug or alcohol) at least 6 months prior to Screening (Visit 1).
26. History or evidence of clinically significant cardiac abnormality as measured by Screening ECG. Presence of hepatic disease, renal disease, clinically important pulmonary disease, or any other medical illness deemed clinically important enough for subject prohibition into the study by the Investigator.
27. Presence of clinically significant abnormalities in laboratory findings, physical exam findings or vital signs.
28. History of suicide attempts or self-injury in the past 12 months of screening (Visit 1) or no more than minimal suicidal ideation (thoughts of suicide but nonspecific: no method, intent or plan).
29. Participated in an investigational drug trial within 3 months of Visit 1.
30. Subject plans on donating blood during the trial.
31. Previous participation in a clinical study of dexmecamylamine (TC-5214).

Test Product(s), Dose, and Mode of Administration, Batch Number(s):

During the placebo Run-In Period and Double-blind Treatment Periods, subjects will be instructed to take study drug twice daily (once in the AM and once in the PM, separated by approximately 12 hours) throughout the study period. During the Run-In Period all subjects will take placebo and the study drug will only be blinded to the subject (single-blind). During the Double-Blind Treatment Period subjects will be randomized to treatment. During this period subjects will receive one of 4 treatments: 3 active arms (0.5 mg bid, 1 mg bid and 2 mg bid) with 150 subjects per arm, and 1 placebo arm (bid) with 300 subjects. Study drug will be taken on an outpatient basis, except for subjects participating in the population PK sub-study. These subjects will be required to dose at each clinic visit.
The active pharmaceutical ingredient in the drug product that will be used in this study is dexmecamylamine hydrochloride. All dosing will be based on the free base equivalent. The term dexmecamylamine will be used to describe both the active investigational product and active moiety.
Investigational: Dexmecamylamine: 0.5 mg, 1 mg, and 2 mg tablets, batch numbers HZPK, KHVF, and HZPN, respectively.
Control: Matching placebo, batch number HZPG.
Duration of Treatment:

The length of study participation for a subject is about 17-19 weeks depending on whether a subject requires washout from OAB medications (a 3-5 week screening period that includes a 2 week washout, as needed, and a 2 week placebo run-in, and 12 weeks of double-blind treatment with 2 weeks of follow-up)
Concomitant Medication Restrictions:

Use of any medication indicated or used to treat OAB (including off-label use) will be washed out during the period between Visit 1 and 2. This may include the following drugs for OAB treatment: tolterodine, solifenacin, trospium, darifenacin, fesoterodine, mirabegron, oxybutynin, atropine, dicyclomine/dicycloverine, emepromium, glycopyrronium, flavoxate, isopropamide, oxyphencyclimine, propantheline, propiverine. Drugs with known off-label use for treating OAB may be used if not prescribed to treat a subject's OAB (e.g., tricyclic antidepressant for depression is allowed but cannot be used if prescribed for OAB). Prior treatment with intravesical or intraprostatic botulinum toxin in the last 2 years prior to screening (Visit 1) and during the study is prohibited.

| Name of Finished Product: Dexmecamylamine hydrochloride | Name of Active Substance: Dexmecamylamine |
|---|---|

Criteria for Evaluation:
Efficacy Evaluation:
Co-Primary

Change from baseline in micturition frequency per 24 hours to Week 12.
    [Micturition: Any voiding episode recorded by the patient as "urinated" either with or without incontinence.]
    Change from baseline in urge urinary incontinence episodes per 24 hours to Week 12.

Key Secondary

Change from baseline in the volume voided per micturition to Week 12

Secondary

Change from baseline in micturition frequency per 24 hours at Week 4 and at Week 8
    Change from baseline in urge urinary incontinence episodes per 24 hours at Week 4 and at Week 8
    Change from baseline in urgency episodes per 24 hours at Weeks 4-12
    Change from baseline in the volume voided per micturition at Week 4 and at Week 8
    Change from baseline in nocturia per 24 hours at Weeks 4-12 [Nocturia: A micturition that wakes the subject from sleep between the time the subject went to bed and the time the subject planned to get up.]
    Clinical Global Impression of Improvement (CGI-I) at Weeks 4-12
    Change from baseline in Patient Perception of Bladder Condition (PPBC) at Weeks 4-12
    Change from baseline in the Urgency Questionnaire at Weeks 4-12
    Change from baseline in disease specific quality of life (OABq) at Weeks 4-12

Safety parameters

Safety and tolerability will be evaluated throughout the study (see the Time and Events Schedule for details).
Adverse events will be recorded throughout the study
Statistical Methods:
Efficacy:

This sample size is based on a fixed sequence strategy to deal with the multiplicity issue for the three active doses of dexmecamylamine. Based on this strategy, we will compare the largest dose of dexmecamylamine (2 mg bid) to placebo for the co-primary endpoints at the alpha = 0.05 level. If both co-primary endpoints are significant at the 0.05 level for this dose, the same comparisons will be performed for the 1 mg bid dose. If both co-primary endpoints are significant at the 0.05 level for this dose, the same comparisons will be performed for the 0.5 mg bid dose.
Pharmacokinetics:

Approximate trough (Cmin) and maximal (Cmax) concentrations will be presented by dose with descriptive statistics. The pharmacokinetic data may be used in a cross-study population pharmacokinetic analysis that may be presented in a separate report at a later date.
Data permitting, urine concentrations of dexmecamylamine will be correlated with the treatment assignment of the subjects as well as with the data from the bladder diaries and other instruments from of each subject.
Safety:

All subjects who are randomly assigned to a treatment and receive at least one dose of the study drug will be included in the safety and tolerability analysis. Baseline for all laboratory evaluations, post void residual (PVR) volume, vital signs, and 12-lead ECG measurements will be defined as the last evaluation done before the first study drug administration. Safety will be evaluated by examining the incidence and type of adverse events, including reports of suicidality, urinary retention, and changes in clinical laboratory test values, physical examination results, 12-lead ECGs, and vital signs measurements from the Screening Period through study completion.

| | Phase | | | | | | |
|---|---|---|---|---|---|---|---|
| | Screening | Washout | Run-In | Double Blind Treatment | | | | Follow-up |
| | Visit | | | | | | | |
| | 1 | | 2 | 3 | 4 | 5 | 6 | 7 |
| | Study Week (Day) | | | | | | | |
| | Week −5 or −3[A] (Days −35 or −21) | Week −4 (Day −28) (only subjects on OAB med) | Week −2 (Day −14) | Baseline Week 0 (Day 0) | Week 4 (Day 28) | Week 8 (Day 56) | End Treatment/ Early Withdrawal Week 12 (Day 84) | Week 14 (Day 96) |
| Screening | | | | | | | | |
| Informed Consent | X | | | | | | | |
| Demography | X | | | | | | | |
| Medical history and Dx of OAB | X | | | | | | | |
| Inclusion/exclusion | X | | X | X | | | | |
| Safety Procedures | | | | | | | | |
| Physical Examination | X | | | $X^B$ | $X^B$ | $X^B$ | $X^B$ | $X^{B,C}$ |
| Adverse Events | | | | Continuous | | | | |
| Concomitant Medications | | | | Continuous | | | | |
| CSSRS | X | | | X | X | X | X | X |
| Drug/alcohol screen | X | | | | | | X | |
| Safety Lab specimen collection | X | | | X | X | X | X | $X^C$ |
| Urine pregnancy test | X | | | X | | | X | |
| Study Treatment/General | | | | | | | | |
| Reminder to start washout (only subjects on OAB med) | | X | | | | | | |
| Study Drug Dosing | | | | X | X | X | X | |
| Dispense Study Drug | | | | | | | | |
| Run-in | | | X | | | | | |
| Blinded drug | | | | X | X | X | | |
| Collect unused study drug | | | | X | X | X | X | |
| Randomization | | | | X | | | | |
| Efficacy Procedures | | | | | | | | |
| 3IQ | X | | | | | | | |
| OAB-V8 | | | X | X | | | | |
| PPBC | | | | X | X | X | X | |
| CGI-I | | | | | X | X | X | |
| Urgency Questionnaire | | | | X | X | X | X | |
| OABq | | | | X | X | X | X | |
| OAB Diary | | | | | | | | |
| Dispense OAB Diary materials | | | X | X | X | X | | |
| Diary completion subject reminders prior to each visit | | | | X | X | X | X | |
| Collect/review previous OAB Diary with subject | | | | X | X | X | X | |
| Non-PK subjects | | | | | | | | |
| Bladder Scan for post void residual | X | | | X | X | | X | |
| Vital Signs (BP supine, pulse, temp) | X | | | X | X | X | X | $X^C$ |
| Orthostatic BP | | | | X | | | X | |
| ECG | X | | | X | X | | X | $X^C$ |
| Dexmecamylamine random urine sample | | | | X | X | | X | |
| Population PK subjects | | | | ↓ <------- Dose in the clinic -------> ↓ | | | | |
| In-Clinic Dosing | | | | X | X | X | X | |
| Bladder Scan for post void residual (predose) | X | | | X | X | | X | |
| Vital Signs (BP supine, pulse, temp) | X | | | $2X^D$ | X | X | $2X^D$ | $X^C$ |
| Orthostatic BP | | | | $2X^D$ | | | $2X^D$ | |
| ECG | X | | | $2X^D$ | X | | $2X^D$ | $X^C$ |
| Dexmecamylamine 3-hour post-dose urine samples | | | | X | X | | X | |
| Dexmecamylamine plasma samples | | | | $3X^E$ | $3X^E$ | | $3X^E$ | |

A - Week −5 for subjects on OAB medication, Week −3 for subjects not on an OAB medication
B - abbreviated physical
C - only required if clinically significant abnormality at previous visit
D - predose and just prior to collection of ≥2 hr post-dose PK plasma sample
E - 3 samples: predose, ≥2 hrs and ≥5 hr post-dose

STUDY DRUG: Dexmecamylamine (TC-5214)

STUDY NUMBER: TC-5214-23-CRD-003
VERSION: ORIGINAL
EFFECTIVE DATE: 12 MARCH 2013

A RANDOMIZED, DOUBLE-BLIND, PLACEBO-CONTROLLED, PARALLEL-GROUP, FIXED-DOSE STUDY TO EVALUATE THE EFFICACY, SAFETY, AND TOLERABILITY OF DEXMECAMYLAMINE IN THE TREATMENT OF SUBJECTS WITH OVERACTIVE BLADDER (OAB)

Sponsor: Targacept, Inc.
100 North Main Street, Suite 1510
Winston-Salem, North Carolina 27101-4072
USA

1. SYNOPSIS

| Name of Company: Targacept, Inc. | Name of Finished Product: Dexmecamylamine hydrochloride | Name of Active Substance: Dexmecamylamine |
|---|---|---|
| Title of Study: A Randomized, Double-Blind, Placebo-Controlled, Parallel-Group, Fixed-Dose Study to Evaluate the Safety, Tolerability, and Efficacy of Dexmecamylamine in the Treatment of Subjects with Overactive Bladder (OAB). |||
| Co-Investigators: |||
| Study Period: Estimated screening expected to start April 2013; Expected completion June 2014 |||
| Phase of Development: 2b study |||
| Objective(s):<br>Primary:<br>• To assess the efficacy of dexmecamylamine in the treatment of Overactive Bladder (OAB)<br>Secondary:<br>• To assess the safety, tolerability and pharmacokinetic profile of dexmecamylamine in subjects with OAB |||
| Methodology: This is a randomized, double-blind, placebo-controlled, parallel-group, fixed-dose study. |||
| Number of Subjects:<br>Sufficient subjects will be screened and complete a 2-week Run-In Period such that approximately 750 total subjects will be randomized into the Double-Blind Treatment Period of the study. There will be 3 active arms (0.5 mg twice daily (*bid*), 1 mg *bid* and 2 mg *bid*) with 150 subjects per arm and 1 placebo arm (placebo *bid*) with 300 subjects. The strategy of randomizing twice as many subjects to the placebo arm as to each active treatment arm was chosen primarily to avoid expectation bias. A subject's expectation that they will have an increased chance of receiving active treatment has been shown to increase the placebo response and hence decrease the ability to identify an efficacy signal in a number of studies in other therapeutic areas. In addition this approach results in a modest (6%) decrease in the total sample size required.<br><br>The target proportion of overactive bladder (OAB) "wet" subjects at baseline, based on the presence of urinary urge incontinence (UUI) episodes in the Diary in the Run-In Period, will be at least 75%; however, randomization will not be stratified according to OAB type. The proportion of randomized OAB "wet" subjects to OAB "dry" subjects will be monitored and the screening of OAB "dry" subjects may be limited during the study in an attempt to randomize at least 75% OAB "wet" subjects. It is anticipated that the study population will be primarily women. The percentage of males enrolled in the study will be monitored and may be limited to 20% or less. |||
| Study Overview:<br>Study Periods:<br>The length of study participation for a subject is about 17-19 weeks depending on whether a subject requires washout from OAB medications (a 3-5 week Screening Period that includes a 2-week washout, as needed, a 2-week, single-blind placebo Run-In Period, a 12-week Double-Blind Treatment with a 2-week Follow-up Period. There are 7 visits with a ± 3 day visit window except for subjects requiring washout of OAB medications the Run-In Visit (Visit 2, Week -2) should occur after at least a 2 week washout. Subjects on an OAB medication will have a Screening Visit (Visit 1) on about Week -5. This will allow sufficient time to obtain final central laboratory results prior to initiation of the washout on Week -4. Subjects not on OAB medications at the Screening Visit should have their Screening Visit about 1 week (Week -3) prior to the initiation of the Run-In Period which will begin for all subjects on Week -2 (Visit 2). |||

| Name of Company: | Name of Finished Product: | Name of Active Substance: |
|---|---|---|
| Targacept, Inc. | Dexmecamylamine hydrochloride | Dexmecamylamine |

Schedule:

- Screening | 12-Week Double-blind Treatment Period | 2-Week Follow-up
- Washout: any prior OAB med
- 2-Week Run-In
- Dexmecamylamine p.o. BID 2 mg (n=150)
- Dexmecamylamine p.o. BID 1 mg (n=150)
- Dexmecamylamine p.o. BID 0.5 mg (n=150)
- Placebo p.o. BID (n=300)
- 3-day diary (at Visits 3, 4, 5, 6)

Visits:
- Visit 1: Week -5 or -3, Screening
- Visit 2: Week -2, Start Run-In
- Visit 3: Week 0, Baseline Randomization
- Visit 4: Week 4
- Visit 5: Week 8
- Visit 6: Week 12, End Treatment or Early Withdrawal
- Visit 7: Week 14, Study Completion Screening Visit timing depends on whether subject is on an OAB medication (i.e., requires washout); Week -5 if washout required, Week -3 if no washout required

Key OAB criteria for randomization:
- ≥ 6 month history of OAB at screening
- One of the following based on Run-In diary:
  - if OAB "dry": an average of ≥ 8 micturitions per 24 hours and no UUI episodes
  - If OAB "wet": ≥ 3 UUI episodes over the 3-day Run-In diary period and an average of ≥ 8 micturitions per 24 hours.
- OAB-V8 score > 15

Study Assessments:

At the Screening Visit (Visit 1, Week -3, or -5 if washout of OAB medications is required) following informed consent, initial eligibility will be verified per the inclusion/exclusion criteria before blood is drawn for safety labs. Key initial eligibility criteria will include a verified and documented history of OAB of at least 6 months duration, if the subject has urinary incontinence it is urge predominant incontinence as verified with the 3 Incontinence Questions (3IQ) questionnaire, and a post-void residual urine (PVR) of < 150mL. Subjects with exclusionary laboratory results have the opportunity of a repeat test and subjects may be enrolled, at the discretion of the investigator, if the repeat test is within the eligible range and is consistent with the subject's clinical picture. All subjects, who meet the preliminary eligibility criteria at the Screening Visit and do not have exclusionary abnormalities in the laboratory tests, will washout of their current OAB medication if on an OAB medication, and all subjects will return for Visit 2 about 2 weeks (± 3 days) before the Baseline Visit (Visit 3, Week 0).

At the Run-In Visit (Visit 2, Week -2) the appropriate washout of OAB medications will be confirmed and subjects must have a sufficient degree of bother based on a score of greater than 15 on the Overactive Bladder Questionnaire-V8 (OAB-V8) questionnaire. Subjects who continue to be eligible will be trained on the use of the Diary, and study drug for the placebo Run-In Period will be dispensed and the subject instructed on how and when to take the study drug. Subjects will complete a Diary on the last 3 days of the Run-In Period. Subjects will take 1 tablet of study drug in the AM and 1 tablet in the PM during the Run-In Period and subjects will begin dosing the evening of the Run-In Visit. Subjects will record in their Diary the time of each micturition episode and the time of each incontinence episode and whether the leak was associated with or without urge. In addition on Day 1 of diary data collection, subjects will measure and record the volume of each voluntary micturition over a 24 hr period. Subjects who forget to complete the void volume on Diary Day 1 or cannot measure void volume on Diary Day 1 can complete this task on Diary Day 2 or 3.

| Name of Company: | Name of Finished Product: | Name of Active Substance: |
|---|---|---|
| Targacept, Inc. | Dexmecamylamine hydrochloride | Dexmecamylamine |

Following the 2-week Run-In Period, subjects will return to the clinic for the Baseline Visit (Visit 3, Week 0) during which, if eligible, they will have baseline assessments and be randomized into the study and given blinded study drug. Prior to randomization, subjects must have demonstrated during the Run-In Period the ability to appropriately take study drug and complete the Diary (see inclusion criteria) and must continue to have a sufficient degree of bother based on a score of greater than 15 on the OAB-V8 questionnaire. Following randomization, subjects will return every 4 weeks (Visits 4, 5 and 6, Weeks 4, 8 and 12) for a safety evaluation including adverse event assessment, evaluation of study drug compliance, efficacy-related assessments using the following instruments: Patient Perception of Bladder Condition (PPBC); Clinical Global Impression of Improvement (CGI-I); Overactive Bladder Questionnaire (OABq), a disease specific quality of life and bother questionnaire; the Urgency Questionnaire, and collection of bladder diaries, and to obtain additional Study drug supplies for the following 4 weeks. Subjects will complete a Diary the 3 days prior to each visit. There will be a Follow-up Visit (Visit 7, Week 14) 2 weeks after the end of double-blind treatment. All subjects will have a PVR urine volume ultrasound evaluation at screening, baseline and during each visit during the Double-Blind Treatment Period, except Visit 5 (Week 8). The Columbia Suicide Severity Rating Scale (CSSRS) will be completed at all visits except the Run-In Visit (Visit 2, Week -2).

Dosing and the number and timing of assessments will be slightly different between pharmacokinetic (PK) and non-PK subjects during the Double-Blind Treatment Period to accommodate PK sampling (see Time and Events Schedule). All subjects will take 1 tablet of double-blind study drug in the AM and 1 tablet in the PM during the Double-Blind Treatment Period without regards to meal times. PK subjects will dose in the clinic at each visit during the Double-Blind Treatment Period and therefore visits will generally be required to occur in the morning. Non-PK subjects are not required to dose in the office and there is no constraint on the time of day a visit can occur. Non-PK subjects will take their first dose of blinded study drug in the evening of the day of randomization.

Population Pharmacokinetic Analysis:
About 200 PK subjects will provide samples for a population PK analysis. Sparse population blood samples to document plasma exposure of dexmecamylamine will be collected at Week 0, (Visit 3, Baseline), Week 4 (Visit 4) and Week 12 (Visit 6, End of Double-Blind Treatment Period). Plasma samples at these visits will be collected at pre-dose, at least 2 hours after dosing, and at least 5 hours after dosing. A urine sample for dexmecamylamine concentration determination will also be collected at these visits at 3 hours post-dose. Sites enrolling PK subjects will be required to randomize at least 2 PK subjects prior to enrolling non-PK subjects or unless otherwise agreed by the Sponsor. Once this criterion is met or enrollment of about 200 PK subjects is complete, whichever happens first, a site may also enroll non-PK subjects.

Inclusion Criteria:
At the Screening Visit (Visit 1, Week -3, or -5 if washout of OAB medications is required), subjects must meet all of the following criteria:

1. Subjects must have a verified and documented medical history of overactive bladder for $\geq$ 6 months (Site must confirm at least a 6 month history through, for example, chart note or letter from subject's physician, direct knowledge of subject's OAB history, review of pharmacy prescription record or from dates on subject's OAB medication bottle or others as determined).
2. Males or females aged $\geq$ 18 years.
3. Body Mass Index (BMI) $\leq$ 38.
4. Women of childbearing potential must be currently using or willing to use an acceptable form of contraception as specified in the protocol.
5. Able to understand the informed consent, and provide written informed consent.
6. Capable of walking unassisted to use the bathroom and able to measure voided urine volume and complete the Diary without assistance.
7. If the subject is currently being treated with an OAB medication, the subject is willing to discontinue OAB medications while participating in this study.

| Name of Company: | Name of Finished Product: | Name of Active Substance: |
|---|---|---|
| Targacept, Inc. | Dexmecamylamine hydrochloride | Dexmecamylamine |

8. Subjects should meet all applicable inclusion criteria and not meet any applicable exclusion criteria to progress into the next phase.

Prior to the Run-In Visit (Visit 2, Week -2), the results of all laboratory assessments unavailable at Screening Visit should be evaluated for continued eligibility and tests repeated, as necessary. At the Run-In Visit subjects must meet the following criteria to progress:

1. Confirm that any OAB medication has been discontinued at least 2 weeks prior to visit.
2. Understand how to fill out the Diary.
3. Have a score of greater than 15 on the OAB-V8 screening questionnaire to indicate sufficient OAB symptom bother.
4. Subjects should continue to meet all applicable inclusion criteria and not meet any applicable exclusion criteria to progress into the next phase.

At the Baseline Visit (Visit 3, Week 0) subjects must meet the following criteria prior to randomization:

1. Subject was compliant with completing the 3-day Diary as instructed and at least 80% compliant with taking the study drug during the Run-In Period.
2. Based on the 3-day Diary all subjects must meet either criterion "a" or "b" below. OAB "wet" and "dry" classification is based on the presence or absence, respectively, of UUIs in the Diary during the Run-In Period.
    a. If the subject is classified as OAB "dry" there was an average of $\geq$ 8 micturitions per 24 hours and no UUI episodes in the Diary.
    b. If the subject is classified as OAB "wet" there were $\geq$ 3 UUI episodes over the 3-day Diary and an average of $\geq$ 8 micturitions per 24 hours.
3. Have a bother score of greater than 15 on the OAB-V8 scale.
4. Fulfilled all the inclusion and none of the exclusion criteria.

Exclusion Criteria:
To participate in the study, subjects must not meet any of the following criteria:

1. Receiving any drug or non-drug treatment for OAB except as noted elsewhere after the Screening Visit including physical therapy and electrical or magnetic stimulation. Bladder training programs and behavior modifications for OAB are allowed but must have started at least 3 months prior to screening and must not change during the study.
2. Diagnosis of a neurological disease affecting bladder function (including Parkinson's disease, demyelinating disease such as multiple sclerosis, transverse myelitis, spinal cord injury, brain or spinal tumor, stroke, diabetic neuropathy, spina bifida, caudal agenesis, motor neuron disease).
3. Incontinent subjects where the incontinence is not predominantly urge incontinence based on the 3IQ questionnaire (if questions 1 is yes, question 3b must be checked [i.e., leaked most often due to urge...]).
4. Insensate incontinence, overflow incontinence or incontinence due to urinary fistula.
5. History of incomplete bladder emptying, bladder outflow obstruction or PVR bladder urine volume > 150 mL as determined by a post-void bladder ultrasound on the Screening Visit or Baseline Visit (Visit 3).
6. Males with benign prostatic hyperplasia or with a prostate-specific antigen (PSA) $\geq$ 4 ng/mL at Visit 1 (unless a negative biopsy within 1 year of the Screening Visit) or a significantly rising PSA based on the investigator's opinion if historical data is available.
7. Other urinary tract pathology such as malignancy, ureteric reflux, bladder stone, uninvestigated hematuria, urethral stricture, or cystitis.
8. Urinary tract infection (UTI) or history of recurrent UTIs (2 uncomplicated UTIs in 6 months or 3 positive cultures within the preceding 12 months).
9. Polyuria (> 3000 mL/24 hr).
10. Nocturia due to renal insufficiency or heart failure.

| Name of Company: | Name of Finished Product: | Name of Active Substance: |
|---|---|---|
| Targacept, Inc. | Dexmecamylamine hydrochloride | Dexmecamylamine |

11. Diuretics or hormone replacement therapy initiated or modified within 3 months of the Screening Visit.
12. Prior treatment with intravesical or intraprostatic botulinum toxin in the last 2 years prior to the Screening Visit or planned treatment during the study.
13. An estimated creatinine clearance (Cockcroft and Gault equation) of less than 30 mL/min/1.73 m$^2$
14. An alanine aminotransferase (ALT), aspartate aminotransferase (AST) or alkaline phosphatase ≥ 2x upper limit of normal (ULN) or bilirubin ≥ 1.5x ULN.
15. Women who are pregnant, lactating/nursing or plan to become pregnant, or are postpartum (< 1 year).
16. Women with a visible (outside the vagina) vaginal prolapse on examination at rest or on coughing.
17. Women with demonstrable stress incontinence on examination.
18. Past or present history of clinically significant obstructive gastrointestinal disease.
19. Myasthenia gravis.
20. Angle closure glaucoma.
21. Pelvic or pelvic floor surgery within 6 months prior to the Screening Visit.
22. Surgery (minor outpatient allowed) of any kind within 3 months of the Screening Visit or planned during the study.
23. Current implantation of interstim electrodes or vaginal surgical mesh, or removal of these devices within 3 months of the Screening Visit.
24. Presence of an active infection except for minor skin infections.
25. Presence of a clinically significant medical condition that has been unstable, including clinically significant changes in treatment, within 3 months prior to the Screening Visit or a clinically significant uncontrolled medical condition at any time during the screening process (between the Screening Visit and Baseline Visit).
26. Substance abuse (i.e., drug or alcohol) within 6 months prior to the Screening Visit based on Investigator opinion.
27. History or evidence of clinically significant cardiac abnormality based on the Investigator's opinion as measured by the Screening Visit and Baseline Visit electrocardiograms (ECG).
28. Presence of clinically significant abnormalities in laboratory findings, physical exam findings or vital signs.
29. History of suicide attempts or self-injury in the past 12 months of the Screening Visit or no more than minimal suicidal ideation (thoughts of suicide but nonspecific: no method, intent or plan).
30. Participated in an investigational drug trial within 3 months of the Screening Visit.
31. Subject plans on donating blood during the trial.
32. Previous participation in a clinical study of dexmecamylamine (TC-5214).

Test Product(s), Dose, and Mode of Administration, Batch Number(s):
During the placebo Run-In Period and Double-blind Treatment Period, subjects will be instructed to take study drug twice daily (once in the AM and once in the PM, separated by approximately 12 hours) throughout the study. During the Run-In Period all subjects will take placebo and the study drug will only be blinded to the subject (single blind). During the Double-Blind Treatment Period subjects will be randomized to treatment. During this period subjects will receive one of 4 treatments: 3 active arms (0.5 mg *bid*, 1 mg *bid* and 2 mg *bid*) with 150 subjects per arm, and 1 placebo arm (*bid*) with 300 subjects. Study drug will be taken on an outpatient basis but PK subjects during the Double-Blind Treatment Period will be required to dose at each clinic visit.

The active pharmaceutical ingredient in the investigational product is dexmecamylamine hydrochloride. All dosing will be based on the free base equivalent. The term dexmecamylamine will be used to describe both the active investigational product and active moiety.

Investigational: Dexmecamylamine: 0.5 mg, 1 mg, and 2 mg tablets, batch numbers HZPK, KHVF, and HZPN, respectively.

Control: Matching placebo, batch number HZPG.

| Name of Company: | Name of Finished Product: | Name of Active Substance: |
|---|---|---|
| Targacept, Inc. | Dexmecamylamine hydrochloride | Dexmecamylamine |

Duration of Treatment:
The length of study participation for a subject is about 17-19 weeks depending on whether a subject requires washout from OAB medications (a 3-5 week Screening Period that includes a 2-week washout, as needed, and a 2-week placebo Run-In Period, and a 12-week Double-Blind Treatment Period with 2-week of Follow-up Period).

Concomitant Medication Restrictions:
Use of any medication indicated or used to treat OAB (including off-label use) will be washed out for 2 weeks during the period between the Screening Visit and the Run-In Visit. This may include the following medications for OAB treatment: tolterodine, solifenacin, trospium, darifenacin, fesoterodine, mirabegron, oxybutynin, atropine, dicyclomine/dicycloverine, emepromium, glycopyrronium, flavoxate, isopropamide, oxyphencyclimine, propantheline, propiverine. Medications with known off-label use for treating OAB may be used if not prescribed to treat a subject's OAB (e.g., tricyclic antidepressant for depression is allowed but cannot be used if prescribed for OAB). Prior treatment with intravesical or intraprostatic botulinum toxin in the last 2 years prior to the Screening Visit and during the study is prohibited.

Criteria for Evaluation:
Efficacy Evaluation:
*Co-Primary*
- Change from baseline in micturition frequency per 24 hours to Week 12. [Micturition: Any voiding episode recorded by the patient as "urinated" either with or without incontinence.]
- Change from baseline in UUI episodes per 24 hours to Week 12.

*Secondary*
- Change from baseline in micturition frequency per 24 hours at Week 4 and at Week 8
- Change from baseline in UUI episodes per 24 hours at Week 4 and at Week 8
- Change from baseline in the volume voided per micturition at Weeks 4-12
- Change from baseline in nocturia per 24 hours at Weeks 4-12 [Nocturia: A micturition that wakes the subject from sleep between the time the subject went to bed and the time the subject woke up.]
- Clinical Global Impression of Improvement (CGI-I) at Weeks 4-12
- Change from baseline in Patient Perception of Bladder Condition (PPBC) at Weeks 4-12
- Change from baseline in the Urgency Questionnaire at Weeks 4-12
- Change from baseline in disease specific quality of life (OABq) at Weeks 4-12

Safety Parameters:

- Safety and tolerability will be evaluated throughout the study (see the Time and Events Schedule for details).
- Adverse events will be recorded throughout the study

| Name of Company: | Name of Finished Product: | Name of Active Substance: |
|---|---|---|
| Targacept, Inc. | Dexmecamylamine hydrochloride | Dexmecamylamine |

Statistical Methods:

Efficacy:
The co-primary efficacy endpoints, micturitions and incontinence episodes, will each be analyzed using a MMRM analysis. The primary efficacy endpoints will be assessed based on a change from Baseline (Visit 3) to Week 12 (Visit 6). The MMRM analysis model will employ an unstructured variance-covariance matrix and use the Kenward-Roger adjustment for degrees of freedom. Since these endpoints are co-primaries, both must be statistically significant for the study to provide evidence of efficacy. Hence, no multiplicity adjustment is needed to deal with these co-primary endpoints. A multiplicity adjustment is however needed to deal with the three doses. The fixed sequence method will be utilized in this study. If both co-primary endpoints are significant for the 2 mg dose at the 0.05 level, the co-primary endpoints will be tested at the 0.05 level for the 1 mg dose. If both co-primary endpoints are significant at the 0.05 level for this dose, the co-primary endpoints will be tested at the 0.5 mg dose at the same alpha=0.05 level.

All continuous secondary efficacy endpoints will be based on the MMRM model described in the analysis of primary efficacy endpoints. No multiplicity adjustment will be used for secondary efficacy endpoints. All comparisons of the active doses of dexmecamylamine to placebo will be made at the two-sided 0.05 level, unadjusted for multiplicity.

Additionally responder analysis will include estimations of Urinary Incontinence Dry Rate, Urinary Incontinence Improvement Rate, Urinary Frequency Normalization Rate, Nocturia Cure Rate, and Global Improvement Rate. For each endpoint, the analysis of the proportion of subjects responding will be based on the Cochran-Mantel-Haenszel chi-square and will be stratified by center. This analysis will compare the proportion of placebo subjects responding to the proportion of dexmecamylamine subjects responding for each dose while adjusting for the effect of center.

Pharmacokinetics:
Approximate trough ($C_{min}$) and maximal ($C_{max}$) concentrations will be presented by dose with descriptive statistics. The pharmacokinetic data may be used in a cross-study population pharmacokinetic analysis that may be presented in a separate report at a later date.

Data permitting, urine concentrations of dexmecamylamine will be correlated with the treatment assignment of the subjects as well as with the data from the bladder diaries and other endpoints from each subject.

Safety:
All subjects who are randomly assigned to a treatment and receive at least one dose of the study drug will be included in the safety and tolerability analysis. Baseline for all laboratory evaluations, PVR volume, vital signs, and 12-lead ECG measurements will be defined as the last evaluation done before the first study drug administration. Safety will be evaluated by examining the incidence and type of adverse events, including reports of suicidality, urinary retention, and changes in clinical laboratory test values, physical examination results, 12-lead ECGs, and vital signs measurements from the Screening Period through study completion.

Figure 1: Time and Events Schedule

| Phase | Screening | Washout | Run-In | Double-Blind Treatment | | | | Follow-up |
|---|---|---|---|---|---|---|---|---|
| Visit | 1<br>Screening Visit | | 2 | 3<br>Baseline Visit | 4 | 5 | 6<br>End Treatment/ Withdrawal Visit | 7<br>Follow-up Visit |
| Study Week (Day) | Week -5 or -3[A]<br>(Days -35 or -21) | Week -4 (Day -28) (only subjects on OAB med) | Week -2 (Day -14) | Week 0 (Day 0) | Week 4 (Day 28) | Week 8 (Day 56) | Week 12 (Day 84) | Week 14 (Day 96) |
| Screening | | | | | | | | |
| Informed Consent | X | | | | | | | |
| Demography | X | | | | | | | |
| Medical history and Dx of OAB | X | | | | | | | |
| Inclusion / exclusion | X | | X | X | | | | |
| Safety Procedures | | | | | | | | |
| Physical Examination | X | | | X[B] | X[B] | X[B] | X[B] | X[B,C] |
| Adverse Events | | | | Continuous | | | | |
| Concomitant Medications | | | | Continuous | | | | |
| CSSRS | X | | | X | X | X | X | X |
| Drug / alcohol screen | X | | | | | | X | |
| Safety Lab specimen collection | X | | | X | X | X | X | X[C] |
| Urine pregnancy test | X | | | X | | | X | |
| Study Treatment/General | | | | | | | | |
| Reminder to start washout (only subjects on OAB med) | | X | | | | | | |
| Study Drug Dosing | | | X | X | X | X | X | |
| Dispense Study Drug | | | | | | | | |
|    Run-in | | | X | | | | | |
|    Blinded drug | | | | X | X | X | | |
| Collect unused study drug | | | | X | X | X | X | |
| Randomization | | | | X | | | | |
| Efficacy Procedures | | | | | | | | |
| BIQ | X | | | | | | | |
| OAB-V8 | | | X | X | | | | |
| PPBC | | | | X | X | X | X | |
| CGI-I | | | | | X | X | X | |
| Urgency Questionnaire | | | | X | X | X | X | |
| OABq | | | | X | X | X | X | |
| OAB Diary | | | | | | | | |
| Dispense OAB Diary materials | | | X | X | X | X | | |
| Diary completion subject reminders prior to each visit | | | | X | X | X | X | |
| Collect/review previous OAB Diary with subject | | | | X | X | X | X | |
| Non-PK subjects | | | | | | | | |
| Bladder Scan for post void residual | X | | | X | X | | X | |
| Vital Signs (BP supine, pulse, temp, height[F], weight[F]) | X | | | X | X | X | X | X[C] |
| Orthostatic BP | | | | X | | | X | |
| ECG | X | | | X | X | | X | X[C] |
| Dexmecamylamine random urine sample | | | | | X | | X | |
| Population PK subjects | | | ↓ ← | Dose in the clinic | | → ↓ | | |
| In-Clinic Dosing | | | | X | X | X | X | |
| Bladder Scan for post void residual (predose) | X | | | X | X | | X | |
| Vital Signs (BP supine, pulse, temp, height[F], weight[F]) | X | | | 2X[D] | X | X | 2X[D] | X[C] |
| Orthostatic BP | | | | 2X[D] | | | 2X[D] | |
| ECG | X | | | 2X[D] | X | | 2X[D] | X[C] |
| Dexmecamylamine 3-hour post-dose urine samples | | | | X | X | | X | |
| Dexmecamylamine plasma samples | | | | 3X[E] | 3X[E] | | 3X[E] | |

A - Week -5 for subjects on OAB medication, Week -3 for subjects not on an OAB medication B - abbreviated physical C - only required if clinically significant abnormality at previous visit D - predose and just prior to collection of ≥ 2 hr post-dose PK plasma sample E - 3 samples: predose, ≥ 2 hrs and ≥ 5 hr post-dose F - height at Visit 1, weight at Visit 1 and 6

2. TABLE OF CONTENTS, LIST OF TABLES, AND LIST OF FIGURES

TABLE OF CONTENTS

| | | |
|---|---|---|
| 1. | SYNOPSIS | 5 |
| 2. | TABLE OF CONTENTS, LIST OF TABLES, AND LIST OF FIGURES | 13 |
| 3. | LIST OF ABBREVIATIONS AND DEFINITIONS OF TERMS | 20 |
| 4. | INTRODUCTION | 22 |
| 4.1. | Background | 22 |
| 4.2. | Rationale | 23 |
| 5. | TRIAL OBJECTIVES AND PURPOSE | 24 |
| 5.1. | Primary Objective | 24 |
| 5.2. | Secondary Objective | 24 |
| 6. | INVESTIGATIONAL PLAN | 24 |
| 6.1. | Overall Study Design | 24 |
| 6.2. | Number of Subjects | 29 |
| 6.3. | Efficacy Endpoints | 29 |
| 6.3.1. | Co-Primary Efficacy Endpoints | 29 |
| 6.3.2. | Secondary Endpoints | 29 |
| 6.4. | Treatment Assignment | 30 |
| 6.5. | Dose Adjustment Criteria | 30 |
| 6.6. | Criteria for Study Termination | 30 |
| 7. | SELECTION AND WITHDRAWAL OF SUBJECTS | 31 |
| 7.1. | Subject Inclusion Criteria | 31 |
| 7.2. | Subject Exclusion Criteria | 32 |
| 7.3. | Subject Restrictions and Requirements | 34 |
| 7.3.1. | Medication and Therapy Restriction | 34 |
| 7.3.2. | Food, Meals, Beverages and Fluid Intake | 34 |
| 7.3.3. | Blood Donations | 34 |
| 7.3.4. | Contraception | 34 |
| 7.4. | Subject Completion and Withdrawal | 35 |
| 7.4.1. | Subject Completion | 35 |

| | | |
|---|---|---|
| 7.4.2. | Patient Withdrawal (Premature Discontinuation from the Study) | 35 |
| 7.4.3. | Reporting Discontinuations | 36 |
| 7.4.4. | Replacement of Patients | 36 |
| 8. | TREATMENT OF SUBJECTS | 36 |
| 8.1. | Description of Study Drug | 36 |
| 8.2. | Concomitant Medications and Therapies | 37 |
| 8.2.1. | Non-pharmacological Therapy | 37 |
| 8.2.2. | Pharmacological Therapy | 37 |
| 8.3. | Treatment Compliance | 37 |
| 8.4. | Randomization and Blinding | 37 |
| 9. | STUDY DRUG MATERIALS AND MANAGEMENT | 38 |
| 9.1. | Study Drug | 38 |
| 9.2. | Study Drug Packaging and Labeling | 38 |
| 9.3. | Study Drug Storage | 38 |
| 9.4. | Study Drug Preparation | 39 |
| 9.5. | Administration | 39 |
| 9.6. | Study Drug Accountability | 39 |
| 9.7. | Study Drug Handling and Disposal | 39 |
| 10. | ASSESSMENT OF PHARMACOKINETICS AND BIOMARKERS | 39 |
| 10.1. | Sample Collection and Handling for Pharmacokinetic Samples | 39 |
| 10.1.1. | Population PK Subjects | 39 |
| 10.1.1.1. | Plasma Sample | 39 |
| 10.1.1.2. | Urine Sample | 40 |
| 10.1.2. | Non-Population PK Subjects – Random Dexmecamylamine Urine Sample | 40 |
| 10.2. | Analytical Procedures for Pharmacokinetic Samples | 40 |
| 10.3. | Pharmacokinetic Parameters | 40 |
| 11. | SCREENING ASSESSMENTS | 41 |
| 11.1. | 3 Incontinence Questions (3IQ) Questionnaire | 41 |
| 11.2. | OAB-V8 | 41 |
| 12. | ASSESSMENT OF EFFICACY | 41 |
| 12.1. | Diary | 41 |
| 12.1.1. | Micturition Frequency | 41 |

| | | |
|---|---|---|
| 12.1.2. | Urge Urinary Incontinence | 42 |
| 12.1.3. | Volume Voided per Micturition | 42 |
| 12.1.4. | Nocturia | 42 |
| 12.2. | Clinical Global Impression of Improvement | 42 |
| 12.3. | Patient Perception of Bladder Condition | 42 |
| 12.4. | Urgency Questionnaire | 42 |
| 12.5. | Quality of Life Assessments | 42 |
| 12.5.1. | Overactive Bladder Questionnaire - OABq | 42 |
| 13. | ASSESSMENT OF SAFETY | 43 |
| 13.1. | Safety Parameters | 43 |
| 13.1.1. | Physical Examinations | 43 |
| 13.1.2. | Vital Signs | 43 |
| 13.1.3. | ECG | 43 |
| 13.1.4. | Clinical Laboratory Tests | 43 |
| 13.1.5. | Residual Bladder Volume | 44 |
| 13.1.6. | Columbia Suicide Severity Rating Scale (CSSRS) | 44 |
| 13.2. | Adverse and Serious Adverse Events | 44 |
| 13.2.1. | Definitions | 44 |
| 13.2.1.1. | Adverse Event (AE) | 44 |
| 13.2.1.2. | Serious Adverse Event (SAE) | 44 |
| 13.2.1.3. | Suspected Adverse Reaction | 45 |
| 13.2.1.4. | Unexpected Adverse Event | 45 |
| 13.2.2 | Adverse Event Reporting | 45 |
| 13.2.3. | Laboratory Abnormalities as Adverse Events | 45 |
| 13.3. | Relationship to Study Drug | 46 |
| 13.3.1. | Assessment of Causality | 46 |
| 13.4. | Recording Adverse Events | 46 |
| 13.4.1. | Eliciting Adverse Event Reports | 47 |
| 13.4.2. | Assessment of Intensity | 47 |
| 13.4.3. | Adverse Events of Special Interest | 47 |
| 13.5. | Reporting Adverse Events | 47 |
| 13.5.1. | SAE Reporting Procedures | 47 |

| | | |
|---|---|---|
| 13.5.1.1. | Regulatory Reporting Requirements for SAEs | 48 |
| 13.5.2. | Reporting Safety Information to the IRB | 48 |
| 13.5.3. | Protocol Deviations Due to an Emergency or Adverse Event | 49 |
| 13.6. | Follow-up of Adverse Events | 49 |
| 14. | STATISTICS | 50 |
| 14.1. | Description of Statistical Methods | 50 |
| 14.1.1. | Quantitative and Qualitative Parameters | 50 |
| 14.1.2. | Baseline Data Summary | 50 |
| 14.1.3. | Primary Efficacy Endpoint Analysis | 50 |
| 14.1.4. | Secondary Efficacy Endpoint Analyses | 50 |
| 14.1.5. | Responder Analyses | 51 |
| 14.1.6. | Key Safety Analyses | 51 |
| 14.1.6.1. | Post-void Residual Urine Volume Analyses | 51 |
| 14.1.6.2. | Retention of Urine Analysis | 51 |
| 14.1.7. | Pharmacokinetic Analysis | 52 |
| 14.2. | Sample Size | 52 |
| 14.2.1. | Level of Significance | 52 |
| 14.3. | Procedure for Accounting for Missing, Unused, and Spurious Data | 53 |
| 14.4. | Analysis of Patients Withdrawing Prematurely from the Study | 53 |
| 14.5. | Selection of Patients To Be Included in Analyses | 53 |
| 15. | DIRECT ACCESS TO SOURCE DATA/DOCUMENTS | 53 |
| 15.1. | Study Monitoring | 53 |
| 15.2. | Audits and Inspections | 53 |
| 15.3. | Institutional Review Board (IRB) | 54 |
| 16. | QUALITY CONTROL AND QUALITY ASSURANCE | 54 |
| 16.1. | Regulatory Authority Approval | 54 |
| 16.2. | Protocol Modifications | 54 |
| 17. | ETHICS | 55 |
| 17.1. | Ethics Review | 55 |
| 17.2. | Ethical Conduct of the Study | 55 |
| 17.3. | Written Informed Consent | 55 |
| 18. | DATA HANDLING AND RECORDKEEPING | 56 |

| | | |
|---|---|---|
| 18.1. | Case Report Form Completion and Source Documentation | 56 |
| 18.2. | Data Management | 56 |
| 18.3. | Study Site Close-Out | 57 |
| 18.4. | Retention of Study Documents and Records | 57 |
| 18.5. | Inspection of Records | 57 |
| 19. | INVENTION AND PUBLICATION POLICY | 58 |
| 19.1. | Ownership | 58 |
| 19.2. | Confidentiality | 58 |
| 19.3. | Publication | 58 |
| 20. | LIST OF REFERENCES | 60 |
| 21. | APPENDICES | 62 |
| Appendix 1. | Pharmacokinetic Sample Collection, Handling and Shipping | 63 |
| Appendix 2. | Clinical Laboratory Tests | 65 |

LIST OF TABLES

| | | |
|---|---|---|
| Table 1: | Abbreviations and Specialist Terms | 20 |
| Table 2: | Study Drug | 36 |
| Table 3: | Timeframes for Submitting SAE Reports to Targacept or CRO | 48 |

LIST OF FIGURES

Figure 1: Time and Events Schedule .................................................................. 12
Figure 2: Study Design Schematic ...................................................................... 26

3. LIST OF ABBREVIATIONS AND DEFINITIONS OF TERMS

The following abbreviations and specialist terms are used in this study protocol.

Table 1: Abbreviations and Specialist Terms

| Abbreviation or Specialist Term | Explanation |
|---|---|
| 3IQ | 3 Incontinence Questions Questionnaire |
| AE | Adverse Event |
| ALT | Alanine Aminotransferase |
| AST | Aspartate Aminotransferase |
| *bid* | Twice Daily |
| BMI | Body Mass Index |
| CIB | Clinical Investigator's Brochure |
| $C_{max}$ | Maximum Plasma Concentration |
| $C_{min}$ | Trough or Minimum Plasma Concentration |
| CGI-I | Clinical Global Impression of Improvement |
| CRF | Case Report Form |
| CRO | Clinical Research Organization |
| CSSRS | Columbia Suicide Severity Rating Scale |
| ECG | Electrocardiogram |
| EPA | Environmental Protection Agency |
| FDA | Food and Drug Administration |
| GCP | Good Clinical Practice |
| IB | Investigator's Brochure |
| ICF | Informed Consent Form |
| ICH | International Conference on Harmonization |
| IEC | Institutional Ethics Committee |
| IND | Investigational New Drug Application |
| IRB | Institutional Review Board |
| LC-MS/MS | Liquid Chromatography-Mass Spectrometry/Mass Spectrometry |
| LLOQ | Lower Limit of Quantitation |
| MDD | Major Depressive Disorder |
| mITT | Modified Intention To Treat |

| Abbreviation or Specialist Term | Explanation |
|---|---|
| MMRM | Mixed Model Repeated Measures Analysis |
| NDA | New Drug Application |
| OAB | Overactive Bladder |
| OABq | Overactive Bladder Questionnaire |
| OAB-V8 | Overactive Bladder Questionnaire-V8 |
| OSHA | Occupational Safety and Health Administration |
| Ph. Eur. | European Pharmacopoeia |
| PK | Pharmacokinetic |
| PP | Per-Protocol |
| PPBC | Patient Perception of Bladder Condition |
| PSA | Prostate-Specific Antigen |
| PVR | Post-void Residual Volume of Urine |
| QTcB | QT Interval Corrected for Heart Rate using Bazett's Formula |
| QTcF | QT Interval Corrected for Heart Rate using Fridericia's Formula |
| SAE | Serious Adverse Event |
| SOPs | Standard Operating Procedures |
| SAP | Statistical Analysis Plan |
| TRGT | Targacept |
| ULN | Upper Limit of Normal |
| USP | United States Pharmacopoeia |
| UTI | Urinary Tract Infection |
| UUI | Urinary urge (urgency) incontinence |
| VAS | Visual Analogue Scale |

4. INTRODUCTION

4.1. Background

Overactive bladder (OAB) is a syndrome characterized by symptoms of "urgency with or without urge incontinence, usually with frequency and nocturia," where urgency is defined as "the complaint of a sudden compelling desire to pass urine which is difficult to defer".[1] The prevalence of OAB increases with age and is difficult to determine owing to the attached stigma, which may prevent patients from seeking medical care. OAB is estimated to affect 17% of the adult population in the United States and is ranked among the 10 most common medical conditions.[2,3,4]

Current medications are effective in decreasing all symptoms of OAB including urinary urgency, frequency and urge incontinence, but only to a limited extent. Not all patients achieve acceptable therapeutic responses, resulting in a significant unmet medical need. In addition, these treatments are associated with therapy limiting side effects such as dry mouth, dry eyes, blurred vision, constipation and cognitive dysfunction. The majority of available medications are metabolized by the cytochrome P450 pathway potentially leading to drug-drug interactions, especially in the elderly where OAB is most common and in whom poly-pharmacy is common. The limited efficacy and significant incidence of adverse effects diminish the usefulness of these drugs; often patients stop taking these medications altogether. About 65-85% of patients do not continue therapy beyond 12 months.[5,6] Of those remaining on treatment, some patients take less than the optimal dosage to avoid the side effects. Alternative OAB medications are needed with different safety, metabolic, tolerability and efficacy profiles. Because patients with OAB have different medical histories, varying comorbid conditions, and may take different concomitant medications, this patient population will benefit from the availability of OAB medications with different product attributes.

Dexmecamylamine (also referred to as S-mecamylamine and TC-5214) is a selective nicotinic acetylcholine receptor (nAChR) channel modulator. While the precise molecular targets associated with effects on the bladder are still under investigation, dexmecamylamine functionally interacts with human $\alpha 4\beta 2$, $\alpha 3\beta 2$, and $\alpha 3\beta 4$ nicotinic receptors and the known interactions of dexmecamylamine with $\alpha 3$-containing nicotinic receptors suggests it is likely to prove beneficial in the treatment of OAB. Nonclinical studies with dexmecamylamine have been conducted to evaluate the potential for treatment in OAB. No clinical studies with dexmecamylamine have been conducted specifically for OAB.

Because dexmecamylamine is excreted almost entirely unchanged in the urine, dexmecamylamine reaches higher concentrations in the urine compared to the plasma. The exposure differential results in the ability of dexmecamylamine to target local nicotinic receptors in the urothelium that affect bladder contraction frequency while limiting systemic side effects. Consequently the potential for dexmecamylamine to treat OAB through its action on nAChRs in the bladder urothelium warrants further investigation.

Dexmecamylamine is the S-(+)-enantiomer of mecamylamine, an agent previously marketed as Inversine® for the treatment of hypertension. More recently, dexmecamylamine was evaluated as adjunctive therapy in the treatment of major depressive disorder (MDD) in a large international Phase 3 depression program. Although dexmecamylamine failed to demonstrate efficacy in the treatment of depression, the compound proved to be well tolerated at doses up to and including the top dose evaluated, 4 mg twice daily (*bid*). More than 2400 subjects have received dexmecamylamine in double-blind or open-label studies.

No safety studies have been performed in OAB. Phase 2 and Phase 3 clinical studies using dexmecamylamine in Major Depressive Disorder (MDD) have been conducted and completed. Dexmecamylamine was generally safe and well-tolerated in these studies. Briefly, in the fixed dose Phase 3 studies in MDD, at doses of 2 mg *bid* or less (the maximum doses to be studied in the OAB study), the most frequent treatment emergent adverse event that were reported more than 2% more commonly in the dexmecamylamine compared to placebo group were: constipation (15.2% dexmecamylamine vs. 3.8% placebo); and dry mouth (7.0% dexmecamylamine vs. 1.3% placebo). There were no noteworthy differences in any measurements of vital signs, blood or urine laboratory measurements, ECG conduction intervals, or suicidality.

A complete description of the nonclinical and clinical safety and tolerability findings for dexmecamylamine is described in the Investigator's Brochure.

4.2. Rationale

Dexmecamylamine is a use dependent potent inhibitor of the α3 nicotinic receptor subtype (e.g., α3β2, and α3β4). Such receptors are expressed in the urothelium and regulate bladder smooth muscle contraction and urinary urge in the rat.[7] In an anesthetized rat model, intravesical instillation of dexmecamylamine at concentrations of 1 and 10 μM, produced meaningful decrements in bladder contractility and micturition frequency. Such concentrations also increased bladder capacity while not affecting the amplitude of bladder contractions. Dexmecamylamine is almost completely absorbed from the gastrointestinal tract, and > 90% is excreted unchanged in urine. In man, peak plasma concentration occurs in about 2 to 3 hours and the elimination half-life is around 10 hours. Dexmecamylamine is almost completely excreted unchanged in the urine, therefore doses that have already been shown to be safe and well tolerated in the Major Depressive Disorder Program (up to 4 mg twice daily [*bid*]) produce high concentrations in the urine that are thought to block α3 nicotinic receptors in the urothelium on the luminal surface of the bladder. For example, at steady state following 2 mg *bid* (a total of 4 mg per day), and a normal urinary output of 2 liters per day, the average urinary concentration would be 2 mg per liter, which is approximately 12 μM. Since urinary concentrations as low as 1 μM produced robust decreases in bladder contraction and micturition frequency in a preclinical model, it is projected that doses of 0.5 to 2 mg *bid* of dexmecamylamine will diminish bladder contractions and the sensations of urinary urgency, proving efficacious in the treatment of OAB.

No clinical studies with dexmecamylamine have been conducted previously for OAB. The purpose of this present investigation is to determine if dexmecamylamine has a beneficial effect in patients with OAB.

5. TRIAL OBJECTIVES AND PURPOSE

5.1. Primary Objective

- To assess the efficacy of dexmecamylamine in the treatment of OAB

5.2. Secondary Objective

- To assess the safety, tolerability and pharmacokinetic profile of dexmecamylamine in subjects with OAB

6. INVESTIGATIONAL PLAN

6.1. Overall Study Design

This is a Phase 2b, multicenter, randomized, double-blind, fixed-dose, parallel-group, placebo-controlled study to assess the efficacy, safety, and tolerability of dexmecamylamine in subjects with OAB. The length of study participation for a subject is about 17-19 weeks depending on whether a subject requires washout from OAB medications (a 3-5 week Screening Period that includes a 2-week washout, as needed, and a single-blind, 2-week placebo Run-In Period, and a 12-week Double-Blind Treatment Period with 2-week Follow-up Period). The Study Design Schematic is shown below in Figure 2.

Sufficient subjects will be screened and complete a 2-week Run-In Period such that approximately 750 total subjects will be randomized into the Double-Blind Treatment Period of the study. There will be 3 active arms (0.5 mg *bid*, 1 mg *bid* and 2 mg *bid*) with 150 subjects per arm and 1 placebo arm (placebo *bid*) with 300 subjects. The strategy of randomizing twice as many subjects to the placebo arm as to each active treatment arm was chosen to primarily avoid expectation bias. A subject's expectation that they will have an increased chance of receiving active treatment has been shown to increase the placebo response and hence decrease the ability to identify an efficacy signal in a number of studies in other therapeutic areas.[8] In addition this approach results in a modest (6%) decrease in the total sample size required. By randomizing 40% of the subjects to placebo and 60% to dexmecamylamine treatment the ability of the study to detect an efficacy signal should be enhanced.

The target proportion of OAB "wet" subjects at baseline, based on the presence of urinary urge incontinence (UUI) episodes in the Diary during the Run-In Period, will be at least 75%; however, randomization will not be stratified according to OAB type. The proportion of randomized OAB "wet" subjects to OAB "dry" subjects will be monitored and the screening of OAB "dry" subjects may be limited during the study in an attempt to randomize at least 75% OAB "wet" subjects. It is anticipated that the study population will be primarily women. The percentage of males enrolled in the study will be monitored and may be limited to 20% or less.

The study will consist of 7 visits (Figure 2) with a ± 3 day visit window except for subjects requiring washout of OAB medications the Run-In Visit (Visit 2, Week -2) should occur after at least a 2 week washout. Subjects should be kept on schedule and within this window whenever possible. The study management team should be notified within a reasonable timeframe relative to the occurrence of "out of window" events. During the interval between the Screening Visit (Visit 1, Week -3, or Week -5 if subject requires washout of OAB medications) and the next step (start of washout or Run-In Period) it is acceptable and appropriate to delay the next step for activities such as repeating a screening lab or for the follow up of screening-related medical history questions or documentation in order to have adequate information for a decision to move the subject on to the next step.

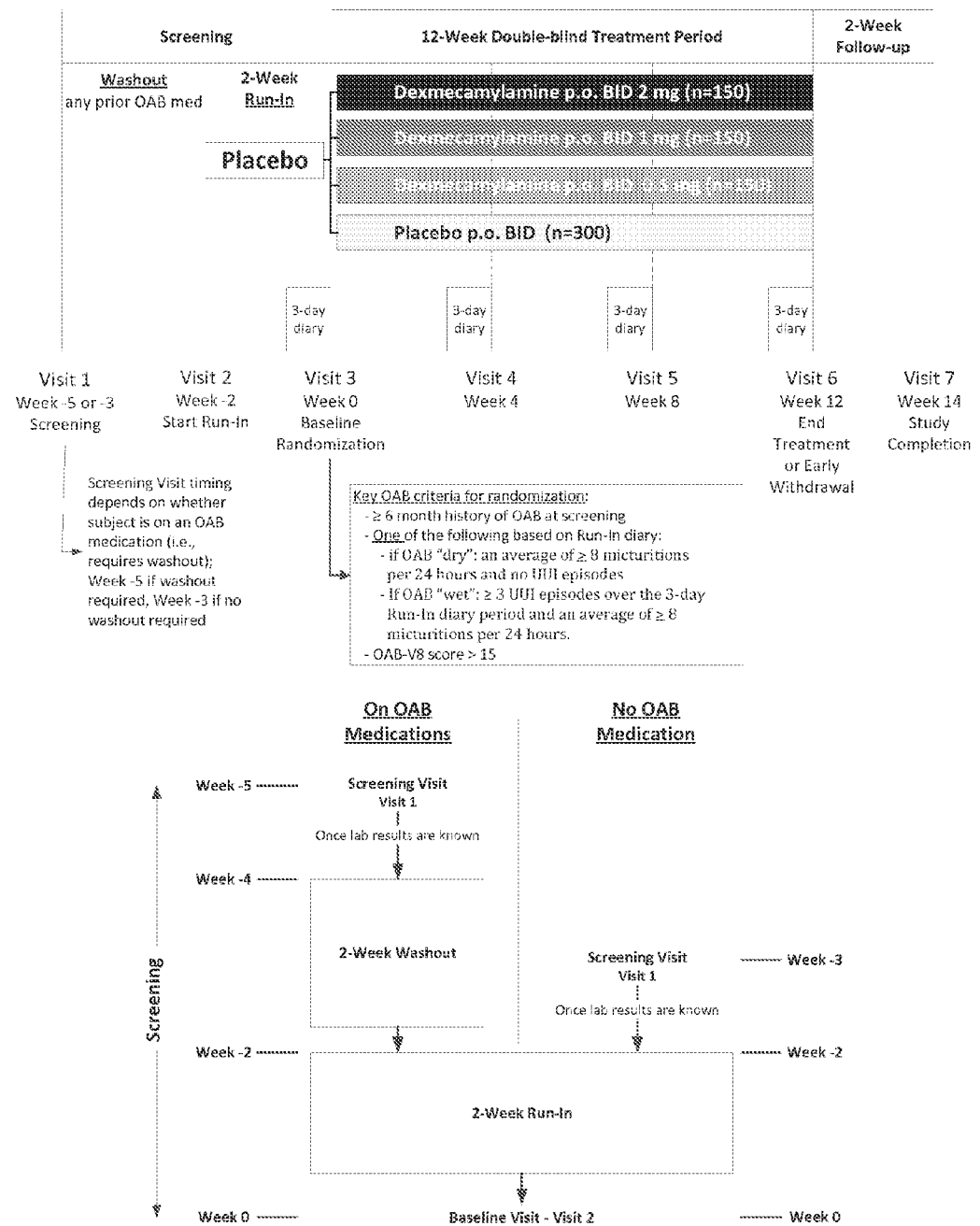
Figure 2: Study Design Schematic

The length of the Screening Period will be 3-5 weeks depending on whether the subject is on any OAB medications (see Section 8.2.2) at Visit 1 (Figure 2). Subjects on an OAB medication will have the Screening Visit (Visit 1) on about Week -5. This will allow sufficient time to obtain final central laboratory results prior to initiation of the washout on Week -4. Subjects not on OAB medications at should have their Screening Visit about 1 week prior (Week -3) to the initiation of the 2-week Run-In Period which will begin for all subjects on Week -2 (Visit 2).

At the Screening Visit (Visit 1, Week -3, or Week -5 if subject requires washout of OAB medications) following informed consent, initial eligibility will be verified per the inclusion/exclusion criteria before blood is drawn for safety labs. Key initial eligibility criteria will include a <u>verified and documented</u> history of OAB of at least 6 months duration, urge predominant incontinence for subjects with urinary incontinence as verified with the 3 Incontinence Questions (3IQ) questionnaire, and a post-void residual urine (PVR) of < 150 mL. Subjects with exclusionary laboratory results have the opportunity of a repeat test and subjects may be enrolled, at the discretion of the investigator, if the repeat test is within the eligible range and is consistent with the subject's clinical picture. All subjects, who meet the preliminary eligibility criteria at the Screening Visit and do not have exclusionary abnormalities in the laboratory tests, will either washout of their current OAB medication for at least 2 weeks prior to the Run-In Visit, as appropriate, or have the Run-In Visit about 1 week later if washout is not required.

At the Run-In Visit (Visit 2, Week -2), the appropriate washout of OAB medications will be confirmed and all subjects must have a sufficient degree of bother based on a score of greater than 15 on the Overactive Bladder Questionnaire-V8 (OAB-V8). Subjects that continue to be eligible will be trained on the use of the Diary, study drug for the Run-In Period will be dispensed, and the subject instructed on how and when to take the study drug. The Run-In Period will be single-blinded to the subject and all subjects will take placebo study drug. Subjects will take the Run-In Period study drug twice a day in the AM and PM for 2 weeks (14 days ± 3 days). First dose will be the evening of the visit. Subjects will be instructed to maintain their normal level of fluid consumption throughout the trial and therefore they should try not to alter their fluid intake over the course of the trial. Subjects will complete a diary on the last 3 days of the Run-In Period. Subjects will record in their Diary: 1) the time the subject woke up and went to sleep; 2) the time of each micturition; and 3) the time of each incontinence episode and whether the leak was associated with urge ("due to need to urinate", a UUI episode) or without urge ("due to other reasons"). In addition on Day 1 of diary data collection, subjects will measure and record the volume of each voluntary micturition over a 24 hr period. Subjects who forget to complete void volume on Diary Day 1 or cannot measure void volume on Diary Day 1 can complete this task on Diary Day 2 or 3. Subjects will be reminded about the completion of the Diary (see Diary details in Section 12.1).

Following the 2-week Run-In Period, subjects will return to the clinic for the Baseline Visit (Visit 3, Week 0) during which, if eligible, they will have baseline assessments and be randomized into the study and given blinded study drug. Prior to randomization, subjects must have demonstrated during the Run-In Period the ability to appropriately take study drug (80% compliance), successfully complete the Diary as instructed, and must continue to have a sufficient degree of bother based on a score of greater than 15 on the OAB-V8 questionnaire.

At baseline all subjects must meet one of the following criteria based on the Diary from the Run-In Period:

1. If the subject is classified as OAB "dry" there was an average of ≥ 8 micturitions per 24 hours and no UUI episodes in the Diary during the Run-In Period.
2. If the subject is classified as OAB "wet" there were ≥ 3 UUI episodes over the 3-day Diary and an average of ≥ 8 micturitions per 24 hours.

Note: OAB "wet" and "dry" classification is based on the presence or absence, respectively, of UUIs in the Diary during the Run-In Period.

Following randomization, subjects will return to the clinic every 4 weeks (Visits 4, 5 and 6; Weeks 4, 8 and 12) for a safety evaluation including a PVR evaluation, evaluation of study drug compliance, documentation of adverse events (AEs), and efficacy-related assessments using the following instruments: Patient Perception of Bladder Condition (PPBC); Clinical Global Impression of Improvement (CGI-I); Overactive Bladder Questionnaire (OABq), a disease specific quality of life and bother questionnaire; the Urgency Questionnaire, and collection of completed diaries, and to obtain additional Study drug supplies for the following 4 weeks per the Time and Events Schedule (Figure 1). Subjects during the Double-Blind Treatment Period will complete a Diary during the 3 days prior to each visit. Subjects will be reminded when to start the Diary and will be followed to ensure the void volume is collected on Day 1. Subjects who forget to complete void volume on Diary Day 1 or cannot measure void volume on Diary Day 1 can complete this task on Diary Day 2 or 3.

The last planned study visit will be a Follow-up Visit (Visit 7, Week 14) 2 weeks ± 3 days after the end of double-blind treatment. If a subject is prematurely discontinued from the study for any reason after completing the Baseline Visit (Visit 3, Week 0), the Investigator will make every effort to perform all evaluations as per protocol as if the subject had reached the end of the Double-Blind Treatment Period. These 'early withdrawal' evaluations will include assessments already specified for Visit 6 (Week 12) and should be done as soon as possible, but not later than within two weeks of discontinuation.

Sparse population pharmacokinetic (PK) blood samples from about 200 subjects (PK subjects) to document plasma exposure of dexmecamylamine will be collected at the Baseline Visit (Visit 3, Week 0), Visit 4 (Week 4) and Visit 6 (Week 12, End of Double-Blind Treatment Period). Plasma samples at these visits will be collected at pre-dose, at least 2 hours after dosing, and at least 5 hours after dosing. A urine sample for dexmecamylamine urine concentration determination will also be collected from PK subjects at these visits at 3 hours post-dose. Sites enrolling PK subjects will be required to randomize at least 2 PK subjects prior to enrolling non-PK subjects, unless otherwise agreed by the sponsor. Once this criterion is met or enrollment of about 200 PK subjects is complete, whichever happens first, a site may also enroll non-PK subjects.

Dosing and the number and timing of assessments during the Double-Blind Treatment Period will be slightly different between PK and non-PK subjects to accommodate PK sampling (see Time and Events Schedule, Figure 1). All subjects will take 1 tablet of study drug in the AM and 1 tablet in the PM during the Double-Blind Treatment Period without regards to meal times but PK subjects will dose in the clinic at each visit during the Double-Blind Treatment Period and therefore visits will generally be required to occur in the morning. Non-PK subjects are not required to dose in the office and there is no constraint on the time of day a visit can occur. Non-PK subjects will take their first dose of blinded study drug in the evening of the day of randomization.

6.2. Number of Subjects

Enough subjects will be screened and enrolled into the 2-week Run-In Period such that a total of approximately 750 total subjects will be randomized into the Double-Blind Treatment Period of the study. There will be 3 active arms (0.5 mg *bid*, 1 mg *bid* and 2 mg *bid*) with 150 subjects per arm, and 1 placebo arm (placebo *bid*) with 300 subjects. The dexmecamylamine dose is expressed as the free base equivalent.

Subjects at screening will be given a subject number. Subject initials will not be collected or used as an identifier. The subject number will be used to identify the subject and laboratory samples associated with each subject.

6.3. Efficacy Endpoints

6.3.1. Co-Primary Efficacy Endpoints

The primary objective of the study is to assess the efficacy of dexmecamylamine vs. placebo in subjects with overactive bladder as defined by the following co-primary endpoints:

- Change from baseline in micturition frequency per 24 hours to Week 12 (diary) [Micturition: Any voiding episode recorded by the patient as "urinated" either with or without incontinence.]
- Change from baseline in UUI episodes per 24 hours to Week 12 (diary)

6.3.2. Secondary Endpoints

- Change from baseline in micturition frequency episodes per 24 hours at Week 4 and at Week 8 (diary)
- Change from baseline in UUI episodes per 24 hours at Week 4 and at Week 8 (diary)
- Change from baseline in the volume voided per micturition at Weeks 4-12 (diary assessment)
- Change from baseline in nocturia per 24 hours at Weeks 4-12 (diary) [Nocturia: A micturition that wakes the subject from sleep between the time the subject went to bed and the time the subject woke up.]

- Clinical Global Impression of Improvement (CGI-I) at Weeks 4-12 (in-office assessment)
- Change from baseline in Patient Perception of Bladder Condition (PPBC) at Weeks 4-12 (in-office assessment)
- Change from baseline in the Urgency Questionnaire at Weeks 4-12 (in-office assessment)
- Change from baseline in disease specific quality of life (OABq) at Weeks 4-12 (in-office assessment)

6.4. Treatment Assignment

At randomization subjects will be assigned to placebo *bid*, dexmecamylamine 2 mg *bid*, 1 mg *bid* or 0.5 mg *bid* in a ratio of 2:1:1:1.

6.5. Dose Adjustment Criteria

Dose adjustments (escalation or reduction) are not allowed in the present study. If the Investigator decides that continued use of study drug is not in the best interest of the subject, the subject may be withdrawn from the study and termination assessments performed.

6.6. Criteria for Study Termination

Sponsor reserves the right to temporarily suspend or prematurely discontinue this study either at a single site or at all sites at any time for reasons including, but not limited to, safety or ethical issues or severe non-compliance. If Sponsor determines such action is needed, Sponsor will discuss this with the Investigator or Investigators (including the reasons for taking such action) at that time. When feasible, Sponsor will provide advance notification to the Investigator(s) of the impending action prior to it taking effect.

Sponsor will promptly inform all other Investigators and/or institutions conducting the study if the study is suspended or terminated for safety reasons, and will also inform the regulatory authorities of the suspension or termination of the study and the reason(s) for the action. If required by applicable regulations, the Investigator or Targacept/Targacept designee, depending on whether the Institutional Review Board (IRB) is a central or local IRB, must inform the IRB promptly and provide the reason for the suspension or termination.

If the study is prematurely discontinued, all study data must be returned to Sponsor. In addition, arrangements will be made for all unused study drug(s) to be destroyed or returned in accordance with the applicable procedures for the study.

7. SELECTION AND WITHDRAWAL OF SUBJECTS

7.1. Subject Inclusion Criteria

At the Screening Visit (Visit 1, Week -3, or -5 if washout of OAB medications is required), subjects must meet all of the following criteria:

1. Subjects must have a verified and documented medical history of overactive bladder for $\geq 6$ months (Site must confirm at least a 6 month history through, for example, chart note or letter from subject's physician, direct knowledge of subject's OAB history, a review of pharmacy prescription record or from dates on subject's OAB medication bottle or others as determined).
2. Males or females aged $\geq 18$ years.
3. Body Mass Index (BMI) $\leq 38$.
4. Women of child bearing potential must be currently using or willing to use an acceptable form of contraception as specified in the protocol (Section 7.3.4).
5. Able to understand the informed consent, and provide written informed consent.
6. Capable of walking unassisted to use the bathroom and able to measure voided urine volume and complete the diary without assistance.
7. If the subject is currently being treated with an OAB medication, the subject is willing to discontinue OAB medications while participating in this study.
8. Subjects should meet all applicable inclusion criteria and not meet any applicable exclusion criteria to progress into the next phase.

Prior to the Run-In Visit (Visit 2, Week -2), the results of all laboratory assessments unavailable at the Screening Visit should be evaluated for continued eligibility and tests repeated, as necessary. At the Run-In Visit subjects must meet the following criteria to progress:

1. Confirm that all OAB medication have been discontinued at least 2 weeks ($\pm 3$ days) prior to visit.
2. Understand how to fill out the Diary.
3. Have a score of greater than 15 on the OAB-V8 screening questionnaire to indicate sufficient OAB symptom bother.
4. Subjects should meet all applicable inclusion criteria and not meet any applicable exclusion criteria to progress into the next phase.

At the Baseline Visit (Visit 3, Week 0) subjects must meet the following criteria prior to randomization:

1. Subject was compliant with completing the 3-day Diary as instructed and at least 80% compliant with taking the study drug during the Run-In Period.
2. Based on the 3-day Diary all subjects must meet either criterion "a" or "b" below. OAB "wet" and "dry" classification is based on the presence or absence, respectively, of UUIs in the Diary during the Run-In Period.
   a. If the subject is classified as OAB "dry" there was an average of $\geq 8$ micturitions per 24 hours and no UUI episodes in the Diary.
   b. If the subject is classified as OAB "wet" there were $\geq 3$ UUI episodes over the 3-day Diary and an average of $\geq 8$ micturitions per 24 hours.
3. Have a bother score of more than 15 on the OAB-V8 scale.
4. Fulfilled all the inclusion and none of the exclusion criteria.

7.2. Subject Exclusion Criteria

To participate in the study, subjects must not meet any of the following criteria:

1. Receiving any drug or non-drug treatment for OAB except as noted elsewhere after the Screening Visit including physical therapy and electrical or magnetic stimulation. Bladder training programs and behavior modifications for OAB are allowed but must have started at least 3 months prior to screening and must not change during the study.
2. Diagnosis of a neurological disease affecting bladder function (including Parkinson's disease, demyelinating disease such as multiple sclerosis, transverse myelitis, spinal cord injury, brain or spinal tumor, stroke, diabetic neuropathy, spina bifida, caudal agenesis, motor neuron disease).
3. Incontinent subjects where the incontinence is not predominantly urge incontinence based on the 3IQ questionnaire (if questions 1 is yes, question 3b must be checked [i.e., leaked most often due to urge...]).
4. Insensate incontinence, overflow incontinence or incontinence due to urinary fistula.
5. History of incomplete bladder emptying, bladder outflow obstruction or PVR bladder urine volume > 150 mL as determined by a post-void bladder ultrasound at the Screening Visit or Baseline Visit.
6. Males with benign prostatic hyperplasia or with a prostate-specific antigen (PSA) $\geq 4$ ng/mL at Visit 1 (unless a negative biopsy within 1 year of the Screening Visit) or a significantly rising PSA based on the Investigator's opinion if historical data is available.
7. Other urinary tract pathology such as malignancy, ureteric reflux, bladder stone, uninvestigated hematuria, urethral stricture, or cystitis.
8. Urinary tract infection (UTI) or history of recurrent UTIs (2 uncomplicated UTIs in 6 months or 3 positive cultures within the preceding 12 months).

9. Polyuria (> 3000 mL/24 hr).
10. Nocturia due to renal insufficiency or heart failure.
11. Diuretics or hormone replacement therapy initiated or modified within 3 months of the Screening Visit.
12. Prior treatment with intravesical or intraprostatic botulinum toxin in the last 2 years prior to the Screening Visit or planned treatment during the study.
13. An estimated creatinine clearance (Cockcroft and Gault equation) of less than 30 mL/min/1.73 m$^2$.
14. An alanine aminotransferase (ALT), aspartate aminotransferase (AST) or alkaline phosphatase $\geq$ 2x upper limit of normal (ULN) or bilirubin $\geq$ 1.5x ULN.
15. Women who are pregnant, lactating/nursing or plan to become pregnant, or are postpartum (< 1 year).
16. Women with a visible (outside the vagina) vaginal prolapse on examination at rest or on coughing.
17. Women with demonstrable stress incontinence on examination.
18. Past or present history of clinically significant obstructive gastrointestinal disease.
19. Myasthenia gravis.
20. Angle closure glaucoma.
21. Pelvic or pelvic floor surgery within 6 months prior to the Screening Visit.
22. Surgery (minor outpatient allowed) of any kind within 3 months of the Screening Visit or planned during the study.
23. Current implantation of interstim electrodes or vaginal surgical mesh, or removal of these devices within 3 months of the Screening Visit.
24. Presence of an active infection except for minor skin infections.
25. Presence of a clinically significant medical condition that has been unstable, including clinically significant changes in treatment, within 3 months prior to the Screening Visit or a clinically significant uncontrolled medical condition at any time during the Screening Period (between the Screening Visit and Baseline Visit).
26. Substance abuse (i.e., drug or alcohol) within 6 months prior to the Screening Visit based on Investigator opinion.
27. History or evidence of clinically significant cardiac abnormality based on the Investigator's opinion as measured by the Screening Visit and Baseline Visit electrocardiograms (ECG).
28. Presence of clinically significant abnormalities in laboratory findings, physical exam findings or vital signs.

29. History of suicide attempts or self-injury in the past 12 months of the Screening Visit or no more than minimal suicidal ideation (thoughts of suicide but nonspecific: no method, intent or plan).

30. Participated in an investigational drug trial within 3 months of the Screening Visit.

31. Subject plans on donating blood during the trial.

32. Previous participation in a clinical study of dexmecamylamine (TC-5214).

7.3. Subject Restrictions and Requirements

7.3.1. Medication and Therapy Restriction

See Section 8.2.

7.3.2. Food, Meals, Beverages and Fluid Intake

There are no restrictions to when the study drug may be taken in regards to food, meals or beverages. Subjects will be instructed to maintain their normal level of fluid consumption throughout the trial and therefore they should not alter their fluid intake greatly over the course of the trial.

7.3.3. Blood Donations

Subjects will be advised that they should not donate blood until after completion of the study.

7.3.4. Contraception

Women of childbearing potential are defined as premenopausal women who are not surgically sterile. Surgically sterile is defined as women with tubal ligation, hysterectomy and/or bilateral oophorectomy.

Women of childbearing potential must:

1. Have a negative urine pregnancy test.
2. Not be lactating.

Women of childbearing potential with male partners must:

1. Be willing to use acceptable methods of contraception from screening through follow-up unless the woman is in a monogamous relationship with a sterilized male partner (e.g., vasectomy).
2. Acceptable methods of birth control are systemic contraceptives (contraceptive pills, hormonal implants, contraceptive patches and injectable contraceptives), or intra-uterine devices), double-barrier methods, or as approved by the medical monitor.

7.4. Subject Completion and Withdrawal

7.4.1. Subject Completion

A subject will be considered to have completed the study if they complete the entire study through the Follow-up Period (Follow-up Visit, Visit 7, Week 14). Subjects who prematurely discontinue study treatment for any reason before completion of the Double-Blind Treatment Period will be treated as outlined in the following sections.

7.4.2. Patient Withdrawal (Premature Discontinuation from the Study)

A documented effort must be made to determine why a subject fails to return for the necessary visits or is dropped from the study, and the reason for withdrawal must be recorded in the case report form (CRF) and source documents. A subject may withdraw or be removed from the study for any of the following reasons and will be treated as considered appropriate by the Investigator:

- Subject request (for any reason)
- In the opinion of the Investigator, continuation is not in the best interest of the subject.
- A serious or unexpected AE occurs such that continuation in the study is inappropriate.
- Lack of efficacy, if this places the subject at risk.
- Pregnancy
- In the opinion of the Sponsor, continuation is not in the best interest of the subject.

Subjects with a voiding difficulty should be considered for withdrawal based on the Investigator's opinion. Subjects requiring catheterization for urinary retention should be withdrawn. Subjects should also be withdrawn if a subject's PVR meets the following criteria:

- asymptomatic PVR > 350 mL
- symptomatic PVR > 200 mL
- lower PVRs if in the Investigator's discretion this compromises subject safety If a subject is prematurely discontinued from participation in the study for any reason, the Investigator must make every effort to perform all evaluations as per protocol assuming the subject had reached the end of the Double-Blind Treatment Period. These evaluations will be made as soon as possible but within two weeks of discontinuation. Also, the Investigator is to:

- Follow up on all ongoing adverse events (if any);
- Collect all unused study drug.

These data should be recorded, as they comprise an essential evaluation that should be done before discharging any subject from the study.

In the event a subject is prematurely discontinued from the study due to an AE, or unexpected AE or serious adverse event (SAE) (as defined in Section 13.2.1), the procedures stated in Sections 13.2-13.6 must be followed.

7.4.3. Reporting Discontinuations

Reasons for discontinuation from the study must be documented on the source document and in the CRF. Study drug assigned to the withdrawn subject may not be assigned to another subject.

7.4.4. Replacement of Patients

Randomized subjects who drop out of the study after randomization into the Double-Blind Treatment Period of the study ("drop-outs") will not be replaced.

8. TREATMENT OF SUBJECTS

8.1. Description of Study Drug

Dexmecamylamine (also referred to as S-mecamylamine, TC-5214 and TC-5214-23) is the S(+)-enantiomer of racemic mecamylamine, a non-competitive nicotinic channel modulator.

The study drug is described below in Table 2.

Table 2: Study Drug

|  | Investigational Product | Matching Placebo |
| --- | --- | --- |
| Product Name: | Dexmecamylamine | Placebo |
| Dosage Form: | Tablet | Tablet |
| Unit Dose | 0.5 mg, 1 mg, or 2 mg (batches HZPK, KHVF, HZPN, respectively) | 0 mg Batch HZPG |
| Route of Administration | Oral | Oral |
| Physical Description | Film Coated Tablet | Film Coated Tablet |
| Manufacturer | Patheon, Inc. | Patheon, Inc. |

8.2. Concomitant Medications and Therapies

8.2.1. Non-pharmacological Therapy

Subjects practicing behavior modification techniques such as pelvic floor exercises are allowed to participate in the study if their regimen has been stable for 3 months prior to the Screening Visit and there is no change in their regimen nor should they receive any additional instruction or intervention during the course of the study.

8.2.2. Pharmacological Therapy

Concomitant medications are permitted during this study unless otherwise specified below. Drugs should be stable at the Screening Visit with no clinically significant changes in drugs for 3 months prior to the Screening Visit, during the period between the Screening Visit and the Baseline Visit (Visit 3, Week 0), and should remain stable through the study.

An OAB medication is any medication indicated or used to treat OAB (including off-label use). All OAB medications will be washed out during the period between the Screening Visit and Run-In Visit and prohibited during the remainder of the trial. Medications with known off-label use for treating OAB may be taken by the subject if not prescribed to treat a subject's OAB (e.g., a tricyclic antidepressant taken for depression is allowed but cannot be used if prescribed for OAB). OAB medications not to be used may include the following drugs for OAB treatment:

| | | | |
|---|---|---|---|
| tolterodine | oxybutynin | isopropamide | flavoxate |
| solifenacin | mirabegron | oxyphencyclimine | |
| trospium | dicyclomine/dicycloverine | propantheline | |
| darifenacin | emepromium | propiverine | |
| fesoterodine | glycopyrronium | atropine | |

Prior treatment with intravesical or intraprostatic botulinum toxin in the last 2 years prior to the Screening Visit and during the study is prohibited.

8.3. Treatment Compliance

Only patients who consume at least 80% of the prescribed daily dose during the Double-Blind Treatment Period will be considered compliant in the context of this protocol.

8.4. Randomization and Blinding

Subjects will be randomized into the Double-Blind Treatment Period at the Baseline Visit (Visit 3, Week 0) provided they continue to satisfy all screening inclusion and exclusion criteria. An Interactive Response System will be used to assign subjects to one of four treatment cohorts: 1) dexmecamylamine 0.5 mg *bid;* 2) dexmecamylamine 1 mg *bid;* 3) dexmecamylamine 2 mg *bid;* or 4) matching placebo *bid* based on a pre-defined randomization schedule.

Dexmecamylamine and matching placebo will be prepared in identical tablets thereby ensuring subjects and Investigators will be blinded to drug identity. All study staff will remain blinded throughout the study. The blind can only be broken with the permission of the Targacept Medical Monitor, unless needed for emergency management of an SAE. The blind can be broken through an interactive web-based system which will record all episodes of unblinding.

9. STUDY DRUG MATERIALS AND MANAGEMENT

9.1. Study Drug

The active pharmaceutical ingredient in the investigational product that will be used in this study is the hydrochloride salt of dexmecamylamine, which has been designated as dexmecamylamine hydrochloride. All dosing will be based on the free base equivalent (dexmecamylamine) of the hydrochloride salt. The term dexmecamylamine will be used to describe both the active investigational product and active moiety.

Investigational product will be provided as oral tablets containing 0.5 mg, 1 mg or 2 mg (free base equivalent) of dexmecamylamine; as well as an excipient matrix consisting of microcrystalline cellulose (PH101 & PH102), hydroxypropyl cellulose, croscarmellose sodium, colloidal silicone dioxide, and magnesium stearate with a film coating comprised of hypromellose 2910, titanium dioxide, macrogel 400, and yellow iron oxide. Matching placebo will be provided in oral tablets with adjustments to the quantity of microcrystalline cellulose to account for the absence of drug in the formulation. All components comply with the relevant European Pharmacopoeia (Ph. Eur.) and United States Pharmacopoeia (USP) monographs.

9.2. Study Drug Packaging and Labeling

All subjects will be provided blistered placebo cards during the two week Run-In Period. During the Double-Blind Treatment Period, dexmecamylamine and matching placebo will be supplied as 6 blister cards of 14 tablets in subject specific kits. Each subject will be provided with study drug specific to that subject's randomization at the Baseline Visit (Visit 3, Week 0) and at each study visit during the treatment period (Visits 4 and 5, Weeks 4 and 8). Each set of blister cards dispensed will contain sufficient study drug to last until the next visit, with additional study drug to cover scheduling anomalies or lost study drug. Used study drug will not be re-dispensed.

Study drug supplies will be maintained at the site under controlled conditions and dispensed by a pharmacist or other qualified personnel at each study site. Study drug labels will contain information to meet the applicable regulatory requirements.

9.3. Study Drug Storage

The study drug must be stored under controlled room temperature (15 to 30°C [59-86°F]). Temperature will be monitored continuously and logged by appropriate Study Center staff until dispensed to the subjects in the study.

Study drug must be dispensed or administered according to procedures described herein. Only subjects enrolled in the study may receive the study drug, in accordance with all applicable regulatory requirements. Only authorized site staff may supply or administer study drug.

9.4. Study Drug Preparation

Study drug will be prepared by Patheon, Inc. in the form of oral tablets and packaged in blister cards as detailed in Section 9.2.

9.5. Administration

During the Run-In Period subjects will take 1 tablet of single-blind study drug in the AM and 1 tablet in the PM without regards to meals. The first dose of study drug will be taken the evening of the Run-In Visit.

Subjects will take 1 tablet of double-blind study drug in the AM and 1 tablet in the PM during the Double-Blind Treatment Period without regards to meal times. In regards to dosing on days of clinic visits during the Double-Blind Treatment Period, dosing will be slightly different between PK and non-PK subjects to accommodate PK sampling. PK subjects will dose in the clinic at each visit during the Double-Blind Treatment Period and therefore visits will generally be required to occur in the morning. Non-PK subjects are not required to dose in the office and there is no constraint on the time of day a visit can occur. Non-PK subjects will take their first dose of blinded study drug in the evening of the day of randomization.

9.6. Study Drug Accountability

The Investigator is responsible for the study drug accountability, reconciliation, and record maintenance. Subjects must return all unused study drug to the clinic at each visit.

9.7. Study Drug Handling and Disposal

Unused supplies will be disposed of using appropriate documentation according to International Conference on Harmonization-Good Clinical Practice (ICH-GCP), local requirements, applicable Occupational Safety and Health Administration (OSHA) and Environmental Protection Agency (EPA) regulations, and applicable study-specific procedures.

10. ASSESSMENT OF PHARMACOKINETICS AND BIOMARKERS

10.1. Sample Collection and Handling for Pharmacokinetic Samples

Plasma and urine PK samples will be identified by subject number. Sparse population blood and urine samples to document plasma and urine exposure of dexmecamylamine will be collected in about 200 subjects at the Baseline Visit (Week 0), Visit 4 (Week 4) and Visit 6 (Week 12).

10.1.1. Population PK Subjects

10.1.1.1. Plasma Sample

At the Baseline Visit (Week 0), Visit 4 (Week 4) and Visit 6 (Week 12) subjects will dose in the clinic and a blood sample will be collected at pre-dose, and at least 2 hours and at least 5 hours post-dose. Approximately 6 mL total volume of blood will be collected for each sample. The exact times of blood sample collection must be recorded on the source document and the laboratory requisition form. The date and time of study drug administration "in-clinic" as well as the date and time of the previous dose of study drug will be recorded on the source document and in the CRF. Plasma samples will be prepared and plasma stored according to Sponsor instructions (i.e., ≤ -20°C) as described in Appendix 1. Samples will be analyzed as described in Section 10.2.

10.1.1.2. Urine Sample

Population PK subjects will provide a urine sample at about 3 hours post-dose at Baseline Visit (Visit 3, Week 0), Visit 4 (Week 4) and Visit 6 (Week 12). In addition to the exact time of collection, the total void volume of the sample and the time of previous micturition will be recorded on the source document and laboratory requisition form. Urine samples will be prepared and stored according to Sponsor instructions (i.e., ≤ -20°C) as described in Appendix 1. Samples will be analyzed as described in Section 10.2.

10.1.2. Non-Population PK Subjects – Random Dexmecamylamine Urine Sample

Subjects not participating in the PK portion of this study (non-PK subjects) will provide a random urine sample at Visit 4 (Week 4) and Visit 6 (Week 12). In addition to the exact time of collection, the time of last dose, the total void volume of the sample and the time of previous micturition will be recorded on the source document and the laboratory requisition form. Urine samples will be prepared and stored according to Sponsor instructions (i.e., ≤ -20°C) as described in Appendix 1. Samples will be analyzed as described in Section 10.2.

10.2. Analytical Procedures for Pharmacokinetic Samples

All plasma and urine samples will be analyzed to determine concentrations of dexmecamylamine using a validated, specific and sensitive Liquid Chromatography-Mass Spectrometry/Mass Spectrometry (LC-MS/MS) method. Sample analysis will be performed under supervision of the Sponsor at a contracted bioanalytical laboratory. Plasma and urine pharmacokinetic samples may be retained for future analysis of the metabolite profile for a period of up to 15 years, after which time the samples will be destroyed.

10.3. Pharmacokinetic Parameters

Pharmacokinetic analyses will be performed by the Sponsor or as contracted by the Sponsor. Approximate trough ($C_{min}$) and maximal ($C_{max}$) concentrations will be listed in tabular form by dose with descriptive statistics. The pharmacokinetic data collected in the present study may be subject to a cross-study population pharmacokinetic analysis at a later date. Those results, if produced, will be presented in a separate report.

Data permitting, urine concentrations of dexmecamylamine will be correlated with the treatment assignment of the subject as well as with the data from the diaries and other endpoints from each subject.

11. SCREENING ASSESSMENTS

The following assessments will be used for screening purposes only.

11.1. 3 Incontinence Questions (3IQ) Questionnaire

The 3IQ questionnaire is a questionnaire consisting of 3 questions that evaluates incontinence as: 1) stress only or stress predominant incontinence; 2) urgency only or urgency predominant incontinence; 3) mixed incontinence; or 4) incontinence due to other causes.[9] The questionnaire will be used to initially screen for subjects that report urge-predominant incontinence. For subject with incontinence (question 1 = yes) question 3b must be checked [i.e., leaked most often due to urge...] which indicates the subject has urge only or urge-predominant incontinence. The 3IQ will only be used at the Screening Visit.

11.2. OAB-V8

The OAB-V8 questionnaire will be used to ensure subjects have sufficient bother from their OAB symptoms to enroll in the study. This questionnaire has 8 questions evaluating the bother caused by bladder symptoms common to OAB.[10] The total summed score of the 8 questions must be greater than 15 for subjects to be considered to have sufficient symptom bother. This will only be assessed at the beginning of the Run-In Visit (Visit 2, Week -2) and prior to randomization at the Baseline Visit (Visit 3, Week 0).

12. ASSESSMENT OF EFFICACY

12.1. Diary

Subjects will record in their Diary, on the three days prior to the scheduled visit: 1) the time the subject woke up and the time the subject went to sleep; 2) the time of each micturition; and 3) the time of each leakage episode and whether the leakage was related to urge ("due to need to urinate") or not related to urge ("due to other reasons"). In addition, on Diary Day 1, each subject will measure and record the volume of each voluntary micturition over a 24 hr period. These voluntary voids should be documented on the Diary even if the volume was measured in error or not measured. The subject should be reminded of pending Diary completion and verification of void volume collection. Subjects that cannot complete the void volume on the first day or forgot to complete it on this day may collect this on an alternative day in consultation with the site. The Diary should be distributed and collected per the Time and Events Schedule (Figure 1).

12.1.1. Micturition Frequency

Micturition frequency is defined as the mean number of micturitions per 24 hours and will be calculated as the total number of micturitions in the Diary, divided by the total number of full days that were documented.

12.1.2. Urge Urinary Incontinence

UUI episodes are defined as any episode recorded in the Diary as a leak associated with urge to urinate ("due to need to urinate"). This is a co-primary efficacy endpoint of this study and is defined the change in the number of urge urinary incontinence episodes per 24 hours from baseline (Visit 3, Week 0) to the end of treatment (Visit 6, Week 12) as denoted in the subject's diary entries on the 3 study days prior to these visits.

12.1.3. Volume Voided per Micturition

The volume voided per voluntary micturition is determined by collecting the voided volume of urine in a collection "hat" and then the volume is determined by using a measuring container; and the volume recorded in the Diary.

12.1.4. Nocturia

This is defined as an urge to void that wakes the subject from sleep between the time the subject goes to sleep and the time the subject woke up. Nocturia episodes will be calculated as the number of micturitions between the time the subject went to sleep and the time the subject woke up.

12.2. Clinical Global Impression of Improvement

The CGI-I is a 7 point scale that requires the clinician to assess how much the subject's illness has improved or worsened relative to the baseline state at the beginning of intervention. This is assessed in-clinic per the Time and Events Schedule (Figure 1).

12.3. Patient Perception of Bladder Condition

The Patient Perception of Bladder Condition (PPBC) is a single-item global measure for patients with OAB.[11] This is assessed in-clinic per the Time and Events Schedule (Figure 1).

12.4. Urgency Questionnaire

The Urgency Questionnaire has 15 questions evaluating various aspects of the subject's urinary urgency including 4 Visual Analog Scales (VAS) questions assessing urgency impact, severity, intensity (related to incontinence), and discomfort.[12] This is assessed in-clinic per the Time and Events Schedule (Figure 1).

12.5. Quality of Life Assessments

12.5.1. Overactive Bladder Questionnaire - OABq

The OAB-q was developed to assess the symptom bother and health-related quality of life impact of OAB on patient's lives.[13,14] The instrument was developed and validated in both continent and incontinent OAB patients as well as among men and women. This is a 33-item questionnaire and each item is rated on a 6-point Likert scale. This is assessed in-clinic per the Time and Events Schedule (Figure 1).

13. ASSESSMENT OF SAFETY

13.1. Safety Parameters

13.1.1. Physical Examinations

Physical examinations will be conducted at visits indicated in the Time and Events Schedule (Figure 1). A physical exam at the Follow-up Visit is required only if an abnormality was detected at the previous visit. All of the physical examinations except for the physical exam at the Screening Visit are brief physical examinations.

13.1.2. Vital Signs

Blood pressure, pulse and respiratory rate will be assessed at visits indicated in the Time and Events Schedule (Figure 1). Blood pressure and heart rate will be recorded after at least 5 minutes rest in a sitting position. When an orthostatic blood pressure assessment is required the sitting blood pressure will be conducted first as above and then blood pressure will be recorded after standing for at least 2 and no more than 3 minutes. Respiratory rate will be included in the collection of vital signs. Height will only be recorded at the Screening Visit and weight will be recorded at the Screening Visit and at Visit 6 (Week 12). The collection of vital signs at the Follow-up Visit (Visit 7, Week 14) is required only if an abnormality was detected at the previous visit.

13.1.3. ECG

Digital twelve-lead ECGs will be recorded as at paper speed of 25 mm/sec so that the various ECG intervals (RR, PR, QRS, QT) can be calculated. These ECGs will be recorded at times indicated in the Time and Events Schedule (Figure 1). An ECG will be recorded at the Follow-up Visit only if an abnormality was detected at the previous visit.

The ECG will be recorded with the subject in a semi-recumbent position after at least 5 minutes of rest and until 4 regular consecutive complexes are available depending on heart rate. ECG interval estimates taken from the ECG will be recorded, and a central ECG reader will verify all values and readings. QTcB and QTcF will be calculated from each ECG tracing

13.1.4. Clinical Laboratory Tests

Blood samples for serum chemistry and hematology and a urine sample for urinalysis will be taken for evaluation of laboratory safety parameters per the Time and Events Schedule (Figure 1). Clinical laboratory tests are only required at the Follow-up Visit if an abnormality was detected at the previous visit. The Investigator must review the laboratory report, document this review, and record any clinically relevant changes occurring during the study in the adverse event section of the CRF. Tests will be performed by the central laboratory. A summary of tests is included in Appendix 2.

A drug and alcohol screen will be conducted according to the Time and Events Schedule (Figure 1). A urine pregnancy test will be conducted at the Screening Visit.

13.1.5. Residual Bladder Volume

Residual bladder volume (PVR) after urination will be measured by bladder ultrasonography performed in the clinic. This non-invasive test will be used to assess changes in PVR urine during the study. To perform the test, subjects will be asked to void in private and then within 5 minutes have a PVR assessment. Should the subject have a significant PVR (> 150 mL), the subject will be asked to drink (non-caffeine) fluid to fill the bladder to repeat the test. The subject will be documented to have a significant PVR if at least 2 voids resulted in a PVR of greater than 150 mL. Refer to the Time and Events Schedule (Figure 1) for the assessment schedule. This safety measure will be assessed as change from baseline (Visit 3, Week 0) through Visit 6 (Week 12). The PVR can be completed on a separate day than the scheduled visit particularly for sites utilizing an offsite laboratory. The PVR should be done in close proximity to the visit and preferably prior to the visit so results can be reviewed at the scheduled visit. The PVR results at baseline are required prior to randomization.

13.1.6. Columbia Suicide Severity Rating Scale (CSSRS)

The Columbia Suicide Severity Rating Scale (CSSRS) will be administered by a trained rater. Any evidence of suicidality must be managed immediately, as appropriate, by a qualified psychiatric healthcare worker. Refer to the Time and Events Schedule (Figure 1) for the assessment schedule.

13.2. Adverse and Serious Adverse Events

The Investigator is responsible for the detection and documentation of events meeting the criteria and definition of a non-serious AE or SAE as provided in this protocol. During the study, as defined from the time of informed consent until the end of the Follow-up Visit (Week 14), the Investigator or site staff will be responsible for detecting and following AEs and SAEs, as detailed in this section of the protocol. Adverse events will be reported by the subject (or, when appropriate, by a caregiver, surrogate, or the subject's legally acceptable representative).

13.2.1. Definitions

13.2.1.1. Adverse Event (AE)

An adverse event (AE) is any untoward medical occurrence associated with the use of a drug in humans, whether or not considered drug related. An adverse event can therefore be any unfavorable and unintended sign (including an abnormal laboratory finding), symptom, or disease temporally associated with the use of a drug and does not imply any judgement about causality. An adverse event can arise with use of any drug or medicinal product.

13.2.1.2. Serious Adverse Event (SAE)

A serious adverse event (SAE) is any untoward medical occurrence that occurs irrespective of study treatment assignment, if it satisfies any of these criteria: results in death; is life-threatening; requires inpatient hospitalization or prolongs existing hospitalization; results in persistent or significant disability or incapacity or substantial disruption of the ability to conduct normal life functions; or if the event is a congenital anomaly or birth defect. Important medical events that may not result in death, be life-threatening, or require hospitalization may be considered serious when, based upon appropriate medical judgment, they may jeopardize the patient or subject and may require medical or surgical intervention to prevent one of the outcomes listed in this definition.

13.2.1.3. Suspected Adverse Reaction

A suspected adverse reaction is any adverse event for which there is a reasonable possibility that the drug caused the adverse event. For the purposes of IND safety reporting, "reasonable possibility" means there is evidence to suggest a causal relationship between the drug and the adverse event. Suspected adverse reaction implies a lesser degree of certainty about causality than adverse reaction, which means any adverse event caused by a drug.

13.2.1.4. Unexpected Adverse Event

An adverse event or suspected adverse reaction is considered "unexpected" if it is not listed in the investigator brochure or is not listed at the specificity or severity that has been observed.

13.2.2. Adverse Event Reporting

Subjects will be encouraged to spontaneously report any changes in baseline health from the time the subject enters the study on through discharge. Study staff will also inquire about adverse events on each visit while the subject is in the research center. All AEs will be recorded in the source document and the CRF.

13.2.3. Laboratory Abnormalities as Adverse Events

Abnormal laboratory findings (e.g., clinical chemistry, hematology, urinalysis) or other abnormal assessments (e.g., ECGs, vital signs, etc.) that are judged by the Investigator as clinically significant will be recorded as AEs or SAEs if they meet the definition of an AE, or SAE, as defined in Section 13.2.1. Clinically significant abnormal laboratory findings or other abnormal assessments that are detected during the study or are present at screening and significantly worsen following the start of the study will be reported as AEs or SAEs. However, clinically significant abnormal laboratory findings or other abnormal assessments that are associated with the disease being studied, unless judged by the Investigator as more severe than expected for the subject's condition, or that are present or detected at the start of the study and do not worsen, will not be reported as AEs or SAEs.

The Investigator, or his/her designee, will collect pregnancy information on every female who becomes pregnant while participating in this study. The Investigator, or his/her designee, will report to Targacept within 2 weeks of learning of a subject's pregnancy. The subject must also be followed to determine the outcome of the pregnancy. Information on the status of the mother and child will be forwarded to Targacept. Follow-up on the child will be for 1 year following the delivery date. Any premature termination of the pregnancy will be reported.

While pregnancy itself is not considered to be an AE or SAE, any pregnancy complication or elective termination of a pregnancy for medical reasons will be recorded as an AE or a SAE and followed as described in Sections 13.2-13.6.

A spontaneous abortion is always considered to be a SAE and will be reported as described in Section 13.2. Furthermore, any SAE occurring as a result of a post-study pregnancy and is considered reasonably related to the study drug by the Investigator, will be reported to Targacept. While the Investigator is not obligated to actively seek this information in former study participants, he/she may learn of an SAE through spontaneous reporting.

The Investigator will exercise his or her medical and scientific judgment in deciding whether an abnormal laboratory finding or other abnormal assessment is clinically significant.

13.3. Relationship to Study Drug

13.3.1. Assessment of Causality

The Investigator is obligated to assess the relationship between study drug and the occurrence of each AE/SAE. The Investigator will use clinical judgment to determine the relationship. Alternative causes, such as natural history of the underlying diseases, concomitant therapy, other risk factors, and the temporal relationship of the event to the study drug will be considered and investigated. The Investigator will also consult the Investigator's Brochure and/or Product Information for marketed products in the determination of his/her assessment.

The Investigator will assess causality based on the following definitions:

- Not Related (the AE was more likely explained by causes other than the study treatment).
- Related (the study treatment and AE were closely related in time and the AE may be explained by exposure to study product: e.g., known pharmacological effect or recurrence on re-challenge).

There may be situations when an SAE has occurred and the Investigator has minimal information to include in the initial report to Targacept or CRO. However, it is very important that the Investigator always make an assessment of causality for every event prior to transmission of the Event Reporting Form to Targacept or CRO. The Investigator may change his/her opinion of causality in light of follow-up information, amending the CRF and Targacept's Event Reporting Form accordingly. Because of its importance, any assessment of causality made by the Investigator should also be documented in the subject's source medical record.

13.4. Recording Adverse Events

When an AE occurs, it is the responsibility of the Investigator to review all documentation (e.g., hospital progress notes, laboratory, and diagnostics reports) relative to the event. The Investigator will then record all relevant information regarding an AE in the CRF. It is not acceptable for the Investigator to send photocopies of the subject's medical records to Sponsor in lieu of completion of the appropriate AE CRF entries.

However, there may be instances when Targacept or CRO requests copies of medical records for certain cases. In this instance, all subject identifiers will be blinded on the copies of the medical records prior to submission to Sponsor.

The Investigator will attempt to establish a diagnosis of the AE based on signs, symptoms, and/or other clinical information. In such cases, the diagnosis should be documented as the AE/SAE and not the individual signs/symptoms.

13.4.1. Eliciting Adverse Event Reports

At each visit, subjects will be asked about AEs by means of a non-leading question, such as "how have you been since your last visit?" or "how has the medication been?" In this way, possibly more mild, but clinically important, side effects of the study drug can be detected. SAEs will be reported promptly to Targacept or CRO as described in the following table once the Investigator determines that the event meets the protocol definition of a SAE.

13.4.2. Assessment of Intensity

The Investigator will make an assessment of intensity for each AE and SAE reported during the study. The assessment will be based on the Investigator's clinical judgment. The intensity of each AE and SAE recorded in the CRF should be assigned to one of the following categories:

- Mild: An event that is easily tolerated by the subject, causing minimal discomfort and not interfering with everyday activities.
- Moderate: An event that is sufficiently discomforting to interfere with normal everyday activities.
- Severe: An event that prevents normal everyday activities.

An AE that is assessed as severe should not be confused with a SAE. Severity is a category utilized for rating the intensity of an event; and both AEs and SAEs can be assessed as severe.

13.4.3. Adverse Events of Special Interest

The following AE will be considered AEs of Special Interest and will be reported identical to SAEs (below). The following AEs of Special Interest will be medically managed, as appropriate.

- Symptomatic orthostatic hypotension
- Syncope
- Suicidal ideation (subjects must see a qualified psychiatric healthcare worker)

13.5. Reporting Adverse Events

13.5.1. SAE Reporting Procedures

Once an Investigator becomes aware that a SAE has occurred in a study subject, she/he will report the information to Targacept or Targacept's representative within 24 hours. The Event Reporting Form used for reporting to Targacept's representative will always be completed as thoroughly as possible with all available details of the event, signed by the Investigator (or designee), and forwarded to Targacept or Targacept's representative within the designated time frames. If the Investigator does not have all information regarding an SAE, he/she will not wait to receive additional information before notifying Targacept or Targacept's representative of the event and completing the form. The form will be updated when additional information is received. Timeframes for submitting SAE reports are shown below in Table 3.

Table 3: Timeframes for Submitting SAE Reports to Targacept or CRO

| Initial SAE Reports | | Follow-up Information on a Previously Reported SAE | |
|---|---|---|---|
| Time Frame | Documents | Time Frame | Documents |
| 24 hrs | Targacept Event Reporting Form | 24 hrs | Updated Targacept Event Reporting Form |

The Investigator will always provide an assessment of causality at the time of the initial report as described in Section 13.3.1.

An Email or Facsimile transmission of the Event Reporting Form is the preferred method to transmit this information to the project contact for SAE receipt. In rare circumstances and in the absence of email or facsimile equipment, notification by telephone is acceptable, with a copy of the Event Reporting Form sent by overnight mail. Initial notification via the telephone does not replace the need for the Investigator to complete and sign the SAE form within 24 hours.

Targacept will provide a list of project contacts for SAE receipt, fax numbers, telephone numbers, and mailing addresses.

13.5.1.1. Regulatory Reporting Requirements for SAEs

Targacept or Targacept's representative has a legal responsibility to notify, as appropriate, both the local regulatory authority and other regulatory agencies about the safety of a product under clinical investigation. Prompt notification of SAEs by the Investigator to the appropriate project contact for SAE receipt is essential so that legal obligations and ethical responsibilities towards the safety of other subjects are met.

13.5.2. Reporting Safety Information to the IRB

The Investigator, or responsible person according to local requirements, will comply with the applicable local regulatory requirements related to the reporting of SAEs to the Institutional Review Board (IRB) / Institutional Ethics Committee (IEC).

A given SAE may qualify for an IND Safety Report if the SAE is both attributable to the study drug and unexpected. In this case, all Investigators involved in studies with this drug will receive a copy of the Safety Report.

When a site receives an Initial or Follow-up safety report or other safety information (e.g., revised Clinical Investigator's Brochure/Investigator's Brochure) from Targacept, the responsible person according to local requirements is required to promptly notify his or her IRB.

13.5.3. Protocol Deviations Due to an Emergency or Adverse Event

Any subject experiencing an emergency or adverse event requiring immediate medical attention will receive appropriate medical management by medical staff at the site and at other clinical sites as indicated. These events will be reported to the Medical Monitor as soon as possible. If the medical management results in departure from the study protocol, the Medical Monitor will be responsible for granting permission for the subject to continue in the trial if the subject is able to return to study protocol adherence in a timely fashion. If the subject cannot return to the study protocol in a timely fashion, then the subject will be discontinued from the study and early termination data will be collected.

13.6. Follow-up of Adverse Events

After the initial AE/SAE report, the Investigator is required to proactively follow each subject and provide further information to Sponsor on the subject's condition.

All AEs and SAEs documented at a previous visit/contact and designated as ongoing, will be reviewed at subsequent visits/contacts.

All AEs and SAEs will be followed until resolution, until the condition stabilizes, until the event is otherwise explained, or until the subject is lost to follow-up. Once resolved, the appropriate CRF entries and Targacept Event Reporting Form forms will be updated.

The Investigator will ensure that follow-up includes any supplemental investigations as may be indicated to elucidate the nature and/or causality of the AE or SAE. This may include additional laboratory tests or investigations, histopathological examinations, or consultation with other health care professionals.

Targacept may request that the Investigator perform or arrange for the conduct of supplemental measurements and/or evaluations to elucidate as fully as possible the nature and/or causality of the AE or SAE. The Investigator is obligated to assist. If a subject dies during participation in the study or during a recognized follow-up period, Targacept will be provided with a copy of any post-mortem findings, including histopathology.

New or updated information will be recorded on the originally completed Targacept Event Reporting Form, with all changes signed and dated by the Investigator. This information will also be entered into the CRF.

Investigators are not obligated to actively seek AEs or SAEs in former study participants. However, if the Investigator learns of any SAE, including a death, at any time after a subject has been discharged from the study, and he/she considers the event reasonably related to the study drug, the Investigator would promptly notify Targacept.

A SAE considered related to study participation (e.g., procedures, invasive tests, a change in existing therapy), even if it occurs during the pre- or post-treatment period, will be reported promptly to Targacept.

14. STATISTICS

14.1. Description of Statistical Methods

14.1.1. Quantitative and Qualitative Parameters

Descriptive statistics (mean, median, standard error of the mean, standard deviation, minimum and maximum) will be calculated for quantitative parameters. To evaluate treatment differences, continuous measures will be analyzed using a Mixed Model Repeated Measures (MMRM) model. All statistical tests for the efficacy analyses will be two-sided and will be performed at the $p < 0.05$ level of significance.

14.1.2. Baseline Data Summary

Demographic data and subjects' characteristics at screening will be listed and summarized using descriptive statistics. Any deviations from inclusion/exclusion criteria will be listed.

14.1.3. Primary Efficacy Endpoint Analysis

The co-primary efficacy endpoints, micturitions and incontinence episodes, will each be analyzed using a MMRM analysis. The primary efficacy endpoints will be assessed based on a change from Baseline (Visit 3) to Week 12 (Visit 6). The MMRM model will be based on a model which includes center and baseline measure as covariates. Center will be treated as a fixed effect. The model will include effects for treatment, time and treatment by time interaction. The model will employ an unstructured variance-covariance matrix and use the Kenward-Roger adjustment for degrees of freedom. The statistical analysis plan (SAP) will provide greater detail regarding alternative models to be utilized if the model based on an unstructured variance-covariance fails to converge.

Since these endpoints are co-primaries, both must be statistically significant for the study to provide evidence of efficacy. Hence, no multiplicity adjustment is needed to deal with these co-primary endpoints. A multiplicity adjustment is however needed to deal with the three doses. The fixed sequence method will be utilized in this study. If both co-primary endpoints are significant for the 2 mg dose at the 0.05 level, the co-primary endpoints will be tested at the 0.05 level for the 1 mg dose. If both co-primary endpoints are significant at the 0.05 level for this dose, the co-primary endpoints will be tested at the 0.5 mg dose at the same alpha=0.05 level. The overall multiplicity procedure will be described in greater detail in the SAP.

14.1.4. Secondary Efficacy Endpoint Analyses

All continuous secondary efficacy endpoints will be based on the MMRM model described in the analysis of primary efficacy endpoints. No multiplicity adjustment will be used for secondary efficacy endpoints. All comparisons of the active doses of dexmecamylamine to placebo will be made at the two-sided 0.05 level, unadjusted for multiplicity.

14.1.5. Responder Analyses

<u>Urinary Incontinence Dry Rate</u>

Of the subjects who were classified as OAB "wet" at baseline, the proportion that are dry (no episodes of UUI) on the 72 hr diary at endpoint will be compared between subjects receiving placebo and each of the active doses of dexmecamylamine.

<u>Urinary Incontinence Improvement Rate</u>

Of the subjects who were classified as OAB "wet" at baseline, the proportion that have a greater than 50% reduction in UUI episodes on the 72 hr diary at endpoint will be compared between subjects receiving placebo and each of the active doses of dexmecamylamine.

<u>Urinary Frequency Normalization Rate</u>

The proportion of subjects who have a urinary frequency of less than 8 per 24 hr at study endpoint will be compared between subjects receiving placebo and each of the active doses of dexmecamylamine..

<u>Nocturia Cure Rate</u>

Of the subjects who had at least one episode of nocturia at baseline on the 72 hr diary, the proportion who have no episodes of nocturia on the 72 hr diary at endpoint will be compared between subjects receiving placebo and each of the active doses of dexmecamylamine.

<u>Global Improvement Rate</u>

The proportion of subjects who have improvement on the Global Scale (CGI-I score greater than 3) at study endpoint will be compared between subjects receiving placebo and each of the active doses of dexmecamylamine.

For each endpoint, the analysis of the proportion of subjects responding will be based on the Cochran-Mantel-Haenszel chi-square and will be stratified by center. This analysis will compare the proportion of placebo subjects responding to the proportion of dexmecamylamine subjects responding for each dose while adjusting for the effect of center.

14.1.6. Key Safety Analyses

14.1.6.1. Post-void Residual Urine Volume Analyses

The mean change from baseline to endpoint will be compared between subjects receiving placebo and each of the active doses of dexmecamylamine. In addition the proportion of subjects who have greater than 200 mL PVR urine volume will be compared between subjects receiving placebo and each of the active doses of dexmecamylamine.

14.1.6.2. Retention of Urine Analysis

The proportion of subjects requiring catheterization for voiding difficulty, excessive PVR or acute retention will be compared between subjects receiving placebo and each of the active doses of dexmecamylamine.

14.1.7. Pharmacokinetic Analysis

Data will be listed for all individual subjects in the PK subset with available dexmecamylamine plasma concentrations. All concentrations below the lower limit of quantitation (LLOQ) or missing data will be labeled as such in the concentration data listings.

Factors which may influence the plasma concentrations (e.g., vomiting, diarrhea, co-medication, fever, high pre-dose concentration) will be checked. If any influencing factor is present, a decision will be made by the responsible pharmacokineticist whether to include or exclude the specific sample or subject. All subjects and samples excluded from the analysis will be clearly documented in the study report.

Descriptive statistics, including arithmetic mean, geometric mean, standard deviation, coefficient of variation, median, minimum, and maximum will be calculated for the dexmecamylamine plasma concentrations at each sampling time and for all derived PK parameters (approximations of $C_{min}$ and $C_{max}$) of dexmecamylamine.

Data permitting, urine concentrations of dexmecamylamine will be correlated with the treatment assignment of the subjects as well as with the data from the bladder diaries and other endpoints from each subject.

14.2. Sample Size

Enough subjects will be enrolled into a 2-week Run-In Period such that a total of approximately 750 subjects will be included into the Double-Blind Treatment Period of the study. There will be 3 active arms (0.5 mg *bid*, 1 mg *bid* and 2 mg *bid*) with 150 subjects per arm, and 1 placebo arm (placebo *bid*) with 300 subjects.

This study is powered to demonstrate a statistically significant difference between each dose of dexmecamylamine and placebo in the change from Baseline (Visit 3, Week 0) to Visit 6 (Week 12) for the co-primary endpoints, micturitions/24 hours and urinary incontinence episodes/24 hours. The number of subjects needed in total is 750 (150 per active treatment arm and 300 in the placebo arm), to detect a difference of 1.0 points for both co-primary endpoints with 91% power using a two-sided test and a significance level of 5% ($p < 0.05$), assuming a standard deviation (SD) of 2.5 (both endpoints) with normally distributed errors. This sample size will provide a power of 0.98 for the endpoint of micturitions/24 hours and a power of 0.93 for the endpoint of urinary incontinence episodes (based on the assumption that only 75% of subjects will have baseline urinary incontinence episodes and will be evaluable for this endpoint). The study will have a joint power for these co-primary endpoints of at least 0.91 (0.98 x 0.93). This calculation makes the conservative assumption that these endpoints are independent. Since these endpoints should be positively correlated, 0.91 should serve as a lower bound on power.

This sample size estimate is based on the assumption that 98% of randomized subjects are evaluable in the modified intention to treat (mITT) analysis set.

14.2.1. Level of Significance

The level of significance used for all efficacy variables will be defined by an $\alpha$ level of 0.05 using two-tailed tests.

14.3. Procedure for Accounting for Missing, Unused, and Spurious Data

Detail regarding procedures for accounting for missing, unused, and spurious data will be elaborated in the study specific statistical analysis plan (SAP).

14.4. Analysis of Patients Withdrawing Prematurely from the Study

Randomized subjects who withdraw prematurely from the study should complete all necessary assessments in the early termination visit. A summary of all-cause discontinuation will be provided. All information for withdrawing subjects will be included in safety analyses.

14.5. Selection of Patients To Be Included in Analyses

The mITT analysis set will contain all randomized subjects who receive study drug (drug or placebo) and have at least one post-baseline efficacy assessment. The primary efficacy analysis will be performed on the mITT analysis set.

The safety analysis set will contain all randomized subjects who receive at least one dose of the study drug (dexmecamylamine or placebo) and have at least one post-baseline safety assessment.

The per-protocol (PP) analysis set will include only randomized subjects who complete the study, and are fully compliant with all aspects of the protocol, including 80% compliance with study drug administration. Secondary efficacy analysis will be performed on the PP data set.

The Pharmacokinetic analysis set will consist of those subjects who are included in the mITT analysis set and who have pharmacokinetic plasma and/or urine samples. Pharmacokinetic summary statistical analyses will be performed on this set (PK subjects).

15. DIRECT ACCESS TO SOURCE DATA/DOCUMENTS

15.1. Study Monitoring

In accordance with applicable regulations, ICH-GCP and procedures covering the study, a monitor will contact the site prior to the subject enrollment to review the protocol and data collection procedures with site staff. In addition, the monitor will periodically contact the site, including conducting on-site visits at an appropriate frequency to ensure data quality and to ensure the safety and rights of subjects are being protected.

The investigator agrees to allow the monitor direct access to all relevant documents and to allocate his/her time and the time of his/her staff to the monitor to discuss findings and any relevant issues.

At study closure, monitors will also conduct all activities described in Section 18.3.

15.2. Audits and Inspections

To ensure compliance with Good Clinical Practices and all applicable regulatory requirements, quality assurance audits may occur during the study or after the study is complete. Authorized representatives of Targacept, the CRO conducting the study, a regulatory authority, an IRB may visit the site to perform audits or inspections to examine all study-related activities and documents to determine whether these activities were conducted, and data were recorded, analyzed, and accurately reported according to the protocol, ICH-GCP, and any applicable regulatory requirements.

If an audit or inspection occurs, the Investigator and institution agree to allow the auditor/inspector direct access to all relevant documents and to allocate his/her time and the time of his/her staff to the auditor/inspector to discuss findings and any relevant issues. The Investigator should contact Targacept immediately if contacted by a regulatory agency about an inspection.

15.3. Institutional Review Board (IRB)

This study will be conducted in full compliance with the Institutional Review Board (IRB) regulations in 21 CFR 56 and applicable local regulatory guidance, in accordance with ICH-GCP.

IRB approval for the investigation must be obtained before the study is initiated. Initial IRB approval, and all materials approved by the IRB for this study including the patient consent form and recruitment materials must be maintained by the Investigator and made available for inspection.

16. QUALITY CONTROL AND QUALITY ASSURANCE

To ensure compliance with Good Clinical Practices and all applicable regulatory requirements, Targacept (or representative of Targacept) may conduct a quality assurance audit. Please see Section 15.2 and 18.5 for more details regarding the audit process at any time during the conduct of the study or after study completion.

16.1. Regulatory Authority Approval

Targacept will obtain approval to conduct the study from the Food and Drug Administration (FDA) in accordance with FDA regulatory requirements prior to conducting the study.

16.2. Protocol Modifications

The initial protocol as well as all protocol amendments must be signed and dated by the Investigator and approved by the IRB prior to implementation of the original protocol and any amendment. The Principal Investigator must submit all protocol modifications to the IRB, as applicable for specific Investigators, or applicable local regulatory authority. Targacept or designee will submit protocol modifications to the FDA.

Departures from the protocol will be determined as allowable on a case-by-case basis or in event of an emergency involving subject safety. The Investigator or other physician in attendance must contact the Medical Monitor as soon as possible to discuss the circumstances of the emergency. The Medical Monitor, in concurrence with the Investigator, will decide whether the patient should continue to participate in the study. All protocol deviations and the reason for such deviations must be noted on the source document and in the CRF, and reported to the IRB as appropriate.

17. ETHICS

17.1. Ethics Review

The Investigator is responsible for ensuring that this protocol, the site's informed consent form (ICF), and any other information that will be presented to potential subjects (e.g., advertisements or information that supports or supplements the informed consent) are reviewed and approved by the appropriate IRB. The Investigator agrees to allow the IRB direct access to all relevant documents. The IRB must be constituted in accordance with all applicable regulatory requirements. Targacept or CRO will provide the Investigator with relevant document(s)/data that are needed for IRB review and approval of the study. The IRB must approve the study and ICF before study drug(s) and other study material can be shipped to the site.

If the protocol, the ICF, or any other information that the IRB has approved for presentation to potential subjects is amended during the study, the Investigator is responsible for ensuring the IRB reviews and approves, where applicable, these amended documents. The Investigator must follow all applicable regulatory requirements pertaining to the use of an amended ICF including obtaining IRB approval of the amended form before new subjects consent to take part in the study using this version of the form. Copies of the IRB approval of the amended ICF/other information and the approved amended ICF/other information must be forwarded to the CRO managing the study.

17.2. Ethical Conduct of the Study

This study will be conducted in accordance with ICH-GCP guidelines and all applicable regulatory requirements, including, where applicable, the Declaration of Helsinki.

17.3. Written Informed Consent

This study will be conducted in full compliance with the informed consent regulations in 21 CFR 50. The consent form must be reviewed and approved by the Sponsor prior to submission to the IRB. The consent form must be approved by the IRB prior to initiation of the study.

No Investigator may involve a human being as a subject in research unless the Investigator has obtained the legally effective informed consent of the subject or the subject's legally authorized representative. An Investigator may seek such consent only under circumstances that provide the prospective subject or the representative sufficient opportunity to consider whether to participate and that minimize the possibility of coercion or undue influence. The information given to the subject or the representative must be in a language understandable to the subject or the representative. No informed consent, whether oral or written, may include any exculpatory language through which the subject or the representative is made to waive or appear to waive any of the subject's legal rights, or releases or appears to release the Investigator, the institution, the Sponsor, or its agents from liability for negligence.

An IRB-approved consent form should inform each prospective subject or the legally authorized representative of each prospective subject of the purpose and the nature of the study, its possible hazards and benefits, and the subject's right to withdraw from the study at any time without prejudice to further treatment. Exemptions to the requirement for informed consent in the United States are described in 21 CFR 50.23.

The Investigator(s) at each center will ensure that the patient is given full and adequate oral and written information about the nature, purpose, possible risk and benefit of the study. Patients must also be notified that they are free to discontinue from the study at any time. The patient should be given the opportunity to ask questions and allowed time to consider the information provided.

The Investigator is responsible for obtaining written consent (signed and dated ICF) from potential subjects prior to performing any trial tests or assessments required by the protocol. A copy of the signed consent document will be given to the patient and the original retained by the Investigator

18. DATA HANDLING AND RECORDKEEPING

18.1. Case Report Form Completion and Source Documentation

The Investigator is required to prepare and maintain adequate and accurate case histories designed to record all observations and other data pertinent to the study for each study participant. Subject data are collected by the investigator or designee using source documents that are entered into a CRF, defined by Targacept. An electronic CRF will be used in this study. Subject data necessary for analysis and reporting will be entered onto the source documents and then into the validated CRF database system.

All information recorded on CRFs must be consistent with the subject's source documentation (i.e., medical records). The Investigator is responsible for the accuracy of the data transcribed from all source documentation. All CRF entries should be made within a reasonable timeframe from the time of a subject's visit. A monitor representing the sponsor will verify the CRF documentation for each patient against the source documents at the study center. Instances of missing or uninterpretable data will be brought to the attention of the investigator and/or sponsor for resolution.

18.2. Data Management

Clinical data management will be performed in accordance with applicable study standards and data cleaning procedures. Database lock will occur when data management quality control procedures are completed.

18.3. Study Site Close-Out

Upon completion of the study, the monitor may conduct the following activities in conjunction with the investigator or site staff, as appropriate:

1. Resolve data queries.
2. Accountability, reconciliation, and return of unused study drug(s).
3. Review of final site study records for completeness.
4. Return all study-specific equipment to Targacept.

18.4. Retention of Study Documents and Records

Following closure of the study, the Investigator must maintain all site study records in a safe and secure location. All CRF data will be retained by and are the sole property of Targacept. The investigator will retain a copy of all source documents and CRF data (i.e., DVD-ROM containing pdf files of CRFs provided by the sponsor) for the subjects enrolled at the site. The records must be maintained to allow easy and timely retrieval, when needed (e.g., audit or inspection). Where permitted by local laws/regulations or institutional policy, some or all of these records can be maintained in a format other than hard copy (e.g., microfiche, scanned, electronic); however, caution needs to be exercised before such action is taken. The Investigator must assure that all reproductions are legible and are a true and accurate copy of the original and meet accessibility and retrieval standards, including re-generating a hard copy, if required. Furthermore, the Investigator must ensure there is an acceptable back-up of these reproductions and that an acceptable quality control process exists for making these reproductions.

Targacept will inform the Investigator of the time period for retaining these records to comply with all applicable regulatory requirements. The minimum retention time will meet the strictest standard applicable to that site for the study, as dictated by any institutional requirements or local laws or regulations, or Targacept standards/procedures; otherwise, the retention period will default to 15 years.

The Investigator must notify Targacept of any changes in the archival arrangements, including, but not limited to, the following: archival at an off-site facility, transfer of ownership of the records in the event the Investigator leaves the site.

18.5. Inspection of Records

Targacept (or a representative of Targacept) will be allowed to conduct site visits to the investigation facilities for the purpose of monitoring any aspect of the study. The Investigator agrees to allow the monitor to inspect the drug storage area, study drug stocks, drug accountability records, subject charts and study source documents, and other records relative to study conduct.

19. INVENTION AND PUBLICATION POLICY

In the event of a conflict between the provisions of this section and a written contract regarding the conduct of Study between Sponsor (or a contract research organization) and the site, the Investigator or any person assisting Investigator with the Study, the terms of that contract shall control.

19.1. Ownership

All information provided by or on behalf of Sponsor and all data and information generated by the site, the Investigator or any person assisting Investigator with the Study as part of or in connection with the Study (other than a subject's medical records), is the sole and exclusive property of Sponsor. All rights, title, and interests in and to any inventions, discoveries or know-how made, conceived, learned or first reduced to practice by the site, Investigator or any person assisting Investigator with the Study during the course of, in relation to, or as a result of the Study (and any intellectual property rights related thereto) are the sole and exclusive property of the Sponsor, and are hereby assigned to Sponsor.

19.2. Confidentiality

All information provided by Targacept and all data and information generated by the site as part of or in relation to the Study (other than a subject's medical records) will be kept confidential by the Investigator, the site, and any person assisting Investigator with the Study. This information and data shall not be used by the site, Investigator, or any person assisting Investigator with the Study for any purpose other than conducting the Study. These restrictions do not apply to: 1) information which becomes publicly available through no fault of the site, Investigator or any person assisting Investigator with the Study; 2) information which it is necessary to disclose in confidence to an IRB solely for the evaluation of the Study; 3) information which it is necessary to disclose in order to provide appropriate medical care to a Study subject; or 4) Study results which are permitted to be published as described in the next section.

19.3. Publication

If the Study is a multi-center study, the first publication or disclosure of Study results shall include data from all sites.

Investigator may publish the results of the Study only for noncommercial, educational or academic purposes provided that: 1) said publication is made after the multi-center publication; and 2) prior to making the publication, or otherwise disclosing the Study results, Investigator provides Sponsor with a copy of the proposed publication and allows Sponsor a reasonable period to review. Proposed publications shall not include Targacept confidential information (other than the Study results) or personal data with respect to any subject (such as name or initials) and if Targacept identifies any such Targacept confidential information in a proposed publication, it shall be removed.

At Targacept's request, the submission, publication or other disclosure of a proposed publication will be delayed a sufficient time to allow Targacept to seek patent or similar protection of any inventions, know-how or other intellectual or industrial property rights contained in such proposed publication.

20. LIST OF REFERENCES

1. Abrams P, Cardozo L, Fall M et al. The standardization of terminology of lower urinary tract function: report from the Standardization Subcommittee of the International Continence Society. Neurourol Urodyn 21: 167-178, 2002.
2. Milsom I, Stewart W, and Thuroff J. The prevalence of overactive bladder. Am J Manag Care 6 (11 suppl):S565-S573, 2000.
3. Milsom I, Abrams P, Cardozo L, et al. How widespread are the symptoms of an overactive bladder and how are they managed? A population-based prevalence study. Br J Urol Int 87:760-766, 2001.
4. Abrams P and Wein AJ. Introduction: overactive bladder and its treatments. Urology 55 (suppl 5A): 1-2, 2000.
5. Wagg A, Compion G, Fahey A, Siddiqui E, Persistence with prescribed antimuscarinic therapy for overactive bladder: a UK experience. BJU Int 110:1767-74, 2012.
6. Yeaw J, Benner J, Walt J, Sian S, Smith D. Comparing adherence and persistence across 6 chronic medication classes, J Manag Care Pharm 15:728-740, 2009.
7. Beckel JM, Kanai A, Lee S-J et al. Expression of functional nicotinic acetylcholine receptors in rat urinary bladder epithelial cells. Am J Physiol Renal Physiol 290:F103-10, 2006.
8. Mallinckrodt CH, Tamura RN, Tanaka Y. Recent developments in improving signal detection and reducing placebo response in psychiatric clinical trials. J Psychiatr Res 45:1202-7, 2011.
9. Brown JS, Bradley CS, Subak LL, Richter HE, Kraus SR, Brubaker L, Lin F, Vittinghoff E, Grady D; Diagnostic Aspects of Incontinence Study (DAISy) Research Group. The sensitivity and specificity of a simple test to distinguish between urge and stress urinary incontinence. Ann Intern Med 144:715-23, 2006.
10. Coyne KS, Zyczynski T, Margolis MK, Elinoff V, Roberts RG. Validation of an overactive bladder awareness tool for use in primary care settings. Adv Ther 22:381-94, 2005.
11. Coyne KS, Matza LS, Kopp Z, Abrams P. The validation of the patient perception of bladder condition (PPBC): a single-item global measure for patients with overactive bladder. Eur Urol 49:1079-86, 2006.
12. Matza LS, Thompson CL, Krasnow J, Brewster-Jordan J, Zyczynski T, Coyne KS. Test-retest reliability of four questionnaires for patients with overactive bladder: the overactive bladder questionnaire (OAB-q), patient perception of bladder condition (PPBC), urgency questionnaire (UQ), and the primary OAB symptom questionnaire (POSQ). Neurourol Urodyn 24:215-25, 2005.

13. Coyne K, Revicki D, Hunt T, Corey R, Stewart W, Bentkover J, Kurth H, Abrams P. Psychometric validation of an overactive bladder symptom and health-related quality of life questionnaire: the OAB-q. Qual Life Res 11:563-74, 2002.

14. Coyne KS, Matza LS, Thompson CL. The responsiveness of the Overactive Bladder Questionnaire (OAB-q). Qual Life Res 14:849-55, 2005.

21. APPENDICES

Appendix 1. Pharmacokinetic Sample Collection, Handling and Shipping
Materials and Labeling:

Blood must be collected in glass or plastic K$_2$EDTA containing blood collection tubes (e.g., Vacutainer®). Resulting plasma samples must be stored in polypropylene storage tubes. No tubes with separation gel should be used.

All tubes and containers will be labeled with preprinted labels. The preprinted information will include whether the sample is a plasma or urine sample, whether it is a primary or backup sample and should include the scheduled study time point. Other information may be included on label without deviation if approved by Sponsor.

Preparation of Plasma Pharmacokinetic Samples:

- Collect 6 mL of blood into the appropriate K$_2$EDTA containing collection tube (e.g., Vacutainer®) at each time point.
- Record the exact date and time of sampling on the lab requisition form.
- Gently invert the tubes 8 to 10 times to afford mixing, before processing.
- Centrifuge blood samples at room temperature within 1 hour of collection in a clinical centrifuge at 1,300 g for 10 minutes, unless otherwise specified by the supplier.
- The approximate 3 mL of plasma (after centrifugation) will be split evenly between two storage tubes each containing approximately 1.5 mL plasma.
- Transfer all separated plasma immediately with a clean, disposable glass or polyethylene pipette (use 1 new pipette per sample) to the pre-labeled storage tube.
- Store plasma samples in an upright position, in a non-frost-free freezer (at approximately $-20°C$ or lower) until transfer to the central laboratory. The temperature of the storage conditions should be monitored.
- The time between blood collection and freezing the plasma will not exceed 2 hours.

Preparation of Urine Pharmacokinetic Samples

- Collect a urine sample in a clean urine collection container.
- Measure the total volume of the urine, then transfer 2 mL aliquots into two appropriately labeled polypropylene urine storage tubes.
- Record the exact date and time of sampling on the lab requisition form.
- Store the urine samples in an upright position in a non-frost free freezer (at approximately $-20°C$ or lower) until transfer to the central laboratory. The temperature of the storage conditions should be monitored.

Shipment of Pharmacokinetic Samples:

All pharmacokinetic samples will be sent to the central laboratory in multiple shipments as agreed upon with the Sponsor. An inventory list must be included with each shipment. The inventory list must note each specimen drawn for each subject, and note any missing specimens.

The Investigator must follow the instructions below:

- Ship specimens according to the instructions provided by the central laboratory or bioanalytical facility, sorted by subject, by sample collection date and time.
- For domestic shipments in the US, a reliable domestic courier such as Federal Express will be used.
- The central laboratory will be notified by fax or email that a shipment of samples is imminent. This notification will be made before the shipping date.
- Notify the central laboratory and the courier at least 24 hours in advance of the planned shipment. Provide the courier with the appropriate account number to be used, if applicable.
- Unless agreements were made with the Sponsor, samples will be shipped via overnight delivery only on Monday through Wednesday, excluding holidays.
- Double-bag the frozen samples for each subject in bags that can withstand dry ice conditions (e.g., cryogenic bags), and label with CRF I.D.#. Pack the frozen samples in sufficient quantity of dry ice in appropriate containers, to maintain a frozen state for at least 3 days.
- Avoid direct contact between sample bags and dry ice by separating them with a dry ice resistant material (e.g., newspaper).
- Ensure that the total package weight does not exceed 27.2 kg (60 pounds). Label the package with the Sponsor name and study number.
- Include a return address (which includes the Investigator's name) on the outside of each shipping container.
- Retain all documents indicating date, time, and signature(s) of person(s) making the shipment, in the study files.

As soon as shipment day and air bill number(s) are available, the site will call, fax or email the central laboratory. The call, fax or email must specify the study number, the number of pharmacokinetic samples, and the time of shipment pick-up.

Questions regarding handling the pharmacokinetic specimens should be addressed to the contact person of the Sponsor. Alternative procedures will not result in a protocol amendment if approved by the Sponsor.

Appendix 2. Clinical Laboratory Tests

- Chem 20 panel plus direct bilirubin, creatine kinase, magnesium
- PSA (at the Screening Visit only).
- Hematology and differential panel
- Urinalysis macro panel followed by micro panel for +1 blood, nitrite, leukocyte esterase
- Urine drug screen
- Urine pregnancy test for women of childbearing potential See TIME AND EVENTS SCHEDULE (Figure 1).

The specific pharmacological responses observed may vary according to and depending on the particular active compound, including a particular salt form, selected or whether there are present pharmaceutical carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:

1. A method of treating overactive bladder, the method comprising the oral administration of dexmecamylamine or a pharmaceutically acceptable salt thereof in an amount from about 0.1 mg to about 2.0 mg twice daily, substantially free of exo-R-mecamylamine, to a human patient with overactive bladder.

2. The method according to claim 1, wherein the oral administration of dexmecamylamine is sufficient to increase the micturition interval by at least 10% relative to baseline in the human patient.

3. The method according to claim 1, wherein the dexmecamylamine or a pharmaceutically acceptable salt thereof is orally administered in an amount of about 0.5 mg twice, daily.

4. The method according to claim 1, wherein the dexmecamylamine or a pharmaceutically acceptable salt thereof is orally administered in an amount of about 1.0 mg twice daily.

5. The method according to claim 1, wherein the dexmecamylamine or a pharmaceutically acceptable salt thereof is orally administered in an amount of about 2.0 mg twice daily.

6. The method according to claim 1, wherein the dexmecamylamine or a pharmaceutically acceptable salt thereof is orally administered in tablet form.

7. The method according to claim 1, wherein the administration of dexmecamylamine is sufficient to increase the micturition interval by at least 10% relative to baseline without significant detrimental changes in bladder contraction amplitude in the human patient.

* * * * *